(12) United States Patent
Chibber

(10) Patent No.: US 7,906,493 B2
(45) Date of Patent: Mar. 15, 2011

(54) CORE 2 GLCNAC-T INHIBITORS

(75) Inventor: Rakesh Chibber, London (GB)

(73) Assignee: BTG International Limited, London (GB)

( * ) Notice: Subject to any disclaimer, the term of this patent is extended or adjusted under 35 U.S.C. 154(b) by 588 days.

(21) Appl. No.: 10/584,470

(22) PCT Filed: Dec. 22, 2004

(86) PCT No.: PCT/GB2004/005398
§ 371 (c)(1),
(2), (4) Date: Aug. 9, 2006

(87) PCT Pub. No.: WO2005/060977
PCT Pub. Date: Jul. 7, 2005

(65) Prior Publication Data
US 2008/0318875 A1    Dec. 25, 2008

(30) Foreign Application Priority Data
Dec. 22, 2003    (GB) ................................. 0329667.0

(51) Int. Cl.
*A61K 31/715*    (2006.01)

(52) U.S. Cl. ................. 514/61; 514/25; 514/54; 514/62

(58) Field of Classification Search .................. None
See application file for complete search history.

(56) References Cited

U.S. PATENT DOCUMENTS

| | | | |
|---|---|---|---|
| 4,602,003 A | 7/1986 | Malinow |
| 5,104,856 A | 4/1992 | Esko et al. |
| 5,360,733 A | 11/1994 | Fukuda et al. |
| 5,461,143 A | 10/1995 | Wong et al. |
| 5,470,879 A | 11/1995 | Sauvaire et al. |
| 5,486,510 A | 1/1996 | Bouic et al. |
| 5,589,182 A | 12/1996 | Tashiro et al. |
| 5,624,832 A | 4/1997 | Fukuda et al. |
| 5,658,778 A | 8/1997 | Fukuda et al. |
| 5,684,134 A | 11/1997 | Fukuda et al. |
| 5,827,884 A | 10/1998 | Obagi |
| 5,843,707 A | 12/1998 | Larsen et al. |
| 5,880,091 A | 3/1999 | Cummings et al. |
| 5,886,029 A | 3/1999 | Dhaliwal |
| 5,952,393 A | 9/1999 | Sorkin, Jr. |
| 5,958,770 A | 9/1999 | Cham et al. |
| 5,965,449 A | 10/1999 | Novak |
| 5,985,936 A | 11/1999 | Novak |
| 5,997,877 A | 12/1999 | Chang |
| 6,042,834 A | 3/2000 | Baraka |
| 6,087,353 A | 7/2000 | Stewart et al. |
| 6,131,578 A | 10/2000 | King et al. |
| 6,197,832 B1 | 3/2001 | Sorkin, Jr. |
| 6,294,157 B1 | 9/2001 | Rubinstenn et al. |
| 6,346,267 B1 | 2/2002 | Fry et al. |
| 6,383,514 B1 | 5/2002 | Weitkemper et al. |
| 6,407,085 B1 | 6/2002 | Kief |
| 6,451,355 B1 | 9/2002 | Reisner |
| 6,593,301 B1 | 7/2003 | Ma et al. |
| 6,635,461 B1 | 10/2003 | Schwientek et al. |
| 6,787,151 B2 | 9/2004 | Meijer et al. |
| 6,933,291 B2 | 8/2005 | Qi et al. |
| 6,998,501 B1 | 2/2006 | Wright et al. |
| 2002/0016314 A1 | 2/2002 | Schersi |
| 2002/0018811 A1 | 2/2002 | Penteado et al. |
| 2002/0098563 A1 | 7/2002 | Korczak et al. |
| 2002/0107292 A1 | 8/2002 | Bortlik et al. |
| 2002/0156051 A1 | 10/2002 | Kutney et al. |
| 2002/0183294 A1 | 12/2002 | Barraclough et al. |
| 2002/0193317 A1 | 12/2002 | Xia et al. |
| 2003/0004147 A1 | 1/2003 | Barraclough et al. |
| 2003/0096316 A1 | 5/2003 | Wester |
| 2003/0148962 A1 | 8/2003 | Guan et al. |
| 2004/0033521 A1 | 2/2004 | Korczak et al. |
| 2004/0038923 A1 | 2/2004 | Marth et al. |
| 2004/0049352 A1 | 3/2004 | Andre et al. |
| 2004/0203111 A1 | 10/2004 | Schwientek et al. |
| 2004/0220115 A1 | 11/2004 | Cham |
| 2004/0249138 A1 | 12/2004 | Lawson |
| 2006/0052351 A1 | 3/2006 | Platt et al. |
| 2007/0254847 A1 | 11/2007 | Liu et al. |
| 2008/0318875 A1 | 12/2008 | Chibber |

FOREIGN PATENT DOCUMENTS

| | | |
|---|---|---|
| CA | 2 186987 | 4/1998 |
| CA | 2186987 | 4/1998 |
| CA | 2 335 436 | 8/2001 |
| CN | 1237583 A | 12/1999 |
| CN | 1243129 A | 2/2000 |
| CN | 1361111 A | 12/2000 |
| CN | 1361111 A | 7/2002 |
| CN | 00135190.7 | 1/2005 |
| DE | 4303214 A1 | 11/1994 |
| EP | 0 251 197 | 1/1988 |
| EP | 0 251 197 A2 | 1/1988 |

(Continued)

OTHER PUBLICATIONS

Mimaki et al. Phytochemistry (1996), vol. 42, pp. 1065-1070.*

(Continued)

*Primary Examiner* — Patrick T Lewis
(74) *Attorney, Agent, or Firm* — Nixon & Vanderhye

(57) ABSTRACT

Method of treating conditions associated with raised activity of core 2 GlcNAc-T by administering an inhibitor of UDP-GlcNAc:Galβ1,3GalNAc-R (GlcNAc to GalNAc) β1,6-N-acetylglucosaminyl transferase (core 2 β1,6 N-acetylaminotransferase, core 2 GlcNAc-T-EC 2.4.1.102). Diseases associated with raised activity of core 2 GlcNAc-T include inflammatory diseases, atherosclerosis, diabetic cardiomyopathy, cancers, including treatment or prevention of metastasis, or diabetic retinopathy.

49 Claims, 13 Drawing Sheets

FOREIGN PATENT DOCUMENTS

| | | |
|---|---|---|
| EP | 0 251 197 A3 | 1/1988 |
| EP | 1 316 608 A1 | 6/2003 |
| EP | 0 850 243 B1 | 10/2003 |
| EP | 1 800 685 A1 | 6/2007 |
| JP | 03271224 A | 3/1991 |
| JP | 2004-143126 | 5/2004 |
| RU | 2 027 434 C1 | 1/1995 |
| RU | 2027434 | 1/1995 |
| SU | 833254 | 5/1981 |
| WO | WO 95/17182 A1 | 6/1995 |
| WO | WO 95/21199 A1 | 8/1995 |
| WO | WO 95/35294 A1 | 12/1995 |
| WO | WO 97/06176 A2 | 2/1997 |
| WO | WO 97/47298 A1 | 12/1997 |
| WO | WO 98/06405 A1 | 2/1998 |
| WO | 98/14459 | 4/1998 |
| WO | WO 98/33494 | 8/1998 |
| WO | WO 98/33494 A1 | 8/1998 |
| WO | WO 99/25197 | 5/1999 |
| WO | WO 99/25197 A1 | 5/1999 |
| WO | WO 99/39715 A1 | 8/1999 |
| WO | WO 99/53925 A1 | 10/1999 |
| WO | WO 00/31109 | 6/2000 |
| WO | WO 00/31109 A1 | 6/2000 |
| WO | WO 00/52029 A1 | 9/2000 |
| WO | WO 00/61153 | 10/2000 |
| WO | WO 00/78789 A1 | 12/2000 |
| WO | WO 01/32679 A2 | 5/2001 |
| WO | 01/58932 | 8/2001 |
| WO | WO 01/83717 A2 | 11/2001 |
| WO | WO01/87548 | 11/2001 |
| WO | WO 02/03996 A1 | 1/2002 |
| WO | WO 02/24212 A1 | 3/2002 |
| WO | WO 02/069980 A2 | 9/2002 |
| WO | WO 02/087548 A1 | 11/2002 |
| WO | 03/043433 | 5/2003 |
| WO | 03/066679 | 8/2003 |
| WO | WO 03/070261 A1 | 8/2003 |
| WO | WO 03/075931 A1 | 9/2003 |
| WO | 03/092394 | 11/2003 |
| WO | WO 2004/002497 A1 | 1/2004 |
| WO | WO 2004/019960 A2 | 3/2004 |
| WO | WO 2004/029068 A1 | 4/2004 |
| WO | WO 2004/048938 A2 | 6/2004 |
| WO | WO 2004/062675 A1 | 7/2004 |
| WO | WO 2004/064852 A1 | 8/2004 |
| WO | 2004/074461 | 9/2004 |
| WO | WO 2004/093662 A2 | 11/2004 |
| WO | WO 2004/111196 A2 | 12/2004 |
| WO | WO 2005/060977 A1 | 7/2005 |
| WO | WO 2005/084323 A2 | 9/2005 |
| WO | WO 2005/120535 A1 | 12/2005 |
| WO | 2006/034655 | 4/2006 |
| WO | WO 2006/034655 A1 | 4/2006 |
| WO | WO 2006/034655 A1 | 6/2006 |

OTHER PUBLICATIONS

Matsuda et al. Bioorg. Med. Chem. Lett. (2003), vol. 13, pp. 1101-1106.*
Friedman et al. Food and Chemical Toxicology (2003), vol. 41, pp. 61-71.*
Rita Aquino et al, "Furostanol Oligosides from Tamus Communis", Journal of Natural Products vol. 49, No. 6, pp. 1096-1101, Nov.-Dec. 1986.
Jean-Guy Bienvenu et al, "Recombinant Soluble P-Selectin Glycoprotein Ligan-1-Ig Reduces Restenosis through Inhibition of Platelet-Neutrophil Adhesion after Double Angioplasty in Swine", Circulation. 27;103(8):1128-34 (2001).
Chen C. et al, Yunnan Zhiwu Yanjiu, 9(4), 495-502 (1987).
Chow F. et al., "Macrophages in streptozotocin-induced diabetic nephropathy: potenial role in renal fibrosis" Nephrol Dial Transplant. 19(12):2987-96 (2004).
Dang B et al "Increased PSGL-1 expression on granulocytes from allergic-asthmatic subjects results in enhanced leukocyte recruitment under flow conditions", Journal of Leukocyte Biology, vol. 72,(4), pp. 702-710.
Dedrick R.L. et al , "Adhesition molecules as therapeutic targets for autoimmune diseases and transplant rejection".
Fujita S. et al , "Dammarane Glycosides from Aerial parts of Neoalsomitra Integrifoliola", Phytochemistry, 38(2), 465-72 (1995).
Guofeng Gu, et al , "Facile Synthesis of Saponins Containing 2,3-Branched Oligosaccharides by Using Partially Protecgted Glycosyl Donors", J. Org. Chem 2004, 69, 5497-5500.
Haladova M. et al., "Steroids saponins from the petals of Lilium candidum L.", Pharmazie, 54(2), 159-160 (1999).
Hansen A. et al., "Evaluation of Cardioprotective Effects of Recombinant Soluble P-Selectin Glycoprotein Ligan-Immunoglobulin in Myocardial Ischemia-Reperfusion Injury by Real-Time Myocardial Contrast Echocardiography" J Am Coll Cardiol. 18;44(4):887-91 (2004).
Hans-Peter Hartung et al, "Circulating Adhesion Molecules and Tumor Necrosis Factor Receptor in Multiple Sclerosis: Correlation with Magnetic Resonance Imaging" Ann Neurol 1995; 38(2), 186-193.
Hickey M. et al., "Leukocyte-Endothelial Cell Interactions are enhanced in Dermal Postcapillary Venules of MRL/fas$^{lpr}$ (Lupus-Prone) Mice: Roles of P- and E-Selectin[1]" J Immunol. 168(9):4728-36 (2002.
Haworth and Hirst, XXII—The Constitution of the Disaccharides. Part V, Vellobiose (Cellose)J. Chem. Soc. 119, 193 (1921).
Ke Hu et al, "Methyl protogracillin (NSC-698792): the spectrum of cytotoxicity against 60 human cancer cell lines in the National Cancer Institute;s anticancer drug screen panel", Anti-cancer Drugs 2001, 12, pp. 541-547.
Ke Hu et al "The Cytotoxity of Methyl Protoneogracillin (NSC-698793) and Gracillin (NSC-698787), Two Steroidal Saponins from the Rhizomes of Dioscorea collettii var. hypoglauca, against Human Cancer Cells in vitro", Phytother. Res. 17, 620-626 (2003).
Ke Hu et al "Antineoplastic Agents; 11. Four Furostanol Glycosides from Rhizomes of Dioscorea collettii var. hypoglauca", Planta Medica 63 (1997) 161-165.
Hurwitz AA et al "Tumor Necrosis Factor α Induces Adhesion Molecule Expression on Human Fetal Astrocytes", J. Exp. Med, 1992 vol. 176, Dec. 1992 pp. 1631-1636.
Kentaro Inoue et al, "Purification and characterization of furostanol glycoside 26-$O$-β-glucosidase from Costus speciosus rhizomes", FEDS Letters, 278 (1996) pp. 157-160.
Inoue T. et al., "Blockade of PSGL-1 attenuates CD14 +monocytic cell recruitment in intestinal mucosa and ameliorates ileitis in SAMP1/Yit mice", J Leukoc Biol. 77(3):287-95 (2005).
Toshio Kawasaki et al, "Furostanol Bisglycosides Corresponding to Dioscin and Gracillin", Chem Pharm Bull, 22990 2164-2175 (1074).
Kessar S. et al., "Synthetic Studies in Steroidal Sapogenins and Alkaloids-III" Tetrahedron. 24(2):887-92 (1968).
Kessar S et al., "Synthetic Studies in Steroidal Sapogenins and Alkaloids-V", Tetrahedron vol. 24, pp. 899-904 (1968).
Kessar S et al., "Synthetic Studies in Steroidal Sapogenins and Alkaloids-VI", Tetrahedron vol. 24, pp. 905-907 (1968).
Ravindra Kumar et al., "Core 1 β-1,6-N-Acetylglucosaminyltransferase Enzyme Activity is Critical for P-Selectin Glycoprotein Ligand-1 Binding to P-Selectin", Blood, vol. 88, No. 10, pp. 3872-3879 (1996).
Martina Lahmann et al., "A facile approach to diosgenin and furostan type saponins bearing a 3β-chacotriose moiety"., Carbohydrate Research 337 (2002) 2153-2159.
Marion Lanteri et al., "Altered T cell surface glycosylation in HIV-1 infection results in increased susceptibility to galectin-1-induced cell death", Glycobiology vol. 13, No. 12, pp. 909-918 (2003).
Sohpie Lautrette et al., "A new method of solvent free $O$- and N-glycosylation using activated carbon fiber 9ACF) as a promoter. Application to the synthesis of saponin and nucleoside analogues", Chem Commun. (2004) pp. 586-587.
Chuan Li et al., "Synthesis of diosgenyl α-L-rhamnopyransoyl-(1→2)-[β-D-glycopyranosyl-(1→3)] -β-D-glucopyranoside (gracillin) and related saponins", Carbohydrate Research 306 (1998) 189-195.
Ming Li et al., "Synthesis of monomethylated dioscin derivatives and their antitumor activities", Carbohydrate Research 338 (2003) 117-121.

Liu C. et al, Yaoxue Xuebao, (1983) vol. 18, p. 8 pp. 597-606.

Hongwei Liu et al ., "Two new Pregnane Glycosides from *Dioscorea futschauensis* R. Kunth"., Chem. Pharm. Bull. 51(9) 1089-1091 (2003).

Robert W McMurray et al., "Adhesion Molecules in Autoimmune Disease"., Semin. Arthritis and Rheumatism vol. 25, No. 4, Feb. 1996, pp. 215-233.

Yoshihiro Mimaki et al., "Steroidal Saponins from the bulbs of *Lilium regale and L. henryi*"., Phytochemistry, vol. 33 No. 3 pp. 675-682, 1993.

Yoshihiro Mimaki et al., "Steroidal Saponins from the bulbs of *Lilium longiglorum* and their antitumour-promoter activity"., Phytochemistry, vol. 37, No. 1 pp. 227-232 (1994).

Yoshihiro Mimaki et al., "New Steroidal Constituents from the Bulbs of *Lilium candidum*", Chem. Pharm. Bull 46 (11) 1829-1832 (1998).

Yoshihiro Mimaki et al., "Steroidal Saponins from the Rhizomes of *Paris polyphylla* var. *Chinensis* and Their Cytotoxic Activity on HL-60 Cells", Natural Product Letters Vo. 14(5), pp. 357-364.

Daniel Myers, et al., "New and Effective Treatment of Experimentally Induced Venous Thrombosis with Anti-inflammatory rPSGL-Ig", Throm Haemost 2002, 87, 374-82.

Osamu Nakamura, et al., "Steroidal Saponins from the Bulbs of *Lilium speciosum x L. nobilissimum* 'Star Gazer' and their antitumour-promoter activity", Phytochemistry, vol. 36, No. 2, pp. 463-467 (1994).

Kenji Oda et al., "Adjuvant and Haemolytic Activities of 47 Saponins Derived from Medicinal and Food Plants"., Biol. Chem. vol. 381, pp. 67-74, Jan. 2000.

Kazutomo Ori et al., "Jatropham Derivatives and steroidal saponins from the Bulbs of *Lilium hansonII*"., Phytochemistry., vol. 31, No. 8, pp. 2767, 2775, (1992).

Purdie and Irvine., "Synthesis from Glucose of an Octamethylated Disaccharide. Methylation of Sucrose and Maltose", J. Chem. Soc. 87 1022 (11905.

Jean-Hugues Renault et al., "Dammarane Saponins from *Zizyphus lotus*", Phytochemistry vol. 44, No. 7., pp. 1321-1327 (1997).

Emile M. Rijcken et al., "Immunoblockade of PSGL-1 attenuates established experimental murine colitis by reduction of leukocyte rolling", Am J Physiol 287, G115-G124, (2004).

Shengmin Sang et al., "Furostanol saponins from *Allim tuberosum*"., Phytochemistry 52 (1999) pp. 1611-1615.

Serban C Stoica et al., "Endothelial Activation in the Transplanted Human Heart from Organ Retrieval to 3 months after Transplantation: An Observational Study", J. Heart Lung/Transplant., 24(5) 593-601 (2005).

Kurt Hostettmann et al., Saponins (Chemistry and pharmacology of natural products) (1995), Cambridge University Press 1995.

Erich C Strauss et al ., "Soluble P-Selectin Glycoprotein Ligand 1 Inhibits Ocular Inflammation in a Murine Model of Allergy", Invest Ophthalmol/Vis Sci. 40(7); 1336-421 (1999).

Jean-Francois Tanguay et al., "Prevention of in-stent restenosis via reduction of thrombo-inflammatory reactions with recombinant P-selectin glycoprotein ligand-1", thromb Haemost 2004, 91, 1186-93.

Jean-Francois Theoret et al., "P-Selectin Antagomism with Recombinant P-Selection Glycoprotein Ligand-1 (rPSGLIg) Inhibits Circulating Activated Platelet Binding to Neutrophils Induced by Damaged Arterial Surfaces", J. Pharm and Exper. Therap. vol. 298 No. pp. 658-664.

Akihiko Tobari et al, "Spirostanols obtained by cyclization of pseudosaponin derivatives and comparison of anti-platelet agglutination activities of spirostanol glycosides", Eur. J. Med. Chem 35 (2005) 511-527.

M. Tomova et al., "Steroidal Saponins from *Tribulus terrestris* L. with a Stimulating Action on the Sexual Functions", Int. Conf. Chem Biotechnol (1981), 3, 1, 298-302.

I. S Vail'eva et al., "Steroid Saponins from Rhizomes of the Caucasian Yam", Pnkl. Biochim Mikrobiol (1984) 20(3) p. 330-332.

Kai Wang et al., "Recombinant Soluble P-Selectin Glycoprotein Ligand-lg (rPSGL-lg) Attenuates Infarct Size and Myeloperoxidase Activity in a Canine Model of Ischemia-Reperfusion", Thromb Haemost (2002) 88, 149-54.

Shao-Min Wang et al., "Syntheses of acetylated steroid glycosides and selective cleavage of O-acetyl groups in sugar moiety", Steroids 69 (2004) 599-604.

Tadayuki Yago et al., "Structurally Distinct Requirements for Binding of P-selectin Glycoprotein Ligand-1 and Sialyl Lewis x to *Anaplasma phagocytophilum* and P-selectin", J. Biol Chem. (2003) vol. 278, No. 39, 37987-37997.

Deng-Jye Yang et al., "Isolation and Identification of Steroidal Saponins in Taiwanese Yam Cultivar (Dioscorea pseudojaponica Yamamoto", J. Agric. Food Chem. (2003) 51, 6438-6444.

Feng Yin et al., "Dammarane-Type Glycosides from *Gynostemma pentaphyllum*", J. Nat. Prod. (2004) 67 pp. 942-952.

Kazuko Yoshikawa et al., "Antisweet Natural Products. VII. Hodulosides I, II, III, IV and V from the Leaves of *Hovenia dulcis* THUNB", Chem Pharm. Bull. 40(9) 2287-2291 (1992).

Kazuko Yoshikawa et al., "Antisweet Natural Products. VI. Jujubasaponins IV, V and VI from *Zizyphus jujube mill*.", Chem. Pharm. Bull. 40(9) 2275-2278 (1992).

Qing-An Zheng et al., "Steroidal saponins from fresh stem of *Dracaena Cochinchinensis*", Steroids 69 (2004) 111-119.

PCT Notification of Transmittal of the International Search Report and the Written Opinion of the International Searching Authority, or the Declaration, with cited references; International Application No. PCT/GB2004/005398, filed Dec. 22, 2004; Applicant's or agent's file Reference No. 500496WO01; May 31, 2005.

Cheng, M.S., et al; "Total Synthesis of Methyl Protodioscin: A Potent Agent with Antitumor Activity"; *J. Org. Chem.*; vol. 68; pp. 3658-3662 (2003); Citation May 31, 2005; XP-002328851.

Ravikumar, P.R., et al; "Chemistry of Ayurvedic Crude Drugs: Part VI[a] -(Shatavari-1): Structure of Shatavarin-IV[b,c]"; *Indian Journal of Chemistry*; vol. 26B, pp. 1012-1017 (1987); Citation May 31, 2005; XP-001096221.

Toki, D., et al; "Inhibition of UDP-GlcNAc:Galβ1-3GalNAc-R (GlcNAc to GalNAc) β6-N-acetylglucosaminyltransferase from acute myeloid leukaemia cells by photoreactive nitrophenyl substrate derivatives"; *Biochemical and Biphysical Research Communications*; vol. 193, No. 2; pp. 417-423 (1994); Citation May 31, 2005; XP002922997.

Yoshikawa, M., et al; "Medicinal Foodstuffs. VIII.[1] Fenugreek Seed. (2) : Structures of Six New Furostanol Saponins, Trigoneosides IVa, Va, Vb, VI, VIIb, and VIIIb, From the Seeds of Indian *Trigonella Foenum-Graecum L.*"; *Heterocycles*, vol. 47, No. 1; pp. 397-405 (1998); Citation May 31, 2005; XP-001205771.

PCT Notification of Transmittal of the International Search Report and the Written Opinion of the International Searching Authority, or the Declaration, with cited references; International Application No. PCT/GB2006/002301, filed Jun. 22, 2006; Applicant's or agent's file Reference No. 500966WO01 Nov. 15, 2006.

Orlacchio, A., et al; "Activity levels of a β1,6 N-acetylglucosaminyltransferase in lymphomonocytes from multiple sclerosis patients"; *Journal of the Neurological Sciences*; vol. 151; pp. 177-183 (1997); Citation Nov. 15, 2006; XP-002232475.

PCT Notification of Transmittal of the International Search Report and the Written Opinion of the International Searching Authority, or the Declaration, with cited references; International Application No. PCT/GB2006/002500, filed Jul. 6, 2006; Applicant's or agent's file Reference No. 500964WO01 May 25, 2007.

Derwent Publications Ltd., London, GB; AN 2003-664094 & CN 1 415 625 A (Jilin Tianyao Sci & Technology Co. Ltd) May 7, 2003; Citation May 25, 2007; (Abstract) XP-002433233.

Derwent Publications Ltd., London, GB; AN 2001-412294 & JP 2001 072597 A (merican Corp); Mar. 21, 2001; Citation May 25, 2007; (Abstract) XP-002433234.

Derwent Publications Ltd., London, GB; AN 2000-476485 & CN 1 243 129 A (Univ. Shenyang Medicine); Feb. 2, 2000; Citation May 25, 2007; (Abstract) XP-002433235.

Hu, K., et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*, vol. 17, pp. 620-626 (2003); Citation May 25, 2007.

Aquino, R., et al; "Antiviral Activity of Constituents of *Tamus communis*"; *Journal of Chemotherapy*; vol. 3, No. 5; pp. 305-309 (1991); Citation May 25, 2007.

Baek, S.H., et al; "Inactivation of Human Pleural Fluid Phospholipase $A_2$ by Dioscin"; *Arch. Pharm. Res.*; vol. 17, No. 4; pp. 218-222 (1994); Citation May 25, 2007.

Ondeyka, J.G., et al; "Discovery of structurally diverse natural product antagonists of chemokine receptor CXCR3"; *Molecular Diversity*; vol. 9; pp. 123-129 (2005); Citation May 25, 2007.

Sautour, M., et al; "Antifungal steroid saponins from *Dioscorca caycncnsis*. Plant Medica;" *Antimicrobial Activity*; vol. 70(1); pp. 90-92 (2004); Citation May 25, 2007.

PCT Notification of Transmittal of the International Search Report and the Written Opinion of the International Searching Authority, or the Declaration, with cited references; International Application No. PCT/GB2006/002518, filed Jul. 6, 2006; Applicant's or agent's file Reference No. 500965WO01; Dec. 19, 2006.

Derwent Publications Ltd., London, GB; AN 2004-239758; Huang, H., et al; "Medicine composition for treating myocardial ischemia, angina pectoris and cardiac infraction"; & CN 1 465 344 A (Chengdu Diao Pharm Group Co Ltd) Jan. 7, 2004 (Abstract) XP-002409228; Citation Dec. 19, 2006.

Derwent Publications Ltd., London, GB; AN 2005-426073; Wang Jingang; "Dioscin oral disintegration tablet and its preparing method"; & CN 1 586 493 A (Kexinbicheng Medicine Science) Mar. 2, 2005 (Abstract) XP-002409229; Citation Dec. 19, 2006.

Derwent Publications Ltd., London, GB; AN 2002-751531; Zhu Dayuan et al; "Furost saponine analogue and its separatin process and use" & CN 1 184 229 C (Shanghai Inst of Pharmacology) Jan. 12, 2005 (Abstract) XP-002409230; Citation Dec. 19, 2006.

Derwent Publications Ltd., London, GB, AN 2005-631469; Han J. et al; "Medicine for regulating blood fat and treating cardiocerehral disease and preparing method"; & CN 1 615 896 A (Yunnan Prov Medicine Inst) May 18, 2005 (Abstract) XP-002409231; Citation Dec. 19, 2006.

Derwent Publications Ltd., London, GB, AN 2000-443110; Li Pingya et al; "Process for extracting ginsenoside Re, and use of medicine thereof"; & CN 1 242 374 A (Xinliheng Pharmaceutical Scien) Jan. 26, 2000; (Abstract) XP-002409232; Citation Dec. 19, 2006.

Derwent Publications Ltd., London, GB, AN 1998-087548; Junpeng Peng et al; "Anti-thrombosis glucoside medicine"; & CN 1 138 984 A (Radiomedicine Inst Military ME) Jan. 1, 1997; (Abstract) XP-002409233; Citation Dec. 19, 2006.

Derwent Publications Ltd., London, GB, AN 2006-272298; Fu T., et al; "Steroidal saponin pharmaceutical composition, its preparation method and use"; & WO 2006/034655 A (chengdu Diao Pharm Group Co Ltd) Apr. 6, 2006 (Abstract) XP-002409234; Citation Dec. 19, 2006.

Zhang, J., et al; "Effect of six steroidal saponins isolated from anemarrhenae rhizome on platelet aggregation and hemolysis in human blood"; *Clinica Chimica Acta*; vol. 289; pp. 79-88 (1999); Citation Dec. 19, 2006.

Molham Al-Habori et al "Pharmacological properties"; Fenugreek The genus Trigonella Edited by Georgios A. Petropoulos, pp. 162-182.

N M Ammar et al "Study of the anti-inflammatory activity of some medicinal edible plants growing in Egypt", Journal of Islamic Academy of Sciences 10:4, 113-122.

Droogan A G et al "Serum and cerebrospinal fluid levels of soluble adhesion molecules in multiple sclerosis: predominant intrathecal release of vascular cell adhesion molecule-1"; Journal of Neuroimmunology 64 (1996) 185-191.

Shinya Hanashima et al "Systematic Synthesis of Bisubstrate-Type Inhibitors of *N*-Acetylglucosaminyltransferases" Chem. Eur. J. 2006, 12, 3449-3462.

Mohamed S Kamel et al, "Studies on Balanites aegyptiaca Fruits, an Antidiabetic Egyptian Folk Medicine"; Chemical & Pharmaceutica Bulletin 1991, 39(5), 1229-1233.

Takao Konoshima et al "Anti-Aids Agents, 21 Triterpenoid saponins as anti-HIV principles from fruits of gleditsia Japonica and gymnocladus chinesis and a structure-activity correlation"; Journ of Nat. Prods. vol. 58, No. 9, pp. 1372-1377, Sep. 1995.

Laurence A Lasky, "Selectin-Carbohydrate interactions and the initiation of the inflammatory response", Annual Review of Biochemistry 1995 vol. 64, pp. 113-139.

Daniel Lazarevia et al; "Artificial *N*-functionalised UDP-glucosamine analogues as modified substrates for *N*-acetylglycosaminyl transferases" Carbohydrate Research 2006, vol. 341(5), 569-576.

Hiromichi Matsuura; "Saponins in Garlic as Modifiers of the Risk of Cardiovascular Disease"; Journal of Nutrition 131, 1000S-1005S, 2001.

John G Ondeyka et al; "Discovery of structurally diverse natural product antagonists of chemokine receptor CXCR3"; Molecular Diversity (2005), 9, 123-129.

Carlo A Palmerini et al "An approach for fluoremetric determination of glycosyltransferase activities", Glycoconjugate Journal (1996) 13, 631-636.

Helen Skaltsa, "Chemical Constituents" , Fenugreek The genus *Trigonella* Edited by Georgios A. Petropoulos, pp. 132-161.

M M Vaghefi et al; "Synthesis of Glycopyranosylphosphonate Analogues of Certain Natural Nucleoside Diphosphate Sugars as Potential Inhibitors of Glycosyltransferases", Journal of Medicinal Chemistry, 1987, (30), 1383-1391.

M M Vaghefi et al, "Synthesis of certain nucleoside methylenediphosphonate sugars as potential INHIB", Journal of Medicinal Chemistry 1987, 30 1391-1399.

Co-pending CIP U.S. Appl. No. 11/980,727, filed Oct. 31, 2007.

L. S. Akhov et al.2000, Biological Activity of Deltoside from *Allium nutans* L. in *Saponins in Food*, Feedstuffs and Medicinal Plants edited by W Oleszek and A Marston.

Bernadete P. da Silva, et al, A New Bioactive Steroidal Saponin from *Agave attenuata*; Z. Naturforsch, 57c, 423-428 (2002).

Mei Dong et al, Two New Steroidal Saponins from the Rhizomes of *Dioscorea panthaica* and their Cytotoxic Activity; Planta Med. 67 (2001) 853-857.

M. Dong et al, Steroidal saponins from *Dioscorea panthaica* and their cytotoxic activity; Pharmazie 59, 294-296 (2004).

B. B. Gaitonde et al; Antioxytocic action of Saponin isolated from Asparagus Racemosus Willd (Shatavari) on Uterine Muscle; Arch. int. Pharmacodyn., 1969, 179, No. 121-129.

Antonio G. Gonzalez et al; Steroidal Saponins from the Bark of *Dracaena draco* and Their Cytotoxic Activities; J. Nat. Prod. 2003, 66, 793-798.

Juan C. Hernandez et al, Icogenin, a new cytotoxic steroidal saponin isolated from *Dracaena draco*; Bioorganic & Medicinal Chemistry 12 (2004) 4423-4429.

Hiroschige Hibasami et al, Protodioscin isolated from fenugreek (*Trigonella foenumgraecum* L). induces cell death and morphological change indicative of apoptosis in leukemic cell line H-60, but not in gastric cancer cell line KATO III; International Journal of Molecular Medicine 11: 23-26, 2003.

Ke Hu et al; Methyl protogracillin (NSC-698792): the spectrum of cytotoxicity against 60 human cancer cell lines in the National Cancer Institute's anticancer drug screen panel, Anti-Cancer Drugs 2001, 12, pp. 541-547.

Sung Yong Kim et al; Inhibition of Mouse Ear Edema by Steroidal and Triterpenoid Saponins: Arch Pharm Res, vol. 22, No. 3, 313-316, 1999.

M. A. Lacaille-Dubois et al; A review of the biological and pharmacological activities of saponins: Phytomedicine vol. 2(4), pp. 363-386, 1996.

H.W. Liu et al; Bioactive saponins from *Dioscorea futschauensis*: Pharmazie 57 (2002) 8 570-572.

Hisashi Matsuda et al; Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action: Bioorganic & Medicinal Chemistry Letters 13 (2003) 1101-1106.

Yoshihiro Mimaki et al; Steroidal Saponins from the bulbs of *Triteleia lactea and their inhibitory activity on cyclic amp phosphodiesterase*: Phytochemistry, vol. 38, No. 5, pp. 1279-1286, 1995.

Yoshihiro Mimaki et al; Cytotoxic Activities and Structure-Cytotoxic Relationships of Steroidal Saponins: Biol. Pharm. Bull, 24(II) 1286-1289 (2001).

Pierre R Petit et al; Steroid saponins from fenugreek seeds: Extraction, purification, and pharmacological investigation on feeding behaviour and plasma cholesterol: Steroids, 60: 674-680, 1995.

P. Sur et al; Short Communication *Trigonella foenum graecum* (Fenugreek) Seed Extract as an Antineoplastic Agent: Phytotherapy Research, 15, 257-259 (2001).

Yi-Fei Wang et al; Inhibitory Effects of Some Steroidal Saponins on Human Spermatozoa in vitro: Planta Medica 62 (1996) 130-132.

Ethan Basch et al; Therapeutic Applications of Fenugreek: Alternative Medicine Review vol. 8, No. 1, 2003 pp. 20-27.

Dinesh Puri; Therapeutic Potentials of Fenugreek: Indian J Physiol Pharmacol. 1998; 42(3) pp. 423-424.

L. S. Akhov et al Structure of Steroidal Saponins from Underground Parts of *Allium nutans* L.; J. Agric. Food Chem. 1999, 47, 3193-3196.

Paul V. Beaum et al; Expression of Core 2 β-1,6-N-Acetylglucosaminyltransferase in a Human Pancreatic Cancer Cell Line Results in Altered Expression of MUC1 Tumor-associated Epitopes; The Journal of Biological Chemistry, vol. 274, No. 35, Issue of Aug. 27, pp. 24641-24648, 1999.

Christopher Boca et al; 4-Hydroxyisoleucine: effects of synthetic and natural analogues on insulin secretion; European Journal of Pharmacology 390 (2000) 339-345.

I. Brockhausen et al; Biosynthesis of *O*-Glycans in Leukocytes from Normal Donors and from Patients with Leukemia: Increase in *O*-Glycan Core 2 UDP-GlcNAc:Galβ3GalNAcα-R(GlcNAc to GalNAc)β(1-6)-N-Acetylglucosaminyltransferase in Leukemic Cells; Cancer Research 51, 1257-1263, Feb. 15, 1991.

Mao S. Cheng et al; Total Synthesis of Methyl Protodioscin: A Potent Agent with Antitumor Activity; J.Org.Chem. 2003, 68, 3658-3662.

Rakesh Chibber et al; Activity of the Glycosylating Enzyme, Core 2 GlcNAc (β1,6) Transferase, Is Higher in Polymorphonuclear Leukocytes from Diabetic Patients Compared with Age-Matched Control Subjects; Diabetes, vol, 49, Oct. 2000, pp. 1724-1730.

Karen J. Colley; Golgi localization of glycosyltransferases: more questions than answers; Glycobiology vol. 7, No. 1 pp. 1-13, 1997.

Martin Dalziel et al; The Relative Activities of the C2GnT1 and ST3Gal-I Glycosyltransferases Determine *O*-Glycan Structure and Expression of a Tumor-associated Epitope on MUCI; The Journal of Biological Chemistry Vo. 276, No. 14, Issue of Apr. 6, pp. 11007-11015, 2001.

Matthew D. Davis et al, Diabetic Retinopathy; Diabetes Care, vol. 15, No. 12, Dec. 1992, pp. 1844-1874.

Michael J. Davies et al; The expression of the adhesion molecules ICAM-1, VCAM-1, PECAM, and E-Selectin in Human Atherosclerosis; Journal of Pathology, vol. 171, 223-229 (1993).

Shaojiang Deng et al; Synthesis of three diosgenyl saponins: dioscin, polyphyllin D, and balanitin 7; Carbohydrate Research 317 (1999) 53-62.

Yuguo Du et al; Synthesis of Saponins Using Partially Protected Glycosyl Donors; Organic Letters 2003, vol. 5, No. 20, 3627-3630.

Lesley G. Ellies et al; Core 2 Oligosaccharide Biosynthesis Distinguishes between Selectin Ligands Essential for Leukocyte Homing and Inflammation; Immunity, vol. 9, 881-890, Dec. 1998.

Umit Guray et al; Levels of Soluble adhesion molecules in various clinical presentations of coronary atherosclerosis; International Journal of Cardiology 96 (2004) 235-240.

Umit Guray et al; Poor coronary collateral circulation is associated with higher concentrations of soluble adhesion colecules in patients with single-vessel desease; Coronary Artery Disease 2004, 15: 413-417.

Elizabeth A. Higgins et al; Aberrant *O*-Linked Oligosaccharide Biosynthesis in Lymphocytes and Platelets from Patients with the Wiskott-Aldrich Syndrome; The Journal of Biological hemistry: vol. 266, No. 10 Issue of Apr. 5, pp. 6280-6290.

Jayshree Joshi et al; Chemistry of Ayurvedic Crude Drugs: Part VIII—Shatavari-2: Structure Elucidation of Bioactive Shatavarin-I & other Glycosides: Indian Journal of Chemistry, vol. 27B, Jan. 1988, pp. 12-16.

Ronald Klein et al; The Wisconsin Epidemiologic Study of Diabetic Retinopathy: X. Four-Year Incidence and Progression of Diabetic Retinopathy When Age at Diagnosis is 30 years or More; Arch Ophthalmol 1989; 107: 244-249.

Eva M. Kohner et al; Diabetic Retinopathy in Diabetic Angiopathy, Tooke J.E., pp. 233-247, Oxford University Press (1999).

Daisuke Koya et al; Perspectives in Diabetes: Protein Kinase C Actibvation and the Development of Diabetic Complications; Diabetes, vol. 47, 859-866, 1998.

Diasuke Koy et al; Overexpression of core 2, N-acetylglycosaminyltransferase enhances cytokine actions and induces hypertrophic myocardium in transgenic mice: FASEB J. 13, 2329-2337 (1999).

William Kuhns et al; Procession *O*-glycan core 1, Galβ1-3GalNAcα-R, Specificities of core 2, UDP-GLcNAc: Galβ1-3GalNAc-R(GLcNAc to GalNAc)β6-*N*-acetylglycosaminyltransferase and CMP-sialic acid: Galβ1-3GalNAc-R α3-sialyltransferase: Glycoconjugate Journal (1993) 10 : 381-394.

Kensuke Kumamoto et at; Specific Detection of Sialyl Lewis X Determinant Caried on the Mucin GlcNAcβ1→6GalNAcα Core Structure as a Tumor-Associated Antigen; Biochemical and Biophysical Research Communications 247, 514-517 (1998).

Suzanne Laferte et al; Glycosylation-dependent Collagen-binding Activities of Two Membrane Glycoproteins in MDAY-D2 Tumor Cells: Cancer Research 48, 4743-4748, Sep. 1, 1988.

Chuan Li, et al; Synthesis of Diosgenyl α-L-rhamnopyranosyl-(1→2)—[β-D-glucopyranosyl-(1→3)]-β-D-glucopyranoside (gracillin) and related saponins; Carbohydrate Research 306 (1998) 189-195.

Bing Li et al; An improved synthesis of the saponin, polyphyllin D; Carbohydrate Research 331 (2001) 1-7.

Emi Machida et al; Clinicopathological Significance of Core 2 β,6-*N*-Acetylglucosaminyltransferase Messenger RNA Expressed in the Pulmonary Adenocarcinoma Determined by in situ hybridization; Cancer Research 61, 2226-2231, Mar. 1, 2001.

Kentaro Maemura et al; Poly-*N*-acetyllactosaminyl *O*-Glycans attached to Leukosialin; The Journal of Biological Chemistry, vol. 267, No. 34, Issue of Dec. 5th, pp. 24379-24386.

Marja-Leena Majuri et al; Recombinant E-selectin-protein mediates tumor cell adhesion via sialyl-Lea and sialyl-Lex; Biochemical and Biophysical Research Communications, vol. 182, No. 3 1992, Feb. 14, 1992, pp. 1376-1382.

Matthias Meier et al; Protein kinase C activation and its pharmacological inhibition in vascular disease; Vascular Medicine 2000; 5: 173-185.

Yoshihiro Mimaki et al; Steroidal Saponins and Alkaloids from the Bulbs of *Lilium brownie* var. *colchesteri*; Chem. Pharm. Bull 38(11) 3055-3059 (1990).

N T Mulvihill et al ; Inflammation in acute coronary syndromes; Heart 2002, 87, 201-204.

Toshiyuki Murakami et al; Medicinal Foostuffs. XVII. Fenugreek Seed. (3): Structures of New Furostanol-Type Steroids Saponins, Trigoneosides Xa, Xb, XIb, XIIa, XIIb, and XIIIa, from the Seeds of Egyptian *Trigonella Foenum-graecum* L; Chem. Pharma. Bull. 48(7)1994-1000 (2000).

Mitsuru Nakamura et al; Simultaneous core 2 β1→6*N*-acetylglycosaminyltransferase up-regulation and sialyl-Le expression during activation of human tonsillar B lymphocytes; FEBS Letters 463 (1999) 125-128.

Yoshihiko Nishio et al; Identification and Characterization of a Gene Regulating Enzymatic Glycosylation which is Induced by Diabetes and Hyperglycemia Specifically in Rat Cardiac Tissue; J. Clin. Invest. vol. 96, Oct. 1995, 1759-1767.

Kevin D O'Brien et al; Neovascular Expression of E-Selectin, Intercellular Adhesion Molecule-1, and Vascular Cell Adhesion Molecule-1 in Human Atherosclerosis and Their Relation to Intimal Leukocyte Content; 1996 American Heart Association, In.c. 1996; 93: 672-682.

Katsuyuki Ohmori et al; A Distinct Type of Sialyl Lewis X Antigen Defined by a Novel Monoclonal Antibody is Selectively Expressed on Helper Memory T Cells; Blood, vol. 82, No. 9 (Nov. 1, 1993) pp. 2797-2805.

Hans Paulsen et al; Synthese von modifizierten Derivaten des Disaccharides β-D-Gal-(1→3)-α-D-GalNAc zur Untersuchung der Substratspezifitat der Core-2-β6-GlcNAc-Transferase and α-3-Sialyltransferase der Biosynthese von O-Glycoproteinen: Liebigs Ann. Chem. 1992, 747-758.

George R Pettit et al: Isolation and Structure of Cytostatic Steroidal Saponins from the African Medicanal Plant *Balanites Aegyptica*; Journal of Natural Products Vo. 54, No. 6 pp. 1491-1502 Nov.-Dec. 1991.

Friedrich Piller et al; Human T-lymphocyte Activation is Associated with changes in O-Glycam Biosynthesis; The Journal of Biological Chemistry, vol. 263, No. 29, Issue of Oct. 15, pp. 15146-15150, 1988.

Jutta Renkonen et al; Core 2 β1,6-N-acetylglycosaminyltransferases and α1,3-fucosyltransferases regulate the synthesis of O-glycans on selectin ligands on oral cavity carcinoma cells; APMIS 109, 500-6, 2001.

P. R. Ravikumar et al; Chemistry of Ayurvedic Crude Drugs: Part VI-(Shatavari-1):Structure of Shatavarin-IV; Indian Journal of Chemistry vol. 26B, Nov. 1987, pp. 1012-1017.

Osamu Saitoh et al; Expression of Aberrant O-Glycans attached to Leukosialin in Differentiation-deficient HL-60 Cells; Cancer Research 51, 2854-2862, Jun. 1, 1991.

Yutaka Sashida et al; Studies on the Chemical Constituents of the Bulbs of *Lilium mackliniae*; Chem. Pharm. Bull. 39(9) 2362-2368 (1991).

Yves Sauvaire et al; 4-Hydroxyisoleucine. A novel amino acid potentiator of insulin secretion; Diabetes, vol. 47, Feb. 1998 pp. 206-210.

S C Sharma et al; Oligofurostanosides from *Asparagus curillus leaves*; Phytochemistry, Vo. 33, No. 3, pp. 683-686, 1993.

R D Sharma et al; Effect of fenugreek seeds on blood glucose and serum lipds in Tyupe 1 diabetes; European Journal of Clinical Nutrition (1990) 44, 301-306.

Kazuhisa Shimodaira et al; Carcinoma-associated Expression of Core 2 β-1,6-N-Acetylglucosaminyltransferase Gene in Human Colorectal Cancer: Role of O-Glycans in Tumor Progression; Cancer Research 57, 5201-5206 Dec. 1, 1997.

Hiroko Shimomura et al; Steroidal Saponins, PardarinosideA-G from the Bulbs of *Lilium pardarinum*; Phytochemistry, Vo. 28, No. 11 pp. 3163-3170, 1989.

Markus Sperandio et al; Severe impairment of leukocyt, rolling in venules of core 2 glyucosaminyltransferase-deficient mice; Blood, Jun. 15, 2001, vol. 97. No. 12, pp. 3812-3819.

Akiko Takada et al; Contribution of Carbohydrate Antigens Sialyl Lewis A and Sialyl Lewis X to Adhesion of Human Cancer Cells to Vascular Endothelium; Cancer Research 53, 354-361, Jan. 15, 1991.

Shigeru Tsuboi et al; Branched O-linked oligosaccharides ectopically expressed in transgenic mice reduce primary T-cell immune responses; The EMBO Journal vol. 16, No. 21, pp. 6364-6373, 1997.

Shigeru Tsuboi et al; Overexpression of Branched O-Linked Oligosaccharides on T Cell Surface Glycoproteins Impairs Humoral Immune Responses in Transgenic Mice; The Journal of Biological Chemistry Vo. 273, No. 46, Issue of Nov. 13, 1988 pp. 30680-30687.

Shigeru Tsuboi et al; Roles of O-linked oligosaccharides in immune responses; BioEssays 23:46-53, 2001.

Ajit Varki; Special Invited Review: Biological roles of oligosaccharides: all of the theories are correct; Glycobiology Vo. 3, No. 2 pp. 97-130, 1993.

I.S.Vasil'eva et al; Composition and Biological Activity of Steroid Glycosides from Cell Suspensions of *Discorea deltoidea* Wall; Applied Biochemistry and Microbiology, vol. 31, No. 2, 1995 pp. 206-209.

Gerd Walz et al; Recognition by ELAM-1 of the Sialyl-Le Determinant on Myeloid and Tumor Cells; Science, vol. 250 pp. 1132-1135, 1990.

Patricia P Wilkins et al; Structures of the O-Glycans on P-selectin Glycoprotein Ligand-1 from HL-60 Cells; The Journal of Biological Chemistry, vol. 271, No. 31, Issue of Aug. 2, 1996 pp. 18732-18742.

David Williams et al; Detection in Canine Submaxillary glands of an N-Acetylglucosaminyltransferase which acts on mucin substrates; The Journal of Biological Chemistry, vol. 255, No. 23, Issue of Dec. 10, 1980 pp. 11247-11252.

Masayuki Yoshikawa et al; Medicinal Foodstuffs IV. Fenugreek Seed. (1): Structures of Trigoneosides Ia, Ib, IIa, IIb, IIIa and IIIb, New Furostanol Saponins from the Seeds of Indian *Trigonella Foenum-graecum* L; Chem. Pharm. Bull. 45(1) 81-87 (1997).

Masayuki Yoshikawa et al; Medicinal Foodstuffs, VIII. Fenugreek Seed (2): Structures of six new Furostanol Saponins Trigoneosides IVa, Va, Vb, VI, VIIb, and VIIIb, from the Seeds of Indian *Trigonella Foenum-graecum L.*; Heterocycles, vol. 47, No. 1, 1998, pp. 397-405.

Shida Yousefi et al; Increased UDP-GlcNAc:Galβ1-3GalNAc-R (GlcNAc to GalNAc) β-1, 6-N-Acetylglucosaminyltransferase Activity in Metastatic Murine Tumor Cell Lines; The Journal of Biological Chemistry, vol. 266, No. 3, Issue of Jan. 25, 1991 pp. 1772-1782.

Biao Yu, A "Double Random" Strategy for the Preparation of Saponin Libraries; J. Comb. Chem. 2001, 3, 404-406.

Biao Yu et al; The first synthetic route to furostan saponins; Tetrahedron Letters 42 (2001) pp. 77-79.

Biao Yu, et al; Glycosyl Trifluoroacetimidates.2. Synthesis of Dioscin and Xiebai Saponin 1; J. Org Chem. 2002, 67, 9099-9102.

Robert A Moreau et al; Phytosterols, phytostanols, and their conjugates in Foods: structural diversity, quantitative analysis, and health-promoting uses; Progress in Lipd Research 41, (2002) 457-500.

Hostettmann, K. et al; Chemistry and pharmacology of natural products; Saponins Cambridge University Press (1995) (extracted book pages).

Co-Pending U.S. Appl. No. 11/472,554, filed Jun. 22, 2006.
Co-Pending U.S. Appl. No. 11/481,255, filed Jul. 6, 2006.
Co-Pending U.S. Appl. No. 11/481,256, filed Jul. 6, 2006.

Chibber, R., et al; "Activity of the Glycosylating Enzyme, Core 2 GlcNAc (β1,6) Transferase, is Higher in Polymorphonuclear Leukocytes From Diabetic Patients Compared With Age-Matched Control Subjects"; *Diabetes*; vol. 49; pp. 1724-1730 (2000).

Chibber, R., et al; "Protein Kinase C β2-Dependent Phosphorylation of Core 2 GlcNAc-T Promotes Leukocyte-Endothelial Cell Adhesion"; *Diabetes*; vol. 52; pp. 1519-1527 (2003).

Ellies, L.G., et al; "Core 2 Oligosaccharide Biosynthesis Distingjishes between Selectin Ligands Essential for Leukocyte Homing and Inflammation"; *Immunity*; vol. 9, pp. 881-890 (1998).

Goekjian, P.G., et al; "Protein kinase C inhibitors as novel anticancer drugs"; *Expert Opin. Investig. Drugs*; vol. 10, No. 12; pp. 2117-2140 (2001).

Hartung, Hans-Peter, MD; et al; "Circulating Adhesion Molecules and Tumor Necrosis Factor Receptor in Multiple Sclerosis: Correlation with Magnetic Resonance Imaging"; *Annals of Neurology*; vol. 38, No. 2; pp. 186-193 (1995).

Hindsgaul, O., et al; "Evaluation of Deoxygenated Oligosaccharide Acceptor Analogs as Specific Inhibitors of Glycosyltransferases"; *The Journal of Biological Chemistry*; vol. 266, No. 27; pp. 17858-17862 (1991).

Joshi, J., et al; "Chemistry of Ayurvedic Crude Drugs: Part VIII[a]-Shatavari-2: Structure Elucidation of Bioactive Shatavarin-I & other Glycosides[b,c]"; *Indian Journal of Chemistry*; vol. 27B; pp. 12-16 (1988).

Kim, S.Y., et al; "Inhibition of Mouse Ear Edema by Steroidal and Triterpenoid Saponins"; *Arch Pharm Res.*; vol. 22, No. 3, pp. 313-316 (1999).

Kuhns, W., et al; "Processing O-glycan core 1, Galβ1-3GalNAcα-R. Specificities of core 2, UDP-GlcNAc: Galβ1-3GalNAc-R(GlcNAc to GalNAc) β6-N-acetylglucosaminyltransferase and CMP-sialic acid: Galβ1-3GalNAc-R α3-sialyltransferase"; *Glycoconjugate Journal*; vol. 10; pp. 381-394 (1993).

Matsuda, H., et al; "Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action"; *Bioorganic & Medicinal Chemistry Letters*; vol. 13; pp. 1101-1106 (2003).

Orlacchio, A., et al; "Activity levels of a β1, 6 N-acetylglucosaminyltransferase in lymphomonocytes from multiple sclerosis patients"; *Journal of Neurological Sciences*; vol. 151; pp. 177-183 (1997).

Toki, D., et al; "Inhibition of UDP-GlcNAc:Galβ1-3GalNAc-R (GlcNAc to GalNAc) β6-N-acetylglucosaminyltransferase from acute myeloid leukaemia cells by photoreactive nitrophenyl substrate derivatives"; *Biochemical and Biophysical Research Communications*; vol. 198, No. 2; pp. 417-423 (1994).

Washington, R., et al; "Expression of Immunologically Relevant Endothelial Cell Activation Antigens on Isolated Central Nervous System Microvessels from Patients with Multiple Sclerosis"; *Ann. Neurol*; vol. 35, No. 1; pp. 89-97 (1994).

Li, Cheng-Ming, et al; "Development of monoclonal antibodies against bovine mucin core 2 β6 N-acetylglucosaminyltransferase"; *Glycoconjugate Journal*; vol. 16; pp. 555-562 (1999).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Yu, Jing et al, "Progress in studies on chemical constituents and pharmacological effect of *Trigonella foenum-graecum*"; *Chinese Traditional and Herbal Drugs*, vol. 34, (12) 1146-1149 (2003).

Derwent Publications Ltd., London, GB AN 2001/412294 & JP 2001 072597 A (Mercian) Corp; Mar. 21, 2001; (abstract).

Battistini, L. et al; "CD8+ T cells from patients with acute multiple sclerosis display selective increase of adhesiveness in brain venules: a critical role for P-selectin glycoprotein ligand-1", *Blood*, vol. 101 No. 12, 4775-4780 (2003).

Ben-Mahmud, Bahaedin M., et al; "Tumor Necrosis Factor-α in Diabetic Plasma Increases the Activity of Core 2 GLcNAc-T and Adherence of Human Leukocytes to Retinal Endothelial Cells"; *Diabetes*, vol. 53, 2968-2976 (2004).

Brockhausen, I., et al; "Biosynthesis of O-Glycans in Leukocytes from Normal Donors and from Patients with Leukemia: Increase in O-Glycan Core 2 UDP-GlcNAc:Galβ1-3GalNAc-R (GlcNAc to GalNAc) β1(1-6)-N-Acetylglucosaminyltransferase in Leukemic Cells"; *Cancer Research*; 51, 1257-1263 (1991).

Buerke, Michael, et al; "Sialyl Lewis$^x$—Containing Oligosaccharide Attenuates Myocardial Reperfusion Injury in Cats"; *J. Clin. Invest.*; vol. 93, 1140-1148 (1994).

Beum, P.V. and Cheng, Pi-W.; "Biosynthesis and Function of β1,6 Branched Mucin-Type Glycans"; *The Molecular Immunology of Complex Carbohydrates-2* (2001).

Beum, P.V., et al; "Mucin biosynthesis: upregulation of core 2 β1,6 N-acetylglucosaminyltransferase by retinoic acid and Th2 cytokines in a human airway epithelial cell line"; *Am J. Physiol Lung Cell Mol Physiol.*; 288: L116-L124 (2005).

Beum, P.V., et al; "Mucin Biosynthesis Epidermal Growth Factor Downregulates Core 2 Enzymes in a Human Airway Adenocarcinoma Cell Line"; *Am. J. Respir. Cell Mol. Biol.*; vol. 29, 48-56 (2003).

Celie, J.W.A.M., et al; "Identification of L-Selectin Binding Heparan Sulfates Attached to Collagen Type XVIII"; *J Biol Chem.*; 280(29); 26965-73; Epub (2005).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Dennis, James W.; "Glyco-Forum Section; Core 2 GlcNAc-Transferase and polylactosamine expression in *O*-glycans", *Glycobiology*; vol. 3, No. 2, pp. 91-96 (1993).

Dube, Danielle H. et al, "Glycans in Cancer and Inflammation—Potential for Therapeutics and Diagnostics", *Nature Reviews*, vol. 4, No. 6, 477-288 (2005).

Duan L-L. et al; "Regulation of Metastasis-Suppressive Gene Nm23-H1 on Glycosy-transferases Involved in the Synthesis of Sialy Lewis Antigens"; *J. Cell. Biochem.*; 94:1248-1257 (2005).

Fox, R.I., et al; "A Novel Cell Surface Antigen (T305) Found in Increased Fequency on Acute Leukemia Cells and in Autommune Disease States"; *J. Immunol.* vol. 131, No. 2, 761-767 (1983).

Foxall, C. et al; "The Three Members of the Selectin Receptor Family Recognize a Common Carbohydrate Epitope, the Sialyl Lewis$^x$Oligosaccharide"; *J. Cell Biol.*; vol. 117, 895-902 (1992).

Fugang P. et al; "Post Translational Modifications of Recombinant P-selectin Glycoprotein Ligand-1 Required for Binding to P and E-selectin"; *J. Biol. Chem.*; vol. 271, No. 6, 3255-3264 (1996).

Fujita, M. et al; "Pulmonary hypertension in TNF-α-overexpressing mice is associated with decreased VEGF gene expression"; *J. Applied Physiol*; vol. 93, 2162-2170 (2002).

Goss, P. E. et al; "Inhibitors of Carbohydrate Processing: A New Class of Anticancer Agents[1,2]"; *Clin. Cancer Res.*; vol. 1, 935-944 (1995).

Maaheimo, Hannu et al, "Synthesis of a divalent sialyl Lewis x O-glycan, a potent inhibitor of lymphocyte-endothelium adhesion"; *Eur. J. Biochem*; 234, 616-625 (1995).

Hiraoka, N. et al; "Core 2 Branching β1,6-N-Acetylglucosaminyltransferase and High Endothelial Venule-restricted Sulfotransferase Collaboratively Control Lymphocyte Homing"; *J. Biol Chem.*; vol. 279, No. 4, 3058-3067 (2004).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Kumar, A. et al; "Recombinant Soluble Form of PSGL-1 Accelerates Thrombolysis and Prevents reocclusion in a Porcine Model"; *Circulation*; 99, 1363-1369 (1999).

Jain, Rakesh K. et al, "Inhibition of L-and P-selectin by a rationally synthesized novel core 2-like branched structure containing GalNAc-Lewis$^x$ and Neu5Acα2-3Galβ1-3GalNAc sequences"; *Glycobiology*, vol. 8, No. 7; 707-717 (1998).

Jones, Steven P., "A Bittersweet Modification *O*-GlcNAc and Cardiac Dysfunction"; *Circ Res.*; 96; 925-926 (2005).

Kamisako, Toshinori et al, "Regulation of biliary cholesterol secretion is associated with abcg5 and abcg8 expressions in the rats: effects of diosgenin and ethinyl estradiol", *Hepatology Research* 26; 348-352 (2003).

Lewis, M.J. and D'Cruz D.; "Adhesion molecules, mycophenolate mofetil and systemic lupus erythematosus"; *Lupus*, 14, 17-26 (2005).

Martininez, M. et al; "Regulation of PSGL-1 Interactions with L-selectin, P-selectin, and E-selectin"; *J. Biol. Chem.*, vol. 280, No. 7, 5378-5390 (2005.).

Merzaban, Jasmeen S. et al.; "An Alternate Core 2 β,6-N-Acetylglucosaminyltransferase Selectively Contributes to P-Selectin Ligand Formation in Activated CD8 T Cells[1]"; *The Journal of Immunology*, 174: 4051-4059 (2005).

Morin, M.J. and Bernacki, R.J.; "Biochemical Effects and Therapeutic Potential of Tunicamycin in Murine L1210 Leukemia"; *Cancer Res*. 43, 1669-1674 (1983).

Nakamura, M. et al.; "Single Glycosyltransferase, Core 2β1-6-N-acetylglucosaminyltransferase, Regulates Cell Surface Sialy-Le$^x$ Expression Level in Human Pre-B Lymphocytic Leukemia Cell Line KM3 Treated with Phorbolester"; *J. Biol. Chem.*; 273, No. 41; 26779-26789 (1998).

Narumi, S. et al; "Tissue-Specific Induction of E-Selectin in Glomeruli is Augmented following Diabetes mellitus"; *Nephron*; 89, 161-171 (2000).

Okada, S. et al; "Intercellular Adhesion Molecule-1—Deficient Mice are Resistant Against Renal Injury After Induction of Diabetes"; *Diabetes*; 52:2586-2593 (2003).

Piccio L. et al; "Molecular Mechanisms Involved in Lymphocyte Recruitment in Inflamed Brain Microvessels: Critical Roles for P-Selectin Glycoprotein Ligand-1 and Heterotrimeric G$_i$-Linked Receptors[1]"; *J. Immunol.*; 168: 1940-1949 (2002).

Ravnskov, U.; "Is atherosclerosis caused by high cholesterol?", *Q J Med*; 95, 397-403 (2002).

Ross, Russell; "Atherosclerosis—An Inflammatory Disease", *The New England Journal of Medicine*, vol. 340, 2, 115-126 (1999).

Simmons, Rex D. and Brenda A. Cattle; "Sialyl Ligands facilitate lymphocyte accumulation during inflammation of the central nervous system", *Journal of Neuroimmunology*, 41; 123-130 (1992).

Steinberg, D.; "Atherogenesis in perspective: Hypercholesterolemia and inflammation as partners in crime"; *Nature Medicine*; vol. 8, No. 11; 1211-1217 (2002).

Steinman, Lawrence; "Blocking Adhesion Molecules as Therapy for Multiple Sclerosis: Natalizumab"; *Nature Reviews: Drug Discovery*, vol. 4, 510-518 (2005).

Baek, Suk Hwan, et al, "Inactivation of Human Pleural Fluid Phospholipase A$_2$ by Dioscin"; *Arch. Pharm. Res.*; vol. 17, No. 4, 218-222 (1994).

Ulbrich, Holger, et al; "Leukocyte and endothelial cell adhesion molecules as targets for therapeutic interventions in inflammatory disease"; *Trends in Pharmacological Sciences*, vol. 24, No. 12; 640-647 (2003).

Williams, D. et al; "Mucin Synthesis II. Substrate Specificity and Product Identification Studies on Canine Submaxillary Gland UDP-GlcNAc: Galβ1-3GalNAc(GlcNAc-GalNAc) β6-N-acetylglucosaminyltransferase"; *J. Biol. Chem.*; 255, No. 23; 1253-1261 (1980).

Yanagihara, K., et al; "Lipopolysaccharide Induces Mucus Cell Metaplasia in Mouse Lung"; *Am. J. Respir. Cell Mol. Biol.*; 24, 66-73 (2001).

Yu, Jing et al, "Progress in studies on chemical constituents and pharmacological effect of *Trigonella foenum-graecum*"; *Chinese Traditional and Herbal Drugs*, vol. 34, (12) 1146-1149 (2003).

Zak, I., et al; "Selectin Glycoprotein Ligands"; *Acta Biochemica Polonica*; vol. 47, No. 2; 393-412 (2000).

Confavreux, C., et al; "Age at disability milestones in multiple sclerosis"; *Brain*; vol. 129; pp. 595-605 (2006).

Confavreux, C., et al; "Natural history of multiple sclerosis: a unifying concept"; *Brain*, vol. 129; pp. 606-616 (2006).

Elovaara, I., et al; "Adhesion Molecules in Multiple Sclerosis"; *Arch Neurol*; vol. 57, pp. 546-551 (2000).

McDonnell, G.V., et al; "Serum soluble adhesion molecules in multiple sclerosis: raised sVCAM-1, sICAM-1 and sE-selectin in primary progressive disease"; *J. Neurol*; vol. 246; pp. 87-92 (1999).

Musso, A.M., et al; "Increased serum levels of ICAM-1, ELAM-1 and TNF-α in inflammatory disorders of the peripheral nervous system"; *Ital. J. Neurol. Sci.*; vol. 15; pp. 267-271 (1994).

Rao, A.V., et al; "The Bioactivity of Saponins: Triterpenoid and Steroidal Glycosides"; *Drug Metabolism and drug interactions*; vol. 17, No. 1-4; pp. 212-235 (2000).

Simmons, R.D., et al; "Sialyl ligands facilitate lymphocyte accumulation during inflammation of the central nervous system"; *Journal of Neuroimmunology*; vol. 41; pp. 123-130 (1992).

Ulbrich, H., et al; "Leukocyte and endothelial cell adhesion molecules as targets for therapeutic interventions in inflammatory disease"; *Trends in Pharmacological Sciences*; vol. 24, No. 12; pp. 640-647 (2003).

VanderElst, I.E., et al; "β1,6 N-Acetylglucosaminyltransferase (core 2 GlcNAc-T) expression in normal rat tissues and different cell lines: evidence for complex mechanisms of regulation"; *Glycobiology*, vol. 8, No. 7; pp. 731-740 (1998).

Washington, R., et al; "Expression of Immunologically Relevant Endothelial Cell Activation Antigens on Isolated Central Nervous System Microvessels from Patients with Multiple Sclerosis"; *Annals of Neurology*; vol. 35, No. 1; pp. 89-97 (1994).

Belozerskaya V, et al, Effect of steroid glycosides on *Neurospora crassa* Membranes; Applied Biochemistry and Microbiology, vol. 30, No. 6 1994 pp. 724-728.

Brockhausen I et al; The separation of liquid chromatography (under elevated pressure) of phenyl, benzyl, and $_o$- nitrophenyl glycosides of oligosaccharides. Analysis of substrates and products for four N-acetyl-$_D$- Glucosaminyl-transferases involved in mucin synthesis; Carbohydrate Research, 120(1983) pp. 3-16.

Brower Thomas D et al; Rheumatoid Arthritis; Journal of the Kentucky Medical Association, May 1983, pp. 281-286.

Chiang HC et al Xanthine Oxidase Inhibitors from the Roots of Eggplant (*Solanum melongena* L), J. Enzyme Inhibition 1993, vol. 7, pp. 225-235.

Deepak M et al., Quantitative Determination of the Major Saponin Mixture Bacoside A in *Bacopa monnieri* by HPLC; Phytochemical Analysis 16, pp. 24-29 )2005).

Djerassi C et al., J. Biol Chem. Jan. 1952; 194(1) 115-8.

Eisenreichova E et al ., A new steroidal saponin from the bulbs of *Lilium candidum*., Pharmazie (2000) 55 (7) pp. 549-550.

Faul William h et al., Side-chain Transformations and Deuterium Labeling in the Steroidal Sapogenin Series., J. Org. Chem. vol. 35, No. 8, 1970 pp. 2571-2585.

Gautam et al ., Immunomodulatory activity of Asparagus racemosus on systemic Th1/Th2 immunity, Implications for immuno adjuvant potential. J. ethnopharmacology, 121, 241-247 (2009).

Girardon P et al., Volatile Constituents of Fenugreek Seeds, Planta Medica 1985, pp. 533-534.

Hayes PY., et al, Structural revision of shatavarins I and IV, the major components from the roots of *Asparagus racemosus*, Tetrahedron Letters 47 (2006) 6965-6969.

Hostettmann K et a.l Saponins. Cambridge University Press UK. (1995).

Hou C et al., Bacopaside III, Bacopasaponin G, and Bacopasides A, B, and C from *Bacopa Monniera*, J. Nat. Prod 2002, 65 1759-1763.

Hu K et al., Protodioscin (NSC-698 796) Its Spectrum of Cytotoxicity Against Sixty Human Cancer Cell Lines in an Anticancer Drug Screen Panel, Planta Med 2002; 68: 297-301.

Hu K et al., The cytotoxicity of protoneodioscin (NSC-698789), a furostanol saponin from the rhizomes of *Dioscorea collettii* var. *hypoglauca*, against human cancer cells in vitro, Phytomedicine 9: 560-565, 2002.

Hu K et al., The Cytotoxicity of Methyl Protoneodioscin (NSC-698791) Against Human Cancer Cell Lines In Vitro: Anticancer Research 22: 1001-1006 (2002).

Hu K et al., Antineoplastic Agents; 1. Three Spirostanol Glycosides from Rhizomes of *Dioscorea Collettii* var. *hypoglauca*: Planta Medica 62 (1996) 573-575.

Inamdar AC et al., Comparison between Shatavar and *Asparagus spp.*: Bioyigyanam 6: 27-35, 1980.

Inoue T et al., Steroidal Glycosides from *Allium macleanii* and *A. senescens*, and their inhibitory activity on tumour promoter-induced phospholipid Metabolism of Hela Cells: Phytochemistry vol. 40, No. 2, pp. 521-525 (1995).

Jin M et al., Cytotoxic Steroidal Saponins from *Polygonatum zanlanscianense*, J. Nat. Prod. , 67, 1992-1995. (2004).

Joussen AM et al., Nonsteroidal anti-inflammatory drugs prevent early diabetic retinopathy via TNF-α suppression: The FASAB Journal, Mar. 2002, vol. 16 pp. 438-440.

Derwent Publications Ltd., London, GB AN 2001-412294 & JP 2001 072597 A (Mercian) Corp; Mar. 21, 2001; (abstract).

Kostova I et al., Two new sulfated Furostanol Saponins from *Tribulus terrestris*: Z Naturforsch, 57c, pp. 33-38 (2002).

Li M et al., Synthesis of monomethylated dioscin derivatives and their antitumor activities: Carbohydrate Research 338 (2003) 117-121.

Liu M et al., Synthesis of (25R)-ruscogenin-l-yl β-D-xylopyranosyl-(1→3)-[β-D-glucopyranosyl-(1→2)]-β-D-fucopyranoside: Carbohydrate Research 329 (2000) 745-754.

Liu H et al., New Furostanol Glycosides from the Rhizomes of *Dioscorea futschauensis* R. Kunth:Journal of Asian Natural Products Research 2003, vol. 5 (4) pp. 241-247.

Liu M et al., Diosgenin induces cell cycle arrest and apoptosis in human leukemia K562 cells with the disruption of $Ca^{2+}$ homeostasis: Cancer Chemother Pharmacol (2005) 55: 79-90.

Madar Z et al., Fenugreek (*Trigonella foenumgraecum*) as a means of reducing postprandial glucose level in diabetic rats: Nutrition Reports International Jun. 1984, vol. 29, No. 6, pp. 1267-1273.

Mahato SB et al., Bacopasaponins E and F: two jujubogenin bisdesmosides from *Bacopa monniera*: Phytochemistry 53 (2000) 711-714.

Markine-Goriaynoff N et al., The core 2 β-1, 6-N-acetylglucosaminyltransferase-M encoded by bovine herpesvirus 4 is not essential for virus replication despite contributing to post-translational modifications of structural proteins: Journal of General Virology (2004) 85, 355-367.

Melo PS et al., Cytotoxicity of phytosterol diosgenin and its derivatives in rat cultured hepatocytes and V79 fibroblasts: Human & Experimental Toxicology (2004) 23, 487-493.

Nakamura T et al., Interaction of Saponins with red blood cells as well as with the phosphatidylcholine liposomal membranes; J> Pharm Dyn. 2, 374-382 (1979).

Nian H et al., Protective effect of steroidal saponins from rhizome of *Anemarrhena asphodeloides* on ovarietomy-induced bone loss in rats; Acta Pharmacologica Sinica Jun. 2006: 27 (6) pp. 728 734.

Paseshnichenko VA et al., Isolation and Properties of Saponins from *Dioscorea deltoidea* Rhizomes; Applied Biochem. Microbiol. 1975, II (1) p. 83-90.

Pawar R et al., Dammarane Triterpene Saponin from *Bacopa monniera* as the Superoxide inhibitor in Polymorphonuclear Cells; Planta Med 67 (2001) pp. 752-754.
Quan HJ et al., Preparations of heterospirostanols and their pharmacological activities; Eur. J Med. Chem 37 (2002) pp. 659-669.
Raju J et al., *Trigonella foenum graecum* (fenugreek) seed powder improves glucose homeostasis in alloxan diabetic rat tissues by reversing the altered glycolytic, gluconeogenic and lipogenic enzymes; Molecular and Cellular Biochemistry 224: 45-51, 2001.
Ribes G et al., Effects of Fenugreek Seeds on Endocrine Pancreatic Secretions in Dogs; Ann Nutr Metab 28: 37-43 (1984).
Shao Y et al., Anti-tumor activity of the crude saponins obtained from asparagus; Cancer Letters 104 (1996), 31-36.
Shao Y et al.,Steroidal Saponins from *Asparagus officinalis* and Their Cytotoxic Activity; Planta Medica 63 (1997) 258-262.
Sharma RD; Effect of Fenugreek Seeds and Leaves on Blood Glucose and Serum Insulin Responses in Human Subjects; Nutrition Research, vol. 6, pp. 1353-1364 (1986).
Sharma SC et al; Steroidal Saponins of *Asparagus adscendens*; Phytochemistry, vol. 21, No. 8, pp. 2075-2078 (1982).
Shimomura H et al; 26-O-Acylated Furostanol Saponins Pardarinoside A and B from the Bulbs of *Lilium pardarinum*; Chem. Pharm. Bull. 36 (8) 3226-3229, 1988.
Sheilds et al Acute Multiple Sclerosis, characterized by extensive mononuclear phagocyte infiltration. Neurochem. res. 25, 1517-1520. (2000).
Singh SB et al., Furostanol Saponins from *Paris polyphylla* Structures of Polyphyllin G and H; Phytochemistry, vol. 21, No. 8, pp. 2079-2082, 1982.
Sinha J et al; Bacopasaponin C: Critical Evaluation of Anti-Leishmanial Properties in Various Delivery Modes; Drug Delivery, 9: 55-62, 2002.
Sur P et al; *Trigonella Foenum graecum* (Fenugreek) Seed Extract as an Antineoplastic Agent; Phytotherapy Research, 15 257-259 (2001).
Spruce et al (2004) Intrinsic factors implicated in the sequence of diabetic neuropathy and foot ulceration: a potential role of core2 betal, 6-N-acetylglucoseaminyltransferase (core2GlcNAcT-I) [core 2 transferase]. *Diabetic Medicine*, 21 (Suppl. 2), 1-35.
Vachalkova A et al., Potential carcinogenic and inhibitory activity of compounds isolatyed from *Lilium candidum* L; Neoplasma, 47, 5, 2000 pp. 313-318.
Vasileva.,. Composition and Biological Activity of Steroidal Glycosides from cell suspensions of *Dioscorea deltoidea* Wall. Prikl Biokhim Mikrobiol 1995, vol. 31 (2) pp. 238-242. English Abstract.
Vasileva, Isolation and properties of Saponins from *Dioscorea deltoidea* Wall Rhizomes. Prikl Biokhim Mikrob, 1975, II (1), p. 94-101—English Abstract.
Van Der Elst I and Datti A. β1,6 N-Acetylglucosaminyltransferase (core 2 GlcNAc-T) expression in normal rat tissues and different cell lines: evidence for complex mechanisms of regulation. Glycobiology vol. 8 No. 7 pp. 731-740, (1998).
Vasileva, Composition and Biological Activity of Steroid Glycosides from Cell Suspensions of *Discorea deltoidea* Wall; Applied Biochemistry and Microbiology, vol. 31, No. 2 1995, pp. 206-209.
Vasyukova NI., Fungitoxic Properties of Steroid Saponins from *Dioscorea deltodea* Rhizomes; Applied Biochem Microbol. 1977, 13 (2) pp. 128-131.
Yu J et al., Progress in studies on chemical constituents and pharmacological effect of *Trigonella foenum-graecum*. Chinese traditional and Herbal Drugs, 34(12) 1146-1149 (2003).
Li C et al., Synthesis of diosgenyl α-L rhamnopyranosyl-(1→2)-[β-D-glucopyrampsyl-{1→3)]-β-D-glucopyranoside {gracillin} amd related saponins;Carbohydrate Research 306 (1998) pp. 189-195.
Yu B et al., First Synthesis of a Bidesmosidic Triterpene Saponin by a Highly Efficient Procedure; J.AM.Chem.Soc. 1999, 121, pp. 12196-12197.
Zou CC et al., The synthesis of gracillin and dioscin: two typical representatives of spirostanol glycosides; Carbohydrate Research 338 (2003) pp. 721-727.
Akhov, L.S. et al; Biological activity of Deltoside from *Allium Nutans L.*, Saponins in Food, Feedstuffs and Medicinal Plants Chapter 23, pp. 227-231 (2000).
Chen, C. et al; Yunnan Zhiwu Yanjiu, vol. 9 (4) 495-502 (1987).

Garai ,S. et al., Bacopasaponin D-A Pseudojujubogenin Glycoside from *Bacopa Monniera*; Phytochemistry, vol. 43, No. 2, pp. 447-449 (1996).
Hosny, M. et al., Balanitoside, A furostanol Glycoside, and 6-Methyl-Diosgenin from *Balanites Aegyptiaca*, Phytochemistry, vol. 31, No. 10 pp. 3565-3569 (1992).
Kim, H et al., Chemical Synthesis of 15-Ketosterols and their Inhibitions of Cholesteryl Ester Transfer Protein: Bioorganic & Medicinal Chemistry, vol. 3, No. 4, pp. 367-374 (1995).
Mimaki, Y. et al., Steroidal Saponins from the Bulbs of *Lilium Brownii*: Phytochemistry, vol. 29, No. 7, pp. 2267-2271 (1990).
Miyahara, K. et al., Conversion of Steroid Saponins to the Corresponding Pregnane Glycosides: Chem. Pharm. Bull. 20 (11) 2506-2510 (1972).
Mori, K. et al., Synthesis of some analogues of Blattellastanoside A, the Steroidal Aggregation Pheromone of the German Cockroach: Bioorganic & Medicinal Chemistry, vol. 4, No. 3, pp. 401-408 (1996).
Ori, K. et al., Norlanostane and Lanostane Glycosides from the Bulbs of *Chionodoxa Luciliae* and Their Cytotoxic Activity; Chem. Pharm. Bull 51 (1) 92-95 (2003).
Takahashi, T. et al., Increased Spontaneous Adherence of Neutrophils from Type 2 Diabetic Patients with Overt Proteinuria; Diabetes Care, vol. 23, No. 3 pp. 417-418 (2000).
Tribosten; Box from sample of a protodioscin containing extract sold by Thermolife International (Purchased 2004 on line).
Vasileva, et al., Steroid Glycosides from Suspension Cultures of *Dioscorea Deltoidea Cells and Their Biological Activity in "Saponins used in Traditional and Modern Medicine" Eds Waller and Yamasaki, Plenum Press New York.* (1996).
Yamishita, T. et al., Structures of three new steroidal alkaloid glycosidesm solaverines I, II and III from Solanum Toxicarium and S. Verbascifolium; Chem. Pharm. Bull. 38 (3) pp. 827-829 (1990).
Yang, X. et al., The effect of TNF-α on glycosylation pathways in bovine synoviocytes; Biochem. Cell Biol. 82 pp. 559- 568 (2004).
M. Al-Habori and Am Ala Raman; "Pharmacological Properties"; *Fenugreek the genus Trigonella*; Edited by Georgios A. Petropoulos; Published by Taylor & Francis Inc. New York, pp. 162-182 (2002).
N. M. Ammar, et al; "Study of the Anti-Inflammatory Activity of Some Medicinal Edible Plants Growing in Egypt"; *Journal of Islamic Academy of Sciences*; 10:4, pp. 113-122 (1997).
H. Skalsta; "Chemical Constituents"; *Fenugreek, the genus Trigonella*; Edited by Georgios A. Petropoulos; Published by Taylor & Francis Inc. New York; pp. 132-161 (2002).
K. Maemura and M. Fukuda; "Poly-N-acetyllactosaminyl O-Glycans Attached Leukosialin—The Presence of Sialyl Le$^x$ Structures in O-Glycans"; *J. Biol. Chem.*; 267:34, pp. 24379-24386 (1992).
K. Hostettman and A. Marston; Chemistry and Pharmacology of Natural Products; *Saponins Published by Cambridge University Press*, Extracted pages (1995).
B. Dang, et al; "Increased PSGL-1 expression on granulocytes from allergicasthmatic subjects results in enhanced leukocyte recreuitment under flow conditions"; *J Leukocyte Biol.*; 72, pp. 702-710 (2002).
R.L. Dedrick et al; Adhesion Molecules as Therapeutic Targets for Autoimmune Diseases and Transplant Rejection; *Expert Opin. Biol. Ther.*; 3(1); pp. 85-89 (2003).
T. Kawasaki et al; "Furostanol Bisglycosides Corresponding to Dioscin and Gracillin"; *Chem. Pharm. Bull.*; 22(9); pp. 2164-2175 (1974).
Y. Mimaki et al; Steroidal Saponins From the Rhizomes of *Paris polyphylla var. Chinensis* and Their Cytotoxic Activity on HL-60 Cells; *Natural Product Letters*; 14(5); pp. 357-364 (2000).
T. Purdie and J. Irvine; Synthesis from Glucose of an Octamethylated disaccharide methylation of Sucrose and Maltose; *J. Chem. Soc.*; 87; p. 1022 (1905).
J.-F. Theoret; "P-Selectin Antagonism with Recombinant P-Selectin Glycoprotein Ligand-1 (rPSGL-lg) Inhibits Circulating Activated Platelet Binding to Neutrophils Induced by Damaged Arterial Surfaces"; *The Journal of Pharmacology and Experimental Therapeutics*; 298; pp. 658-664 (2001).

* cited by examiner

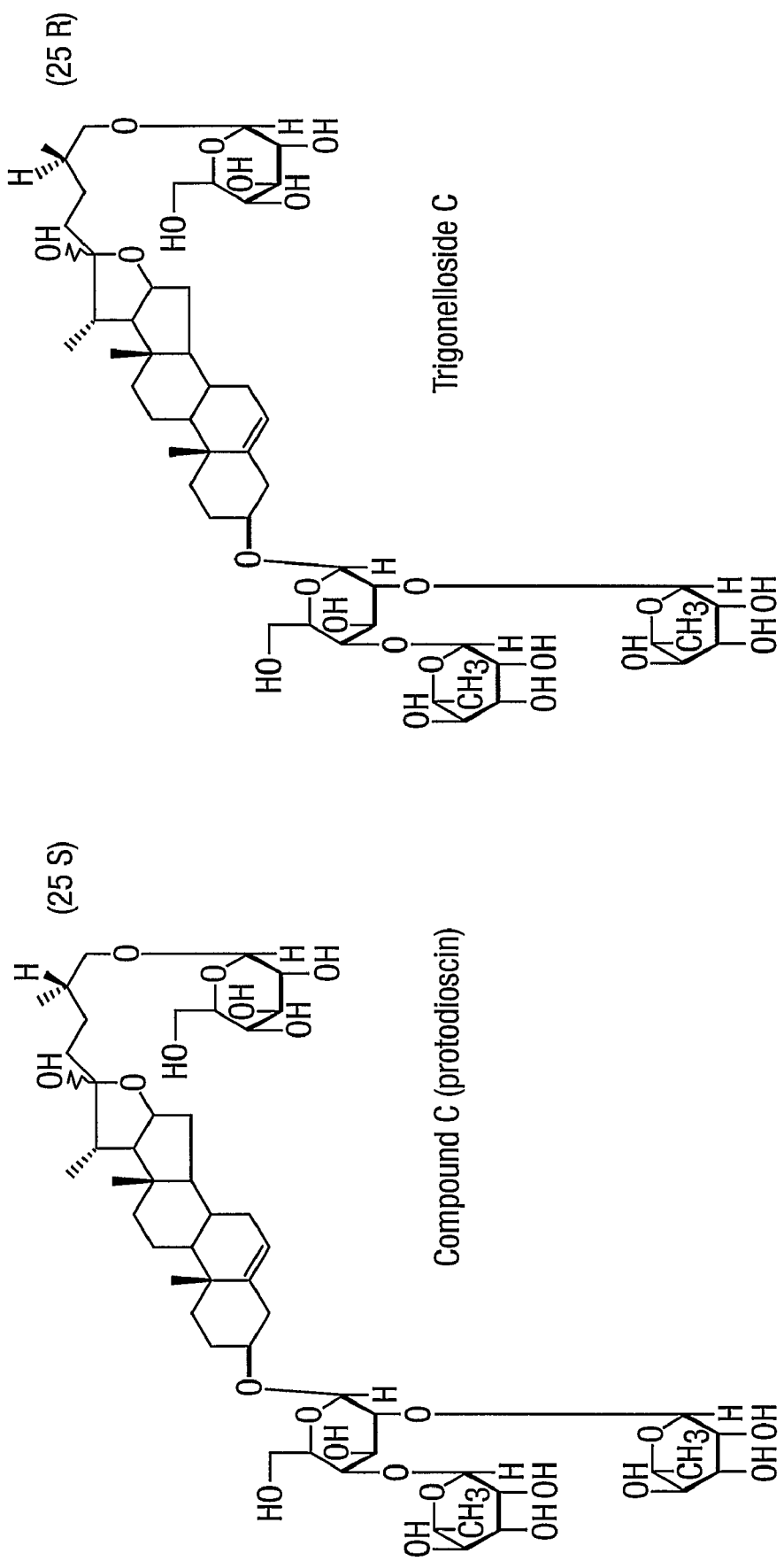
Fig.14(iii).

CORE 2 GLCNAC-T INHIBITORS

This application is the U.S. National Phase of International Application PCT/GB2004/005398, filed 22 Dec. 2004, which designated the U.S. PCT/GB2004/005398 claims priority to British Application No. 0329667.0 filed 22 Dec. 2003. The entire content of these applications are incorporated herein by reference.

The present invention relates to the use of known and novel compounds as inhibitors of UDP-GlcNAc:Galβ1,3GalNAc-R (GlcNAc to GalNAc) β-1,6-N-acetylglucosaminyl transferase (core 2 β-1,6 N-acetylaminotransferase, core 2 GlcNAc-T-EC 2.4.1.102).

Such inhibitors have applications in therapy for diseases associated with raised activity of core 2 GlcNAc-T, in particular inflammatory diseases, athero-sclerosis, diabetic cardiomyopathy, cancers—including treatment or prevention of metastasis—or diabetic retinopathy.

The present inventors have determined that the compounds herein described can inhibit glucose-induced activity of core 2 GlcNAc-T and glucose induced binding of human leukocytes to cultured bovine retinal capillary endothelial cells as measured in assays described herein. The administration of these compounds, hereinafter referred to as Core 2 GlcNAc-T inhibitors to patients can prevent or treat the abnormal formation of core 2 O-glycans and sialyl Lewis$^x$ by inhibiting raised activity of core 2 GlcNAc-T in the aforementioned disease states.

Following initiation of glycosylation by the attachment of an N-acetyl-glucosamine (GalNAc) to either a serine or threonine residue in a protein to be glycosylated, processing proceeds by elongation, branching and then terminal modification of the O-glycans.

Essential steps in O-glycan elongation and branching are catalysed by multiple glycosyl transferase isoforms from families of homologous glycosyltransferases. Depending on which saccharide groups are subsequently attached to this first GalNAc residue, O-glycans are divided into four major subtypes (FIG. 1). The core 1 structure is formed by addition of galactose to form Galβ1-3GalNAc-αSer/Thr. The core 2 structure requires the core 1 structure as substrate and is formed by addition of GlcNAc to form Galβ1-3(GlcNAcβ1-6)GalNAc-αSer/Thr. The core 3 structure is formed by the addition of GlcNAc to form GlcNAcβ1-3GalNAc-αSer/Thr. The core 4 structure requires the core 3 structure as substrate and is formed by addition of GlcNAc to form GlcNAcβ1-3(GlcNAcβ1-6)GalNAc-αSer/Thr. Other modifications to the core GalNAc structure have also been found, but appear to be uncommon. All these core structures are further modified by galactosylation, sialylation, fucosylation, sulfation or elongation to eventually form the O-glycan.

Three forms of Core 2 GlcNAc-T are known. Core 2 GlcNAc-T I identified in from leukemic cells, core 2 GlcNAc-T II identified in mucin secreting tissue, and a third thymus associated type designated core 2 GlcNAc-T III.

Cell surface O-glycans are known to play a crucial role in mediating cell-cell interactions in development and certain disease states. The patterns of protein glycosylation are determined largely by the activity and specificity of the glycotransferase enzymes, such as core 2 GlcNAc-T which is expressed in the Golgi apparatus (1-2). Core 2 GlcNAc-T plays a crucial role in the biosynthesis of O-linked glycans (3-4) and represents an important regulatory step for the extension of O-linked sugars with polylactosamine (i.e. repeating Galβ1-4GlcNAcβ1-3), a structure associated with malignant transformation (5-6).

Changes in the activity of core 2 GlcNAc-T have been associated with various disease states, such as T-cell activation, cancers, metastasis, myeloblastic leukaemia, myocardial dysfunction and inflammation (7-18). Regulation of core 2 GlcNAc-T is thought to be particularly important, because addition of lactosamine structures to the basic core oligosaccharides formed by this enzyme and subsequent modification with fucose and sialic acid, results in the formation of the Lewis$^x$, sialyl-sialyl Lewis$^a$, and Lewis$^x$ sugar groups that constitute the ligands of selectins which are cell adhesion proteins. This selectin-ligand interaction plays an important role in many processes.

Inflammation is how the body generally responds to infection or to some other form of trauma. One of the major events during inflammation is the movement of cells of the immune system from the blood stream to the infected or injured area. Once at the site of injury, these cells are responsible for the isolation, destruction and removal of the offending agent.

Acute inflammation, characterised by short duration (minutes to days), is essential for health, but sometimes the inflammatory process does not end when appropriate, and it is this that causes problems. Chronic inflammation is characterised by long duration (days, weeks, months and even years), lymphocytes and macrophages, tissue destruction and repair, and vascular proliferation and fibrosis. Inflammation can also be triggered inappropriately by the body's normal constituents and plays a role in common diseases, such as asthma, rheumatoid arthritis and inflammatory bowel disease.

Many cell adhesion molecules are known to be involved in the process of inflammation. At the site of inflammation, leukocytes first adhere to the vascular endothelial cells prior to the extravasation process. It is postulated that selectins play a crucial role in the initial adhesion of leukocytes to endothelial cells. Cell adhesion mediated by selectins and their carbohydrate ligands leads to the tethering and rolling of leukocytes on endothelial linings. This then leads to the secondary firm adhesion. Within hours of the initial stimulus, neutrophils begin to enter the tissue and may continue transmigration for many days. In some inflammatory conditions, tissue damage is caused by direct injury of the vessels and amplified by the subsequent recruitment of neutrophils into the tissue.

The expression of O-glycans reduces cell-cell interactions because of the bulkiness of these adducts. The expression of core 2 O-glycans is regulated by the transcriptional levels of core 2 GlcNAc-T in all of these cases. Antigen-mediated activation of peripheral T and B-cells is characterised by increased activity of core 2 GlcNAc-T and branched O-glycans on CD43 (leukosialin) (19-20).

Leukocyte extravasation, lymphocyte trafficking and other processes involve O-glycan synthesised by core 2 GlcNAc-T. Specifically, cell-surface O-glycan structures terminating in sialyl Lewis$^x$ are involved in the recruitment of leukocytes to the site of inflammation. Core 2 GlcNAc-T is not important for T-cell development, but over expression of this enzyme has been shown to completely block the development of myeloid lineages. Over expression of core 2 O-glycans has also been reported to affect the interaction between T-cells and B-cells (TB interaction). This T-B interaction is crucial for humoral immune response and is mediated through binding of the CD40 ligand (CD40L) on T-cells with CD40 on B-cells (CD40L-CD40 interaction). This interaction induces the proliferation of B-cells. Over expression of core 2 O-glycans has been shown to cause significant reduction in CD40L-CD40 interaction (21).

It is possible to effectively block the initial step of leukocyte invasion from taking place, by blocking the synthesis of sialyl Lewis$^x$ on the cell surface of activated leukocytes and thereby halting their interactions with selectins. Therefore, inhibitors of core 2 GlcNAc-T that can reduce the activity of core 2 GlcNAc-T have utility in modulating inflammation.

Atherosclerosis is a progressive inflammatory disease of unknown mechanism. Recruitment and adhesion of circulating leukocytes to the endothelium particularly at arterial branches and bifurcations is one of the earliest events known to occur in atherogenesis. Integrins on the leukocytes then cause a stronger attachment between the cells. Leukocytes transmigrate through into the sub-endothelial space where they begin to accumulate in the intima. Monocytes become converted to activated macrophages with the presence of oxidised low density lipoprotein (LDL-oxLDL), these activated macrophages take up the modified types of lipoprotein via their scavenger receptors and differentiate to become foam cells. Histological analysis of atherosclerotic coronary arteries from patients who died of acute coronary syndromes demonstrate foam cells, macrophages, lymphocytes and mast cells were present in unstable or ruptured plaques (49).

At least three leukocyte adhesion molecules, E-selectin, ICAM-1, and VCAM-1, have been identified in human atherosclerosis (50, 51). Further, in contrast to normal vessels, P selectin is overly expressed by epithelial cells in atherosclerotic lesions and expression of E-selectin (52) and ICAM-1 (53) at the arterial lumen, has been found to be increased in arterial segments with mononuclear leukocyte accumulation. A third adhesion molecule, VCAM-1, has been detected in animal models of athero-sclerosis, and also has been shown to be more prevalent in the intima of atherosclerotic plaques than in non atherosclerotic segments of human coronary arteries.

Chibber et al (54) evaluated the importance of core 2 GlcNAc-T in increased leukocyte-endothelial cell adhesion and found significant increases in the activity of this enzyme in leukocytes of diabetic patients. However, until now there has been no evidence that core 2 GlcNAc-T activity is raised in circulating leukocytes of patients suffering from atherosclerosis. The applicants have now demonstrated that activity of the enzyme Core 2 GlcNAc-T is indeed raised in circulating leukocytes from patients with atherosclerosis, suggesting that compounds capable of lowering the activity of core 2 GlcNAc-T would be useful in the treatment or prevention of atherosclerosis or in preventing reoccurrence of atherosclerotic plaques in patients following interventions.

Although the clinical symptoms of diabetic cardiomyopathy have been identified, its pathogenesis is uncertain. The definition of diabetic cardiomyopathy describes both specific defects in the diabetic's myocytes, such as fibrosis leading to myocardial hypertrophy and diastolic dysfunction, and associated changes in the heart which have developed during the course of diabetes.

There is now strong evidence suggesting that raised activity of core 2 GlcNAc-T is directly responsible for elevated glycoconjugates, commonly observed in the heart tissue of diabetic animals and patients. In support of this, it has recently been shown that increased core 2 GlcNAc-T activity causes pathology similar to that observed in the heart of diabetic patients after years with the condition, in the heart of diabetic experimental animal models. Studies were carried out using a transgenic mouse with core 2 GlcNAc-T expression driven by a cardiac myosin promoter. At 4 months, a marked hypertrophy of the left ventricle and general hypertrophy of the heart was observed (16-17).

Marked changes in core 2 branching and core 2 GlcNAc-T activities are associated with malignant transformation, leukaemia and carcinomas (21, 33-36). Rat fibroblasts and mammary carcinoma cells transfected with T24H-ras express core 2 O-glycans as they become metastatic tumours (33).

There is a great deal of evidence pointing to the involvement of core 2 GlcNAc-T in cancer and cancer metastasis. For example, highly metastatic colonic carcinoma cells both express more sialyl Lewis$^x$ than their low metastatic counterparts and adhere more strongly to E-selectin than poorly metastatic cells. There is a strong correlation between the expression of sialyl Lewis$^x$ in tumour cells and tumour progression (34). Moreover, a good correlation exists between the expression of sialyl Lewis X in core 2 O-glycans and lymphatic and venous invasion.

Recent findings suggest that core 2 GlcNAc-T in combination with α1,3-Fuc-T contributes to the selectin-mediated metastasis in oral cavity carcinomas (35). Moreover, Western blot analysis revealed the presence of a major approximately 150 kDa glycoprotein that carries a-linked oligosaccharides recognised by anti-sLe$^x$ monoclonal antibody in sLe$^x$-positive pre-B leukaemia cell lines. This correlation of core 2 GlcNAc-T with CD 15 expression suggests that core 2 GlcNAc-T is a regulator of the cell surface expression of sialyl Lewis$^x$ in human pre-B lymphoid cells. These results indicate that core 2 GlcNAc-T mRNA detected by in situ hybridisation reflects the malignant potentials of pulmonary adenocarcinoma, because lymph node metastasis is the most affecting factor to the patient's prognosis.

Expression of sialyl Lewis$^x$ in mouse melanoma B16-FI by transfection with the enzyme 1,3-fucosyltransferase have also confirmed the importance of sialyl Lewis$^x$ in tumour metastasis. Intravenous injection of the transfected cells into mice formed a large number of lung tumour nodules, while the parent B16-FI cells scarcely formed tumours.

The expression of sialyl Lewis$^a$, sialyl Lewis$^x$ (both selectin ligand carbohydrate structures) and raised activity of core 2 GlcNAc-T are all closely associated with malignancy of colorectal cancer (36). Recently, Numahata (37) demonstrated that sialyl Lewis$^x$ expression in primary bladder carcinoma is a predictor of invasive and metastatic outcome. No other carbohydrate epitope examined to date has equal prognostic value. Recently US 2004/0033521 disclosed that core 2b GlcNAc-T is over expressed in both liver and stomach tumours and in colon cancer and liver metastasis samples. Furthermore, WO 04/093662 demonstrates that core 2 GlcNAc-T is raised in prostate cancer testicular and bladder cancer. Levels of core 2 GlcNAc-T increase with increasing chance of metastasis or recurrence of disease.

Accordingly inhibitors of core 2 GlcNAc-T would be expected to reduce the production of the O-glycans, for example those bearing sialyl Lewis$^x$, and would reduce cancer invasiveness and metastasis and be useful in treatment of cancers where core 2 GlcNAc-T expression is raised above normal levels for that tissue type.

Diabetic retinopathy is a progressive vision threatening complication of diabetes (38) characterised by capillary occlusion, formation of microvascular lesions and retinal neovascularisation adjacent to ischaemic areas of the retina (39-40).

It has recently been found that raised activity of core 2 GlcNAc-T is directly responsible for increased leukocyte-endothelial cell adhesion and capillary occlusion in diabetic retinopathy (41). It has now also been demonstrated that elevated glucose and diabetic serum increase the activity of core 2 GlcNAc-T and the adhesion of human leukocytes to endothelial cells. This occurs through PKCβ2-dependent phosphorylation of core 2 GlcNAc-T (42-43). This regulatory mechanism involving phosphorylation of core 2 GlcNAc-T is also present in polymorphonuclear leukocytes (PMNs) isolated from Type 1 and Type 2 diabetic patients.

Inhibition of PKCβ2 activation by the specific inhibitor, LY379196, attenuates serine phosphorylation of core 2 GlcNAc-T, prevents the increase in activity and thus prevents increased leukocyte-endothelial cell adhesion. Such an inhibitor provides validation that reduction of core 2 GlcNAc-T activity provides a method of preventing increased leukocyte-endothelial cell adhesion and preventing capillary occlusion in retinopathy associated with diabetes or hyperglycaemia.

Fenugreek has been used for thousands of years for the treatment of diabetes. The plant contains many active ingredients, such as coumarins, saponins and glycosides, Many studies (44) have demonstrated the hypoglycaemic properties of fenugreek in both animals and humans. The hypoglycaemic properties have been attributed to the amino acid 4-hydroxyisoleucine which has potent insulinotropic activity (45-46).

The present inventors have now determined that certain compounds are inhibitors of Core 2 GlcNAc-T. Certain of these compounds are obtainable from fenugreek seeds and from other plant sources.

In a first aspect of the invention is provided a method of treatment of conditions associated with raised activity of the enzyme core 2 GlcNAc-T comprising administration of an effective amount of a compound of the formula I to a patient in need thereof. Preferably, the disease is an inflammatory disease, asthma, rheumatoid arthritis, inflammatory bowel disease, diabetic cardiomyopathy, myocardial dysfunction, cancer, cancer metastasis or diabetic retinopathy.

Cancers include leukaemia, oral cavity carcinomas, pulmonary cancers such as pulmonary adenocarcinoma, colorectal cancer, bladder carcinoma, liver tumours, stomach tumours colon tumours, prostate cancer, testicular tumour, mammary cancer, lung tumours oral cavity carcinomas and any cancers where core 2 GlcNAc-T expression is raised above normal levels for that tissue type.

Preferably the core 2 GlcNAc-T inhibitor comprises a sugar-derived substituent. The term sugar-derived substituent means a saccharide, in which optionally one or more hydrogens and/or one or more hydroxyl groups have been replaced by -R, —OR, —SR, —NR wherein R is methyl, ethyl or propyl to form a derivative.

Saccharides include, but are not limited to, monosaccharides, disaccharides, trisaccharides, tetrasaccharides and polysaccharides.

Monosaccharides include, but are not limited to, arabinose, xylose, lyxose, ribose, glucose, mannose, galactose, allose, altrose, gulose, idose, talose, ribulose, xylulose, fructose, sorbose, tagatose, psicose, sedoheptulose, deoxyribose, facose, rhamnuose, 2-deoxy-glucose, quinovose, abequose, glucosamine, mannosamine, galactosamine, neuraminic acid, muramic acid, N-acetyl-glucosamine, N-acetyl-mannosamine, N-acetyl-galactosamine, N-acetylneuraminic acid, N-acetylmuramic acid, O-acetylneuraminic acid, N-glycolylneuraminic acid, fructuronic acid, tagaturonic acid, glucuronic acid, mannuronic acid, galacturonic acid, iduronic acid, sialic acid and guluronic acid.

Preferably, the core 2 GlcNAc-T inhibitor comprises at least one sugar-derived substituent; more preferably, the core 2 GlcNAc-T inhibitor comprises at least two sugar-derived substituents.

Preferably, each sugar-derived substituent is independently a mono-, di-, tri- or tetrasaccharide; more preferably, each sugar-derived substituent is independently a mono- or trisaccharide.

Preferably, the core 2 GlcNAc-T inhibitor is a compound of the formula I

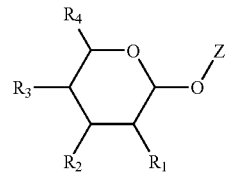

wherein $R_1$ is —OH, $C_{1-6}$ alkoxy, —$NR_8R_9$, or a monosaccharide of the formula: IIa:

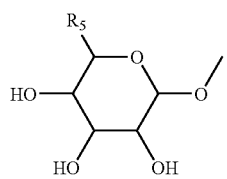

Preferably $R_1$ is —OH, —$NR_8R_9$, or a monosaccharide of the formula IIa; more preferably $R_1$ is —$NR_8R_9$, or a monosaccharide of the formula IIa; most preferably $R_1$ is a monosaccharide of the formula IIa;

$R_2$ is —OH, $C_{1-6}$ alkoxy or a monosaccharide of the formula IIb:

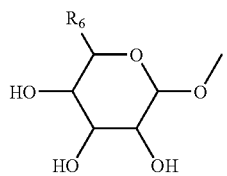

Preferably $R_2$ is —OH or a monosaccharide of the formula III; more preferably $R_2$ is —OH or a monosaccharide of the formula III; most preferably $R_2$ is —OH;

$R_3$ is —OH, $C_{1-6}$ alkoxy or a monosaccharide of the formula IIc:

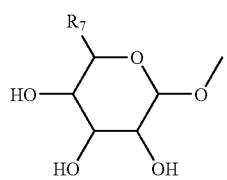

Preferably $R_3$ is —OH or a monosaccharide of the formula IIc; more preferably $R_3$ is a monosaccharide of the formula IIc; most preferably $R_3$ is glucose;

$R_4$ is $C_{1-6}$ alkyl, $C_{1-6}$ hydroxyalkyl or $C_{1-6}$-alkoxy-$C_{1-6}$-alkyl; preferably $R_4$ is $C_{1-6}$ alkyl or $C_{1-6}$ hydroxyalkyl; more preferably $R_4$ is —$CH_2OH$ or —$CH_3$; most preferably $R_4$ is —$CH_2OH$;

$R_5$ is $C_{1-6}$ alkyl, $C_{1-6}$ hydroxyalkyl or $C_{1-6}$-alkoxy-$C_{1-6}$-alkyl; preferably $R_5$ is $C_{1-6}$ alkyl or $C_{1-6}$ hydroxyalkyl; more preferably $R_5$ is —$CH_3$, —$C_2H_5$, —$CH_2OH$ or —$C_2H_4OH$; most preferably $R_5$ is —$CH_3$;

$R_6$ is $C_{1-6}$ alkyl, $C_{1-6}$ hydroxyalkyl or $C_{1-6}$-alkoxy-$C_{1-6}$-alkyl; preferably $R_6$ is $C_{1-6}$ alkyl or $C_{1-6}$ hydroxyalkyl more preferably $R_6$ is —$CH_2OH$ or —$CH_3$; most preferably $R_6$ is —$CH_2OH$;

$R_7$ is $C_{2-6}$ alkyl, $C_{1-6}$ hydroxyalkyl or $C_{1-6}$-alkoxy-$C_{1-6}$-alkyl; preferably $R_7$ is $C_{1-6}$ hydroxyalkyl or $C_{1-6}$-alkoxy-$C_{1-6}$-alkyl; more preferably $R_7$ is —$CH_2OH$ or $C_{1-6}$ alkoxymethyl; most preferably $R_7$ is —$CH_2OH$;

$R_8$ is H, $C_{1-6}$ alkyl or $C_{1-6}$ acyl; preferably $R_8$ is H or $C_{1-6}$ alkyl; more preferably $R_8$ is H or $CH_3$; most preferably $R_8$ is H;

$R_9$ is H, $C_{1-6}$ alkyl or $C_{1-6}$ acyl; preferably $R_9$ is H or $C_{1-6}$ acyl more preferably $R_9$ is H or —$COCH_3$; most preferably $R_9$ is —$COCH_3$; and Z is a steroid group;

or a pharmaceutically acceptable salt, ester or tautomeric form or derivative thereof.

Preferably the compound of the formula I is a compound of the formula III:

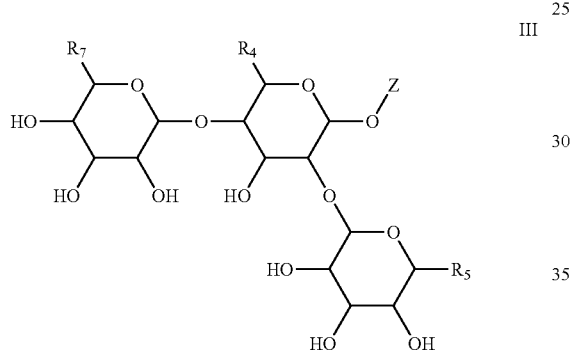

wherein:

$R_4$ is $C_{1-6}$ alkyl, $C_{1-6}$ hydroxyalkyl or $C_{1-6}$-alkoxy-$C_{1-6}$-alkyl; preferably $C_{1-6}$ alkyl or $C_{1-6}$ hydroxyalkyl more preferably —$CH_2OH$ or —$CH_3$; most preferably —$CH_2OH$;

$R_5$ is $C_{1-6}$ alkyl, $C_{1-6}$ hydroxyalkyl or $C_{1-6}$-alkoxy-$C_{1-6}$-alkyl; preferably $R_5$ is $C_{1-6}$ alkyl or $C_{1-6}$ hydroxyalkyl; more preferably $R_5$ is —$CH_3$, —$C_2H_5$, —$CH_2OH$ or —$C_2H_4OH$; most preferably $R_5$ is —$CH_3$; and $R_7$ is $C_{2-6}$ alkyl, $C_{1-6}$ hydroxyalkyl or $C_{1-6}$-alkoxy-$C_{1-6}$-alkyl; preferably $R_7$ is $C_{1-6}$ hydroxyalkyl or $C_{1-6}$-alkoxy-$C_{1-6}$-alkyl; more preferably $R_7$ is —$CH_2OH$ or $C_{1-6}$ alkoxymethyl; most preferably $R_7$ is —$CH_2OH$.

More preferred are compounds of the formula III wherein:

$R_4$ is $C_{1-6}$ hydroxyalkyl or $C_{1-6}$ alkyl;
$R_5$ is $C_{1-6}$ alkyl, $C_{1-6}$ hydroxyalkyl; and
$R_7$ is $C_{1-6}$ hydroxyalkyl or $C_{1-6}$-alkoxy-$C_{1-6}$-alkyl.

More preferred are compounds wherein:

$R_4$ is —$CH_2OH$ or —$CH_3$;
$R_5$ is —$CH_3$; and
$R_7$ is —$CH_3OH$.

Most preferred compounds of the formula III are compounds of the formula I wherein:

$R_1$ is rhamnose;
$R_2$ is —OH;
$R_3$ is glucose; and
$R_4$ is —$CH_2OH$.

Most preferred are compounds of the formula I which are of the formula IV:

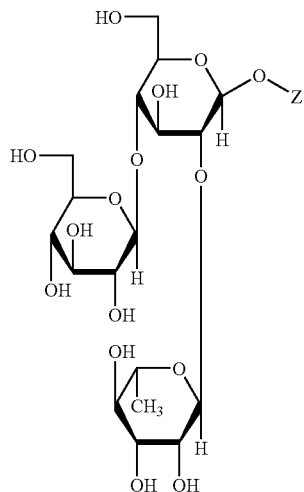

Also provided are compounds wherein the compound of the formula I is a compound of the formula V:

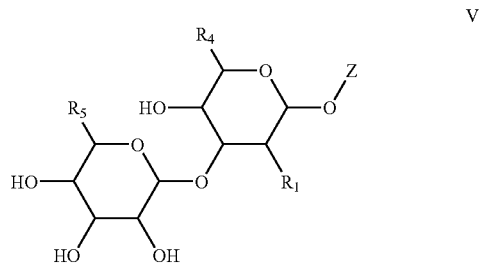

wherein:

$R_1$ is —OH, $C_{1-6}$ alkoxy or $NR_8R_9$, or a monosaccharide of the formula IIa:

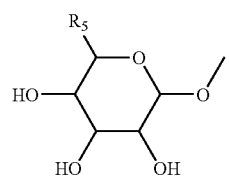

Preferably $R_1$ is —OH, or $NR_8R_9$; more preferably $R_1$ is $NR_8R_9$.

$R_4$ is $C_{1-6}$ alkyl, $C_{1-6}$ hydroxyalkyl or $C_{1-6}$-alkoxy-$C_{1-6}$-alkyl; preferably $R_4$ is $C_{1-6}$ alkyl or $C_{1-6}$ hydroxyalkyl more preferably $R_4$ is $C_{1-6}$ alkyl; most preferably —$CH_3$;

$R_5$ is $C_{1-6}$ alkyl, $C_{1-6}$ hydroxyalkyl or $C_{1-6}$-alkoxy-$C_{1-6}$-alkyl; preferably $R_5$ is $C_{1-6}$ alkyl or $C_{1-6}$ hydroxyalkyl; more preferably $R_5$ is —$CH_3$ or —$CH_2OH$; most preferably $R_5$ is —$CH_3$; and $R_6$ is $C_{1-6}$ alkyl, $C_{1-6}$ hydroxyalkyl or $C_{1-6}$-alkoxy-$C_{1-6}$-alkyl; preferably $R_6$ is $C_{1-6}$ alkyl or $C_{1-6}$ hydroxyalkyl more preferably $R_6$ is —$CH_2OH$ or —$CH_3$; most preferably $R_6$ is —$CH_2OH$;

$R_8$ is H, $C_{1-6}$ alkyl or $C_{1-6}$ acyl; preferably $R_8$ is H or $C_{1-6}$ alkyl; more preferably $R_8$ is H or $CH_3$; most preferably $R_8$ is H;

$R_9$ is H, $C_{1-6}$ alkyl or $C_{1-6}$ acyl; preferably $R_9$ is H or $C_{1-6}$ acyl more preferably $R_9$ is H or —$COCH_3$; most preferably $R_9$ is —$COCH_3$; and Z is a steroid group.

Preferred compounds of the formula V are compounds in which:

$R_1$ is —OH, $C_{1-6}$ alkoxy or $NR_8R_9$;

$R_4$ is $C_{1-6}$ alkyl or $C_{1-6}$ hydroxyalkyl;

$R_6$ is $C_{1-6}$ alkyl or $C_{1-6}$ hydroxyalkyl;

$R_8$ is H, $C_{1-6}$ alkyl or $C_{1-6}$ acyl; and $R_9$ is H, $C_{1-6}$ alkyl or $C_{1-6}$ acyl.

More preferred compounds of the formula IV are those in which:

$R_1$ is —NH—$C_{1-6}$-acyl;

$R_4$ is $C_{1-6}$ alkyl or —$CH_2OH$; and $R_6$ is $C_{1-6}$ hydroxyalkyl.

Most preferred are the compounds of the formula IV which are of the formula:

*Galβ1→3(6-deoxy)GalNAcα-Z*

The compounds of the formula I comprise a steroid group. The term "steroid group" means a group comprises the tetracyclic ring system shown as formula VI:

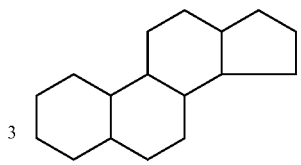

VI

Preferably the steroid group is attached to the rest of the molecule through the 3-position of the steroid group. For example compounds of the formula I above are preferably compounds of the formula:

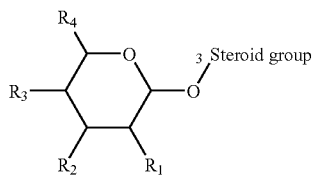

The steroid group may be cholestane, 5α-pregnane, androstane, estrane, cholesterol, cholane, a progestin, a glucocorticoid, a mineralocorticoid, an androgen such as dehydroepiandrosterone or its 7-keto analogue, a bile acid or other steroid. In one preferred embodiment the steroid core is a steroid that is in itself beneficial or neutral. By neutral is meant that the steroid itself has been passed suitable for use in a human or animal. By beneficial is meant that the steroid has effects of benefit to the human or animal if it were administered separately.

The steroid group may be a steroidal sapogenin derivable from plant sources or a steroidal sapogenin which is itself derivable from such plant steroidal sapogenins by chemical modification.

In one embodiment the steroid group is a steroidal sapogenin of the formula VII:

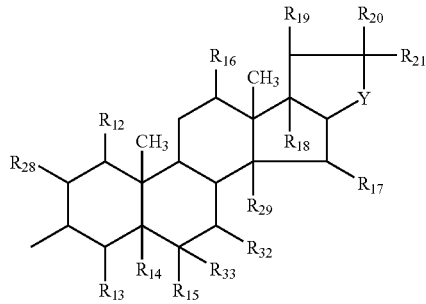

VII wherein:

$R_{12}$ is H, OH, $C_{1-6}$ alkyl or $C_{1-6}$ alkoxy; preferably $R_{12}$ is H or —OH; most preferably $R_{12}$ is H;

$R_{13}$ is H, —OH, =O, or $C_{1-6}$ alkyl; preferably $R_{13}$ is H or —OH; most preferably $R_{13}$ is H;

$R_{14}$ is H, —OH or $C_{1-6}$ alkyl or $R_{14}$ and $R_{33}$ taken together represent the second bond of a double bond joining adjacent carbon atoms; preferably $R_{14}$ is H or $R_{14}$ and $R_{33}$ taken together represent the second bond of a double bond joining adjacent carbon atoms;

$R_{15}$ is H, or —OH, or $R_{15}$ and $R_{33}$ taken together are =O; preferably $R_{15}$ is H, or $R_{15}$ and $R_{33}$ taken together are =O; more preferably $R_5$ is H;

$R_{16}$ is H, OH or =O; preferably $R_{16}$ is H or =O; more preferably $R_{16}$ is H;

$R_{17}$ is H, OH or =O; preferably $R_{17}$ is H or —OH; more preferably $R_{17}$ is H;

$R_{18}$ is H, OH, $C_{1-6}$ alkoxy or $C_{1-6}$ alkyl; preferably $R_{18}$ is H, OH, $C_{1-6}$ alkoxy; more preferably $R_{18}$ is H or OH; most preferably $R_{18}$ is H;

$R_{19}$ is H, OH, $C_{1-6}$ alkyl or $C_{1-6}$ alkoxy; preferably $R_{19}$ is H, OH, $C_{1-6}$ alkyl; more preferably $R_{19}$ is H, OH or $C_{1-6}$ alkyl; most preferably $R_{19}$ is $C_{1-6}$ alkyl; and particularly $R_{19}$ is —$CH_3$;

$R_{20}$ is H, OH, $C_{1-6}$ alkoxy or $C_{1-6}$ alkyl; preferably $R_{20}$ is H, —OH, or $C_{1-6}$ alkoxy; more preferably $R_{20}$ is —OH or $C_{1-6}$ alkoxy; most preferably $R_{20}$ is —OH;

$R_{21}$ is H, OH, $C_{1-6}$ alkyl, $C_{1-6}$ alkoxy or is a group of the formula VIII:

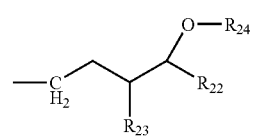

VIII preferably $R_{21}$ is a group of the formula VIII;

$R_{22}$ is H, OH, $C_{1-6}$ alkyl or $C_{1-6}$ alkoxy; preferably $R_{22}$ is H, OH, or $C_{1-6}$ alkoxy; preferably $R_{22}$ is H or OH, —$OCH_3$ or —O—$C_2H_5$; most preferably $R_{22}$ is H;

$R_{23}$ is H, OH, $C_{1-6}$ alkyl, $C_{1-6}$ hydroxyalkyl, $C_{1-6}$-alkoxy-$C_{1-6}$-alkyl, =$CH_2$ or =CH—$C_{1-6}$-alkyl; preferably $R_{23}$ is $C_{1-6}$ alkyl, $C_{1-6}$ hydroxyalkyl, $C_{1-6}$-alkoxy-$C_{1-6}$-alkyl, =$CH_2$ or =CH—$C_{1-6}$-alkyl; more preferably $R_{23}$ is $C_{1-6}$ alkyl, $C_{1-6}$ hydroxyalkyl or =$CH_2$; most preferably $R_{23}$ is —$C_2H_4OH$, —$CH_2OH$, $C_{1-6}$ alkyl, or =$CH_2$, even more preferably $R_{23}$ is —$C_2H_4OH$, —$CH_2OH$, —$C_2H_5$, —$CH_3$ or =$CH_2$ and particularly $R_{23}$ is —$CH_3$ or =$CH_2$; and $R_{24}$ is H, $C_{1-6}$ alkyl, $C_{1-6}$ acyl or a monosaccharide MS; preferably $R_{24}$ is $C_{1-6}$ alkyl, $C_{1-6}$ acyl or a monosaccharide MS; more preferably $R_{24}$ is $C_{1-6}$ acyl or a monosaccharide MS; most preferably $R_{24}$ is a monosaccharide MS.

$R_{28}$ and $R_{29}$ are the same or different and are H or OH; preferably $R_{28}$ is H and $R_{29}$ is —OH; more preferably both $R_{28}$ and $R_{29}$ are H;

$R_{32}$ is H, OH or =O; preferably $R_{32}$ is H or OH; most preferably $R_{32}$ is H; and $R_{33}$ is H, or $R_{33}$ and $R_{15}$ taken together are =O, or $R_{33}$ and $R_{14}$ taken together represent the second bond of a double bond joining adjacent carbon atoms; preferably $R_{33}$ is H or $R_{33}$ and $R_{14}$ taken together represent the second bond of a double bond joining adjacent carbon atoms;

MS is selected from a group consisting of arabinose, xylose, lyxose, ribose, glucose, mannose, galactose, allose, altrose, gulose, idose, talose, ribulose, xylulose, fructose, sorbose, tagatose, psicose, sedoheptulose, deoxyribose, fucose, rhamnose, 2-deoxy-glucose, quinovose, abequose, glucosamine, mannosamine, galactosamine, neuraminic acid, muramic acid, N-acetyl-glucosamine, N-acetyl-mannosamine, N-acetyl-galactosamine, N-acetylneuraminic acid, N-acetylmuramic acid, O-acetylneuraminic acid, N-glycolylneuraminic acid, fructuronic acid, tagaturonic acid, glucuronic acid, mannuronic acid, galacturonic acid, iduronic acid, sialic acid and guluronic acid; preferably MS is selected from a group consisting of glucose, galactose, mannose, fucose, N-acetyl-glucosamine, N-acetyl-galactosamine and sialic acid; most preferably MS is glucose; and Y is N or O; preferably Y is O.

Preferred steroidal sapogenins of the formula VII are those in which $R_{21}$ is of the formula VIII and Y is O.

More preferred steroidal sapogenins of the formula VII are those in which:

$R_{12}$ is H, —OH
$R_{13}$ is H or —OH;
$R_{14}$ is H, or —OH or $R_{14}$ and $R_{33}$ taken together represent the second bond of a double bond joining adjacent carbon atoms;
$R_{15}$ is H, or $R_{15}$ and $R_{33}$ taken together are =O;
$R_{18}$ is H, —OH or $C_{1-6}$ alkoxy
$R_{19}$ is $C_{1-6}$ alkyl;
$R_{20}$ is H, —OH or $C_{1-6}$ alkoxy;
$R_{28}$ is H;
$R_{32}$ is H, —OH or =O; and
$R_{33}$ is H, or $R_{33}$ and $R_{15}$ taken together are =O, or $R_{33}$ and $R_{14}$ taken together represent the second bond of a double bond joining adjacent carbon atoms.

Most preferred are steroidal sapogenins of the formula VII in which:

$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$ is H or —OH;
$R_{18}$ is H or —OH;
$R_{19}$ is H, or $C_{1-6}$ alkyl;
$R_{21}$ is of the formula VIII;
$R_{22}$ is H, —OH, or $C_{1-6}$ alkoxy;
$R_{24}$ is $C_{1-6}$ alkyl, $C_{1-6}$ acyl, or glucose;
$R_{29}$ is H or —OH; and
$R_{32}$ is H or —OH.

The most preferred steroidal sapogenins of the formula VII are those in which $R_{12}$, $R_{13}$, $R_{15}$, $R_{16}$, $R_{17}$, $R_{22}$, $R_{28}$ each represent H;
$R_{14}$ is H, or $R_{14}$ and $R_{33}$ taken together represent the second bond of a double bond joining adjacent carbon atoms;

$R_{20}$ is —OH or $C_{1-6}$ alkoxy;
$R_{21}$ is of the formula VIII;
$R_{23}$ is —CH$_3$ or =CH$_2$;
$R_{24}$ is $C_{1-6}$ acyl or glucose;
$R_{29}$ is H or —OH; and
$R_{32}$ is H.

The most preferred steroidal sapogenins of the formula VII are selected from the group consisting of:

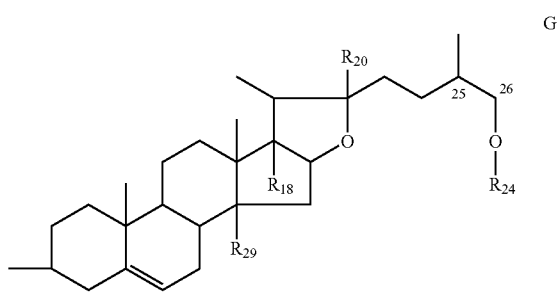

G

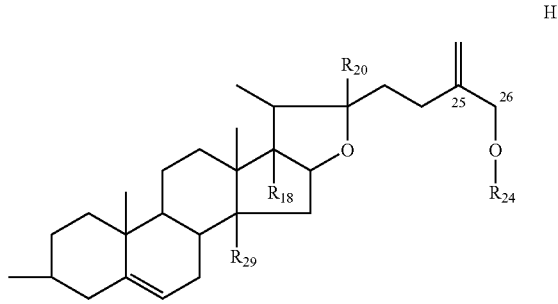

H

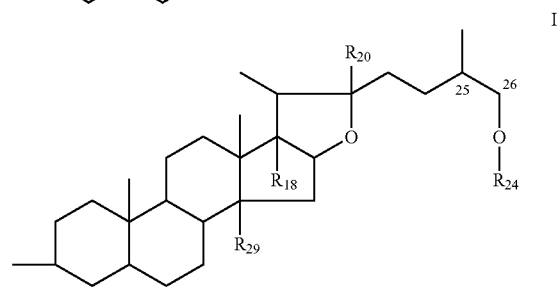

I

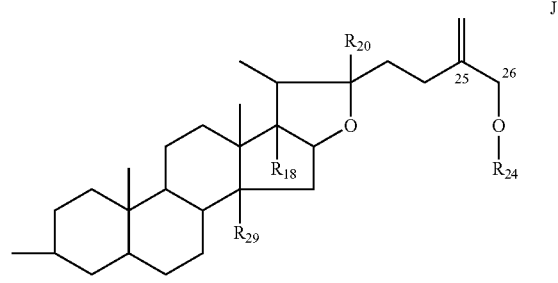

J wherein:
$R_{18}$ is H or OH;
$R_{20}$ is OH or $C_{1-6}$ alkoxy;
$R_{24}$ is glucose or $C_{1-6}$ acyl; and
$R_{29}$ is H or OH.

Particularly preferred compounds of the formula I in which the steroid group is of the formula VII are trigoneoside IVa, glycoside F, shatavarin I, compound 3, pardarinoside C, whose structures are summarised in Table 1.

TABLE 1

Structural details of trigoneoside IVa, glycoside F, shatavarin I, compound 3 and pardarinoside C

| Compound | Ref. | Steroid group | $R_{18}$ | $R_{20}$ | $R_{29}$ | $C^{25}$ | R/S | $C^{26}$ |
|---|---|---|---|---|---|---|---|---|
| Trigoneoside IVa | 55 | G | H | —OH | H | —$CH_3$ | S | Glc |
| Glycoside F | 55 | G | H | —OH | H | —$CH_3$ | R | Glc |
| Shatavarin I | 56 | I | H | —OH | H | —$CH_3$ | S | Glc |
| Compound 3 | This document | H | H | —OH | H | =$CH_2$ | ? | Glc |
| Pardarinoside C | 57 | I | OH | —OMe | —OH | —$CH_3$ | R | acetyl |

In each case the saccharide group bonded to the steroid group at the 3-position is:

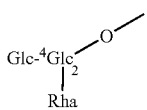

Alternatively the steroid group may be a steroidal sapogenin of the formula VIII:

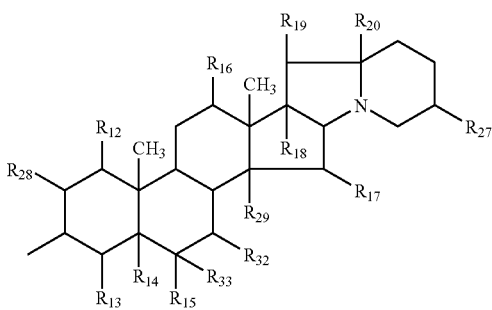

IX wherein:

$R_{12}$ is H, —OH, $C_{1-6}$ alkyl or $C_{1-6}$ alkoxy; preferably $R_{12}$ is H or —OH; most preferably $R_{12}$ is H;

$R_{13}$ is H, —OH, =O, or $C_{1-6}$ alkyl; preferably $R_{13}$ is H or —OH; most preferably $R_{13}$ is H;

$R_{14}$ is H —OH or $C_{1-6}$ alkyl or $R_{14}$ and $R_{33}$ taken together represent the second bond of a double bond joining adjacent carbon atoms; preferably $R_{14}$ is H or $R_{14}$ and $R_{33}$ taken together represent the second bond of a double bond joining adjacent carbon atoms;

$R_{15}$ is H, or —OH, or $R_{15}$ and $R_{33}$ taken together are =O; preferably $R_{15}$ is H, or $R_{15}$ and $R_{33}$ taken together are =O; more preferably $R_{15}$ is H;

$R_6$ is H, —OH or =O; preferably $R_{16}$ is H or =O; more preferably $R_{16}$ is H;

$R_{17}$ is H, —OH or =O; preferably $R_{17}$ is H or —OH; more preferably $R_{17}$ is H;

$R_{18}$ is H, —OH, $C_{1-6}$ alkoxy or $C_{1-6}$ alkyl; preferably $R_{18}$ is H, —OH, $C_{1-6}$ alkoxy; more preferably $R_{18}$ is H or OH; most preferably $R_{18}$ is H;

$R_{19}$ is H, —OH, $C_{1-6}$ alkyl or $C_{1-6}$ alkoxy; preferably $R_{19}$ is H, OH, or $C_{1-6}$ alkyl; more preferably $R_{19}$ is $C_{1-6}$ alkyl; and particularly $R_{19}$ is —$CH_3$;

$R_{20}$ is H, —OH, $C_{1-6}$ alkoxy or $C_{1-6}$ alkyl; preferably $R_{20}$ is H, —OH, or $C_{1-6}$ alkoxy; more preferably $R_{20}$ is —OH or $C_{1-6}$ alkoxy; most preferably $R_{20}$ is —OH;

$R_{27}$ is H, —OH, $C_{1-6}$ alkyl, $C_{1-6}$ alkoxy or $C_{1-6}$ hydroxyalkyl; preferably $R_{27}$ is H, $C_{1-6}$ alkyl or $C_{1-6}$ alkoxy; more preferably $R_{27}$ is H or $C_{1-6}$ alkyl; most preferably $R_{27}$ is methyl, ethyl or propyl;

$R_{28}$ and $R_{29}$ are the same or different and are H or —OH; preferably both $R_{28}$ and $R_{29}$ are H;

$R_{32}$ is H, —OH or =O; preferably $R_{32}$ is H or —OH; most preferably $R_{32}$ is H; and $R_{33}$ is H, or $R_{33}$ and $R_{15}$ taken together are =O, or $R_{33}$ and $R_{14}$ taken together represent the second bond of a double bond joining adjacent carbon atoms; preferably $R_{33}$ is H or $R_{33}$ and $R_{14}$ taken together represent the second bond of a double bond joining adjacent carbon atoms.

Preferred steroidal sapogenins of the formula IX are those in which:

$R_{12}$ is H or —OH $R_{13}$ is H or —OH;

$R_{14}$ is H or —OH, or $R_{14}$ and $R_{33}$ taken together represent the second bond of a double bond joining adjacent carbon atoms;

$R_{15}$ is H or —OH $R_6$ is H, —OH or =O;

$R_{17}$ is H, —OH or =O;

$R_{18}$ is H or —OH $R_{27}$ is $C_{1-6}$ alkyl; and $R_{28}$ and $R_{29}$ are the same or different and each represent H or —OH;

$R_{32}$ is H, —OH or =O.

More preferably steroidal sapogenins of the formula IX are those in which:

$R_{12}$ is H or —OH $R_{13}$ is H or —OH;

$R_{14}$ is H or —OH, or $R_{14}$ and $R_{33}$ taken together represent the second bond of a double bond joining adjacent carbon atoms;

$R_{15}$ is H or —OH $R_{16}$ is H or =O;

$R_{17}$ is H, —OH;

$R_{18}$ is H or —OH;

$R_{27}$ is $C_{1-6}$ alkyl;

$R_{28}$ and $R_{29}$ are the same or different and each represent H or —OH; and $R_{32}$ is H or —OH.

More preferably steroidal sapogenins of the formula IX are those in of the general formula IXa:

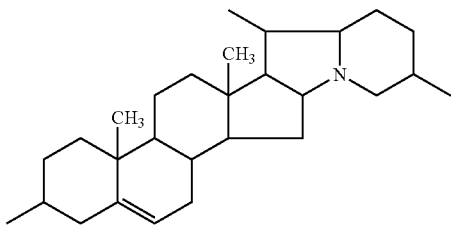

The most preferred compound of the formula I in which the steroid group is of the formula IX is:

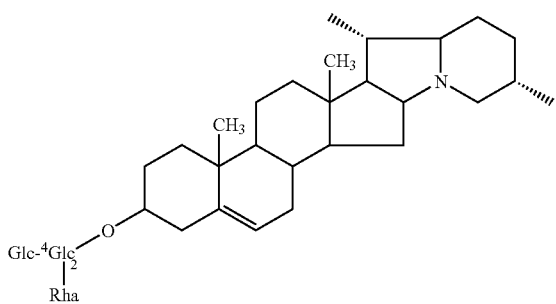

isolatable from *Lilium macklineae* (59).

A further preferred group of steroidal sapogenins are those in which the steroidal sapogenin is of the formula XI:

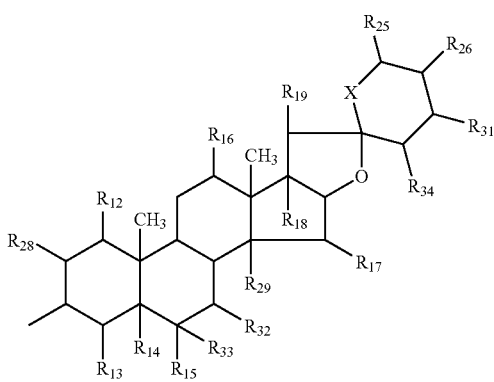

wherein:

$R_{12}$ is H, OH, $C_{1-6}$ alkyl or $C_{1-6}$ alkoxy; preferably $R_{12}$ is H or —OH; most preferably $R_{12}$ is H;—

$R_{13}$ is H, —OH, ═O, or $C_{1-6}$ alkyl; preferably $R_{13}$ is H or —OH; most preferably $R_{13}$ is H;—

$R_{14}$ is H, —OH or $C_{1-6}$ alkyl or $R_{14}$ and $R_{33}$ taken together represent the second bond of a double bond joining adjacent carbon atoms; preferably $R_{14}$ is H or $R_{14}$ and $R_{33}$ taken together represent the second bond of a double bond joining adjacent carbon atoms;—

$R_{15}$ is H, or —OH, or $R_{15}$ and $R_{33}$ taken together are ═O; preferably $R_{15}$ is H, or $R_{15}$ and $R_{33}$ taken together are ═O; more preferably $R_{15}$ is H;—$R_{16}$ is H, —OH or ═O; preferably $R_{16}$ is H or ═O; more preferably $R_{16}$ is H;

$R_{17}$ is H, —OH or ═O; preferably $R_{17}$ is H or —OH; more preferably $R_{17}$ is H;

$R_{18}$ is H, —OH, $C_{1-6}$ alkoxy or $C_{1-6}$ alkyl; preferably $R_{18}$ is H, OH, $C_{1-6}$ alkoxy; more preferably $R_{18}$ is H or —OH; most preferably $R_{18}$ is H;

$R_{19}$ is H, —OH, $C_{1-6}$ alkyl or $C_{1-6}$ alkoxy; preferably $R_{19}$ is H, —OH, $C_{1-6}$ alkyl; more preferably $R_{19}$ is H, —OH or $C_{1-6}$ alkyl; most preferably $R_{19}$ is $C_{1-6}$ alkyl; and particularly $R_{19}$ is —$CH_3$;

$R_{25}$ is H, —OH, $C_{1-6}$ alkyl or $C_{1-6}$ alkoxy; preferably $R_{25}$ is H or —OH; more preferably $R_{25}$ is H;

$R_{26}$ is H, —OH, $C_{1-6}$ alkyl, $C_{1-6}$ hydroxyalkyl, $C_{1-6}$-alkoxy-$C_{1-6}$-alkyl, ═$CH_2$ or ═CH—$C_{1-6}$-alkyl; preferably $R_{26}$ is $C_{1-6}$ alkyl, $C_{1-6}$ hydroxyalkyl, $C_{1-6}$-alkoxy-$C_{1-6}$-alkyl, ═$CH_2$ or ═$CHC_{1-6}$ alkyl; more preferably $R_{26}$ is $C_{1-6}$ alkyl, $C_{1-6}$ hydroxyalkyl or ═$CH_2$; most preferably $R_{26}$ is —$C_2H_4OH$, —$CH_2OH$, $C_{1-6}$ alkyl, or ═$CH_2$, even more preferably $R_{26}$ is —$C_2H_4OH$, —$CH_2OH$, —$C_2H_5$, —$CH_3$ or ═$CH_2$ and particularly $R_{26}$ is —$CH_3$ or ═$CH_2$;

$R_{28}$ and $R_{29}$ are the same or different and are H or —OH; preferably both $R_{28}$ and $R_{29}$ are H;

$R_{31}$ is H or —OH; preferably $R_{31}$ is H;

$R_{32}$ is H, —OH or ═O; preferably $R_{32}$ is H or —OH; most preferably $R_{32}$ is H;

$R_{33}$ is H, or $R_{33}$ and $R_{15}$ taken together are ═O, or $R_{33}$ and $R_{14}$ taken together represent the second bond of a double bond joining adjacent carbon atoms; preferably $R_{33}$ is H or $R_{33}$ and $R_{14}$ taken together represent the second bond of a double bond joining adjacent carbon atoms;

$R_{34}$ is H or —OH; preferably $R_{34}$ is H; and

X is O, S or NH; preferably X is O or NH; more preferably X is O.

Preferred steroidal sapogenins of the formula XI are those in which:

$R_{12}$ is H or —OH;

$R_{13}$ is H or —OH;

$R_{14}$ is H or —OH, or $R_{14}$ and $R_{33}$ taken together represent the second bond of a double bond joining adjacent carbon atoms;

$R_{15}$, $R_{18}$ $R_{28}$ and $R_{29}$ are the same or different and each represent H or —OH, $R_{16}$ is H, OH or ═O;

$R_{17}$ is H, —OH or ═O;

$R_{18}$ is H, —OH or $C_{1-6}$-alkoxy;

$R_{19}$ is H, or $C_{1-6}$ alkyl;

$R_{26}$ is H, $C_{1-6}$ alkyl, $C_{1-6}$ hydroxyalkyl, $C_{1-6}$-alkoxy-$C_{1-6}$-alkyl, ═$CH_2$ or ═CH—$C_{1-6}$-alkyl;

$R_{29}$ is H or —OH;

$R_{31}$ is H or —OH;

$R_{32}$ is H, —OH or ═O; and $R_{33}$ is H, or $R_{33}$ and $R_{15}$ taken together are ═O, or $R_{33}$ and $R_{14}$ taken together represent the second bond of a double bond joining adjacent carbon atoms; and $R_{34}$ is H or —OH.

More preferred steroidal sapogenins of the formula XI are those in which:

$R_{12}$, $R_{13}$, $R_{15}$ and $R_{28}$ each represent H;

$R_{14}$ is H, or $R_{14}$ and $R_{33}$ taken together represent the second bond of a double bond joining adjacent carbon atoms;

$R_{16}$ is H, or ═O;

$R_{17}$ is H or —OH;

$R_{18}$ is H or —OH;

$R_{19}$ is H, or $C_{1-6}$ alkyl;

$R_{26}$ is $C_{1-6}$ alkyl, $C_{1-6}$ hydroxyalkyl or ═$CH_2$;

$R_{28}$ is H;

$R_{29}$ is H or —OH;

$R_{32}$ is H or —OH; and $R_{33}$ is H, or $R_{33}$ and $R_{14}$ taken together represent the second bond of a double bond joining adjacent carbon atoms.

Most preferred steroidal sapogenins of the formula XI are those in which:

$R_{12}$, $R_{13}$, $R_{15}$, $R_{16}$, $R_{17}$, $R_{25}$, $R_{28}$, $R_{31}$, $R_{32}$ and $R_{34}$, each represent H;

$R_{14}$ is H, or $R_{14}$ and $R_{33}$ taken together represent the second bond of a double bond joining adjacent carbon atoms;

$R_{18}$ is H or —OH;

$R_{19}$ is $C_{1-6}$ alkyl;

$R_{26}$ is $C_{1-6}$ alkyl or =$CH_2$;

$R_{29}$ is H or —OH;

$R_{32}$ is H;

$R_{33}$ is H, or $R_{33}$ and $R_{14}$ taken together represent the second bond of a double bond joining adjacent carbon atoms.

The most preferred steroidal sapogenins of the formula XI are those selected from the groups:

A
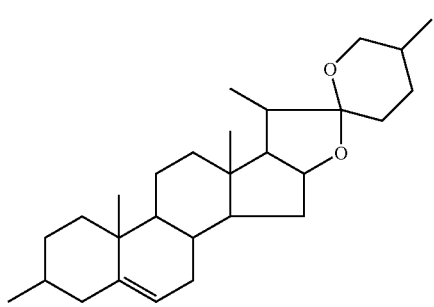

B
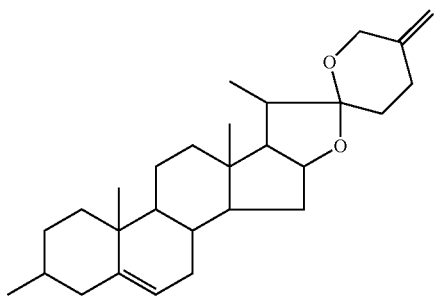

C
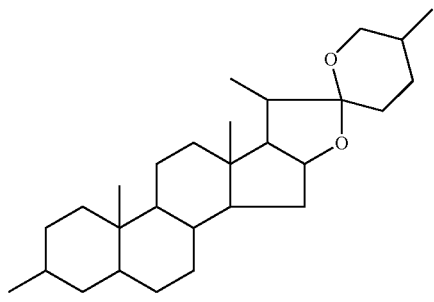

D
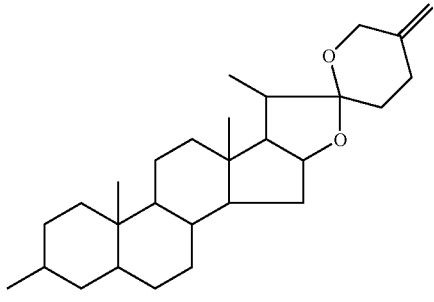

E
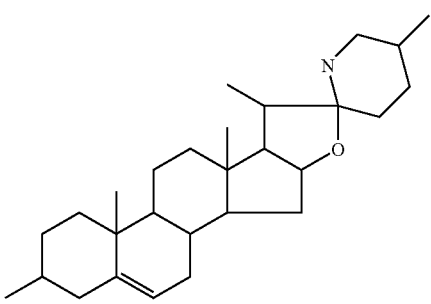

F
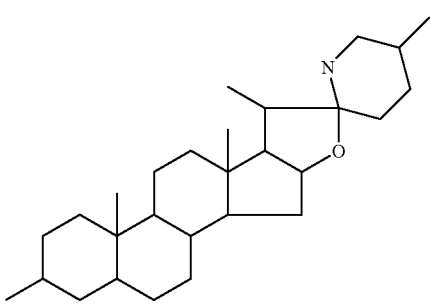

Particularly preferred steroidal sapogenins of the formula XI are diosgenin, yamogenin, tigogenin, neotigogenin, sarsasapogenin, smilagenin, hecogenin, solasodine or tomatidine.

Particularly preferred compounds of the formula I in which the steroidal group is of the formula XI are:

Shatavarin IV, (25R)shatavarin IV, deltonin, balanitin VI, compound 12 of Mimaki and Sahida (58).

Shatavarin IV is sarsasapogenin 3-O-α-L-rhamnopyranosyl-(1→2)-O-[β-D-glucopyranosyl-(1→44)]-β-D-glucopyranoside Compound 12 is solasodine 3-O-α-L-rhamnopyranosyl-(1→2)-O-[β-D-glucopyranosyl-(1→4)]-β-D-glucopyranoside Deltonin is (3β,25R)-spirost-5-en-3-yl-O-α-L-rhamnopyranosyl-(1→2)-O-[β-D-glucopyranosyl-β-D-Glucopyranoside.

Balanitin VI is (3β,25S)-spirost-5-en-3-yl-O-α-L-rhamnopyranosyl-(1→2)-O-[β-D-glucopyranosyl-β-D-Glucopyranoside.

Particularly preferred compounds of the formula I are those combining preferred steroid groups with preferred saccharide groups.

In a second aspect of the invention is provided the use of the compounds of the formula I in the manufacture of a medicament for the treatment of conditions associated with raised activity of the enzyme core 2 GlcNAc-T. Examples of such conditions are described herein in the first aspect of the invention.

In a third aspect of the invention is provided pharmaceutical compositions comprising the compounds of the formula I.

As used herein the term core 2 GlcNAc-T inhibitor means and inhibitor of the enzyme core 2-GlcNAc-T and preferably the ability of preparations comprising a core 2 GlcNAc-T enzyme activity described herein to incorporate UDP-6 [³H]-N-acetyl-glucosamine into products as measured in the assays described herein.

As used herein the term aglycone refers to compounds of the formula I wherein the saccharide moieties are not present. The compounds may have other substituents at the position occupied by the saccharide moiety. Particularly aglycones that are furostanol saponins when glycosylated may be in the ring closed state as the equivalent spirostanol saponins.

The shorthand annotation:

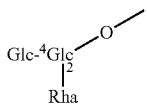

used in structures herein is used to denote the structure:

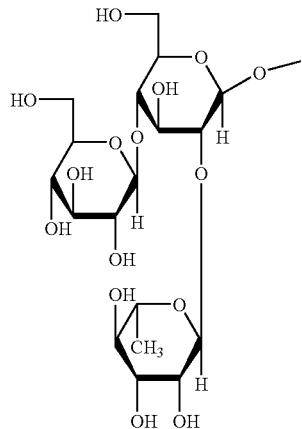

The short hand annotation:

used in structures herein denotes the structure:

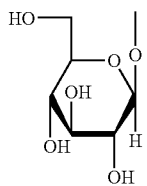

As used herein the shorthand annotation Glc is glucose and Rha is rhamnose.

For the avoidance of doubt the term $C_{1-6}$ acyl is —CO—CO—$C_{1-5}$-alkyl.

Figure 1:
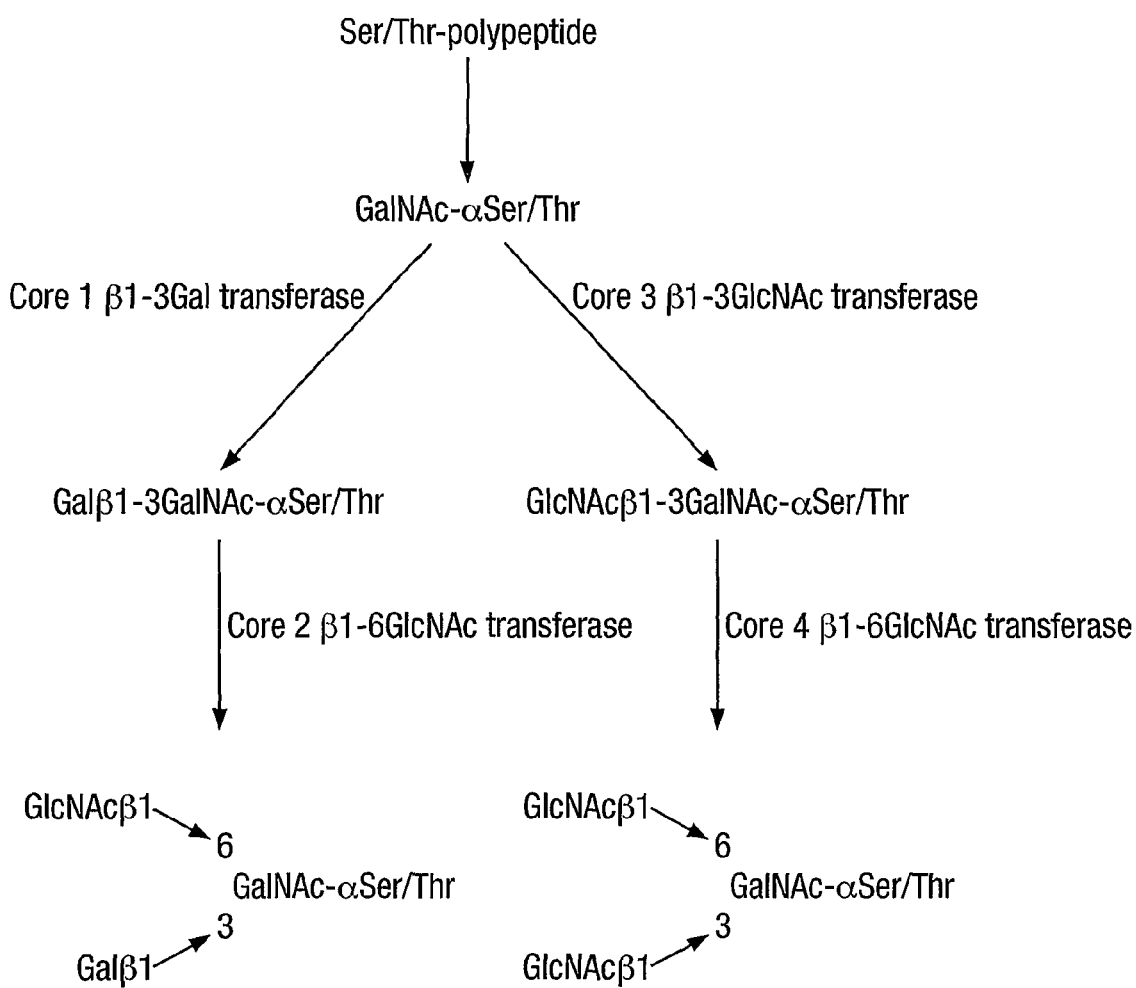
FIG. 1 is a schematic flow chart illustrating the biosynthesis of O-glycan core structures.

In cell free assays heart lysate from BB rats were incubated in the presence, and absence of 20 ng/ml of each compound. After 1 h incubation at 37° C., the activity of core 2 GlcNAc-T was measured, and expressed as pmoles/h/mg protein. The results are the mean of 3-5 separate experiments.

In cell based assays human leukocytes (U937 cells) were exposed to 8 pg/ml human recombinant TNF-alpha in the presence and absence of 20 ng/ml of the test compound. After 24 h incubation, the activity of core 2 GlcNAc-T was measured, and expressed as pmoles/h/mg protein.

The invention will now be described by reference to the following non limiting reference examples, figures and tables. Further embodiments falling within the scope of the claims will occur to those skilled in the art in the light of these.

DETAILED DESCRIPTION OF THE INVENTION

Experimental Methods

Compounds of the formula I can be extracted from a variety of plant species. Reference is made in this respect, and by way of example only, to Yoshikawa et al (55), Sasheda et al (59), Akhov et al (60), Joshi and Dev (61), Ravikumar et al (56), Vasil'eva and Paseshnichenko (62), Shimomura et al (57), Sharma and Sharma (63), Petit et al (64), Mimaki and Sashida (58), and Hostettman (65) and references therein). These documents are all incorporated herein by reference.

Alternatively, they can be synthesised by conventional organic chemistry methods and techniques. Reference in this respect is made to carbohydrate and steroid chemistry textbooks such as "Essentials of Carbohydrate Chemistry and Biochemistry" by Thisbe K. Lindhorst (2000) Wiley, "Carbohydrates in Chemistry and Biology" edited by Beat Ernst, Gerald W. Hart and Pierre Sinay (2000) Wiley, "Essentials of Carbohydrate Chemistry" by John F. Robyt (1998) Springer Verlag, "Carbohydrate Chemistry" by Hassan S. El Khadem (1988), "Carbohydrate Building Blocks" by Mikael Bols (1996), "Glycochemistry: Principles, Synthesis, and Applications" edited by P. G. Wang and C. R. Bertozzi (2001) Marcel Dekker, N.Y. and "Carbohydrate Chemistry" by the Royal Society of Chemistry Staff (1989) CRC Press.

The compounds of the present invention can be prepared from commercially available aglycones or by isolation of the aglycone or other precursor either from fenugreek seeds or from another plant source and subsequent chemical modification of the precursor.

The skilled worker will for example be aware of many sources of spirostanol and furostanol aglycones such as diosgenin, yamogenin, tigogenin, neotigogenin, sarsapogenin, smilagenin, hecogenin, solasodine or tomatidine (for example Hostettman and references therein (65)), Specifically for methods of synthesis of spirostanol saponins having 2, 4 branched oligosaccharide moieties, from diosgenin see Du et al 2003 (73). This reference also makes further reference to the synthesis if other glycosylated steroids, for example from cholesterol. The methods disclosed can be used to synthesize compounds in which steroids are chemically glycosylated to form compounds of the formula I.

Further reference is made to Li et al (66) for synthesis of a trisaccharide substituted spirostanol saponins, Deng et al (67), for synthesis of a variety of tri and tetra saccharide substituted spirostanol saponins, Li et al (68), Yu et al (69), Yu et al (70) for methods of synthesis of furostanol saponins and interconversion of spirostanol and furostanol saponins, Yu and Tao (71), Cheng et al (72) and Du et al (73). These references also provide information and further references on derivatisation of monosaccharide hydroxyalkyl groups.

Methods of synthesising Galβ1-3(6deoxy)GalNAcα-conjugates are given in Paulsen et al (48). These methods may be adapted by the skilled worker in combination with other methods referenced herein to synthesize other compounds of the formula I.

Cell Culture

Bovine retinal capillary endothelial cells (BREC) and pericytes (BRP) were established from bovine retinas dissected from eyes of freshly slaughtered cattle as described previously (48). Briefly, the isolated retinas were homogenised in serum-free minimal essential medium (MEM, Gibco, Paisley, UK) and filtered through 85 μm nylon mesh. The trapped microvessels were digested with collagenase-dispase (1 mg/ml) for 30 minutes (BRP) and 90 minutes (BREC) at 37° C. and filtered through a 53 μm nylon mesh. For growth of endothelial cells (BREC), the digested microvessels were plated in gelatine coated tissue culture flasks and maintained in MEM supplemented with 10% pooled human serum, 2 mM glutamine, 100 IU/ml penicillin and 100 µg/ml streptomycin. For growth of pericytes (BRP), the microvessels were plated in tissue culture flasks in growth medium supplemented with 10% foetal calf serum. The cells were used at passage 2-3. The cells were characterised using morphological criteria and by immunostaining with an antibody against factor VIII related antigen and 3G5-pericyte marker.

The human leukocytic cell-line (U937) was cultured in RPMI supplemented with 10% foetal calf serum, 2 mM glutamine, 100 IU/ml penicillin and 100 µg/ml streptomycin.

Cell-Based Assay of Core 2 GlcNAc-T Activity

To investigate the potential of fenugreek to pharmacologically inhibit core 2 GlcNAc-T, enzyme activity was measured in leukocytes exposed to normal glucose (5.8 mM) and high glucose (15 mM) for 24 hours at 37° C. After incubation, the cells were lysed and frozen at $-20°$ C. until used for the measurement of core 2 GlcNAc-T. The activity of core 2 GlcNAc-T in cultured bovine retinal capillary pericytes (BRP) and endothelial cells (BREC) was also measured.

Cell-Free Assay of Core 2 GlcNAc-T Activity

Core 2 GlcNAc-T immobilised on Sepharose beads were used for this assay. For core 2 GlcNAc-T immunoprecipitation, as well as for Western blots, a polyclonal antibody against core 2 GlcNAc-T was used. Cells were lysed on ice in the following lysis buffer: 20 mM Tris-HCL, pH 7.4/1% Triton X-100, 150 mM NaCl, 1 mM EDTA, 1 mM EGTA, 0.2 mM sodium vandate, 1 mM PMSF 1 µg/ml aprotinin, 10 µg/ml leupeptin. The lysate was incubated at 4° C. for 20 minutes with constant agitation and insoluble material removed by centrifugation (14,000 g for 5 minutes at 4° C.). The clarified lysate was incubated with staphylococcal protein A-Sepharose CL-4B conjugated primary antibody for 2 hours with constant agitation at 4° C. The immunoprecipitates were washed with Tris buffered saline (10 mM Tris-HCL, pH 7.4, 150 mM NaCl) containing 0.5% Triton X-100 and used in the measurement of core 2 GlcNAc-T in the presence and absence of potential inhibitors.

Measurement of Core 2 GlcNAc-T Activity:

To measure core 2 GlcNAc-T activity, leukocytes were washed in PES, frozen and lysed in 0.9% Triton X-100 at 0° C. The activity of core 2 GlcNAc-T was measured as described previously (41). Briefly, the reaction was performed in a reaction mixture containing 50 mM 2(N-morpholino)ethanesulfonic acid (MES, Sigma, Dorset, UK), pH 7.0, 1 mM UDP-6 ['H]-N-acetylglucosamine (16,000 dpm/nmol, NEN Life Science Products, Hounslow, UK), 0.1 M GlcNAc (Sigma, Dorset, Okla.), 1 mM Galβ1-3GalNAcα-p-nitrophenol (Sigma, Dorset, UK) as substrate, and 16 µl of cell lysate (100-200 µg protein) for a final volume of 32 µl. After incubating the mixture for 1 hour at 37° C., the reaction was terminated with 1 ml of ice-cold distilled water and processed on a C18 Sep-Pak column (WatersMillipore, Watford, UK). After washing the column with 20 ml of distilled water, the product was eluted with 5 ml of methanol. The radioactivity of the samples was counted in a liquid scintillation β-counter (LKB-Wallac, London, UK). Endogenous activity of core 2 GlcNAc-T was measured in the absence of the added acceptor. The specific activity was expressed as pmoles/h/mg of cell protein. In each case, the protein concentration was determined with BioRad protein assay (BioRad, Hertfordshire, UK).

Leukocyte-Endothelial Adhesion Assay

Adhesion of leukocytes to endothelial cells was examined by labelling with carboxyfluorescein (Molecular Probe, UK). The assay is well established (41). Briefly, endothelial cells were grown to a confluent state in order to provide an endothelial cell surface for the adhesion of the carboxyfluorescein-labelled leukocytes (U937). After treatment, the leukocytes were centrifuged (14 000 g for 1 minute) and washed twice with serum-free RPML The cells were then resuspended in 1 ml of serum-free RPMI containing 50 µg/ml carboxyfluorescein. The cells were counted with a haemocytometer and a known number added to the endothelial cells. After 30 minutes incubation at 37° C., non-adherent leukocytes were removed by washing with serum-free RPMI and the dishes fixed in 3.7% formalin in PBS. Attached leukocytes were counted in 10 random high-powered fields (×100) by fluorescence microscopy. The results were expressed as percentage of adherent leukocytes/field.

Glucose Toxicity

BRP and BREC were plated in 3 cm tissue culture dishes and incubated in growth medium for 24 hours at 37° C. Then the cells were incubated in fresh growth medium containing normal glucose (5.8 mM) or elevated glucose (25 mM) in the absence or presence of fenugreek sub-fractions. After 4 days incubation, the number of viable cells was counted using a haemocytometer and trypan blue and the results expressed as percentage of control (5.8 mM glucose). After treatment, some of the cells were stored for measurement of core 2 GlcNAc-T activity.

Biological Activity of Crude Fenugreek Seed Extract

Figure 2A:
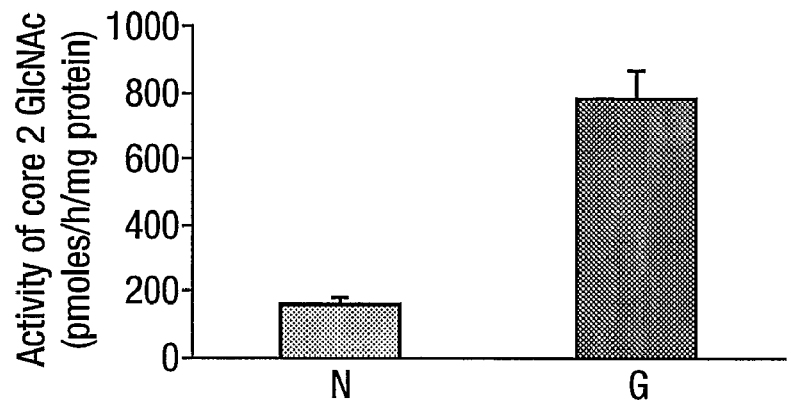
FIG. 2a is a graph illustrating that the activity of the enzyme core 2 GlcNAc-T can be induced by glucose. Human leukocytes (U937) were exposed to normal (5.8 mM) and high glucose (15 mM) for 24 hours at 37° C. Then the cells were lysed and the activity of core 2 GlcNAc-T measured. The data is presented as the means±s.e.m., n=28, the asterisk representing a significant difference (P<0.05).
Figure 2B:
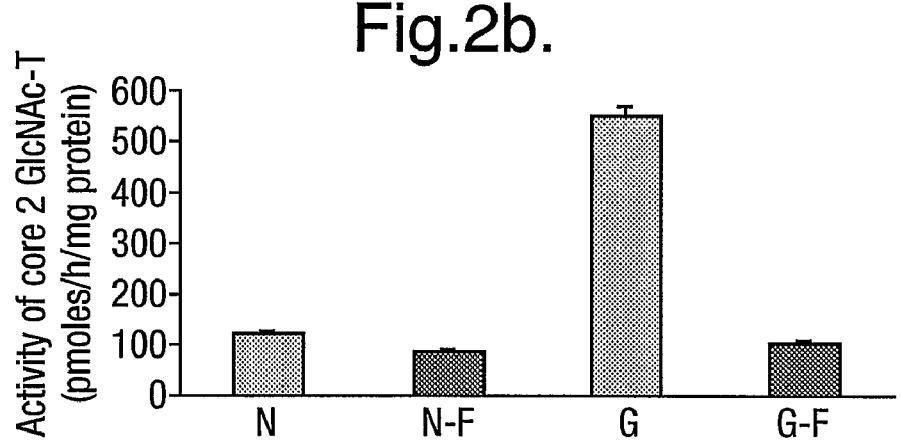
FIG. 2b is a graph illustrating that crude extract F1 prepared from fenugreek seeds inhibits glucose-induced core 2 GlcNAc-T activity. Human leukocytes (U937) were exposed to normal (N, 5.8 mM; n=3) and high glucose (G, 15 mM; n=3) in the presence of fenugreek extract (1:1000 dilution; N-F, G-F). After 24 hours incubation, the activity of core 2 GlcNAc-T was determined in leukocyte cell lysates. The activity of core 2 GlcNAc-T is presented as pmoles/h/mg protein.
Figure 2C:
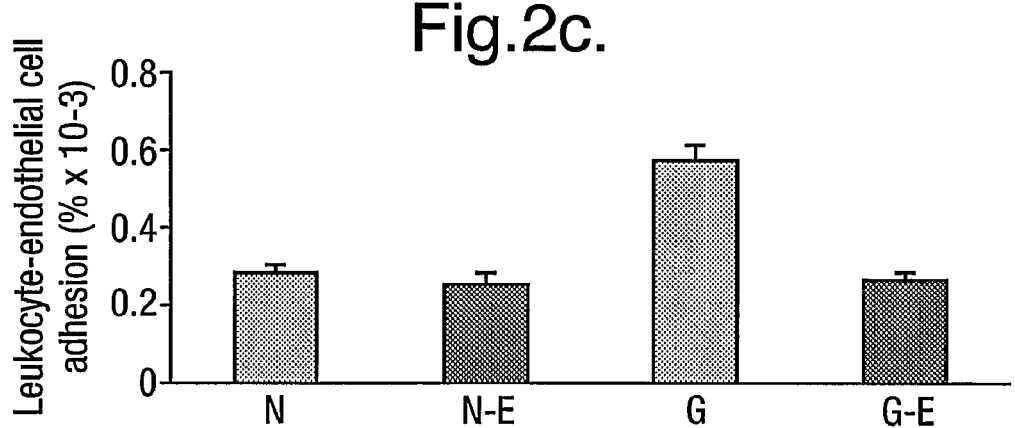
FIG. 2c is a graph illustrating that crude extract F1 prepared from fenugreek seeds inhibits adherence of human leukocytes (U937) to cultured retinal capillary endothelial cells. After exposure to elevated glucose (15 mM) the level of leukocyte-endothelial cell adhesion was determined by labelling the leukocytes with carboxyfluorescein. The data is presented as the mean±s.e.m., n=3, the asterisk representing a significant difference (P<0.05).

As shown in FIG. 2a, 24 hour exposure to elevated D-glucose significantly increases the activity of core 2 GlcNAc-T in human leukocytes (U937). It has now been found that crude extract prepared from fenugreek seeds has the potential to inhibit glucose-induced activity of core 2 GlcNAc-T in human leukocytes (FIG. 2b) and leukocyte-endothelial cell adhesion (FIG. 2c). Leukocyte-endothelial cell adhesion was measured by adding a known number of leukocytes stained with carboxyfluorescein to a monolayer of retinal capillary endothelial cells. The number of attached leukocytes was then counted under a fluorescence microscope using 10-random fields.

Figure 3:
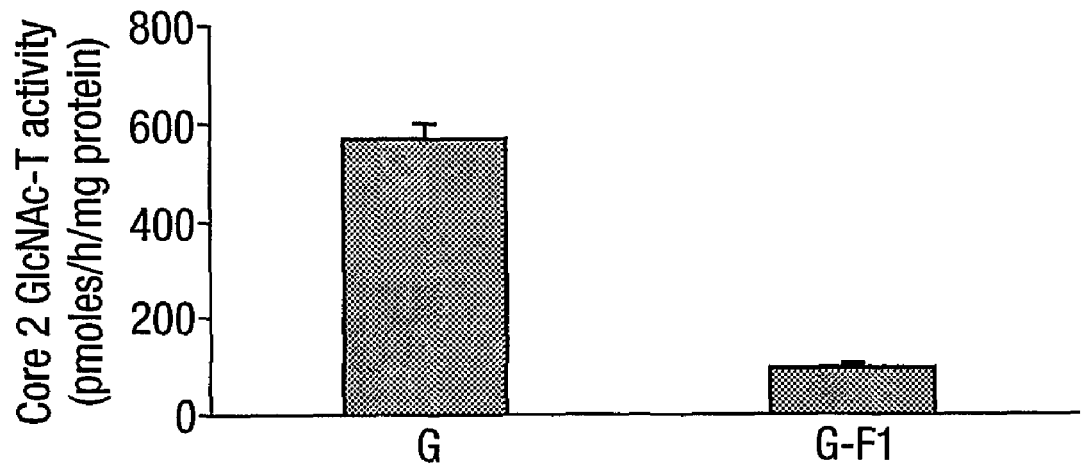
FIG. 3 is a graph illustrating that crude extract F1 prepared from fenugreek seeds inhibits core 2 GlcNAc-T activity. Human leukocytes (U937) were exposed to 15 mM glucose for 24 hours at 37° C. and the activity of core 2 GlcNAc-T was measured in leukocyte cell lysate in the presence of crude fenugreek seed extract (G-F1; 1:1000 dilution). The level of core 2 GlcNAc-T activity was measured by determining the formation of core 2 oligosaccharide (attachment of β1,6-linked GlcNAc to the Galβ1,3GlcNAc-acceptor). The data is presented as mean±s.e.m. of three separate experiments.

The results illustrated in FIG. 3 were obtained by exposing human leukocytes (U937) to elevated glucose for 24 hours. The cells were then lysed, incubated with crude fenugreek seed extract F1 and core 2 GlcNAc-T activity was measured after 30 minutes incubation.

Preparation and Purification of Fenugreek Seed Extracts: Example 1

Figure 4:
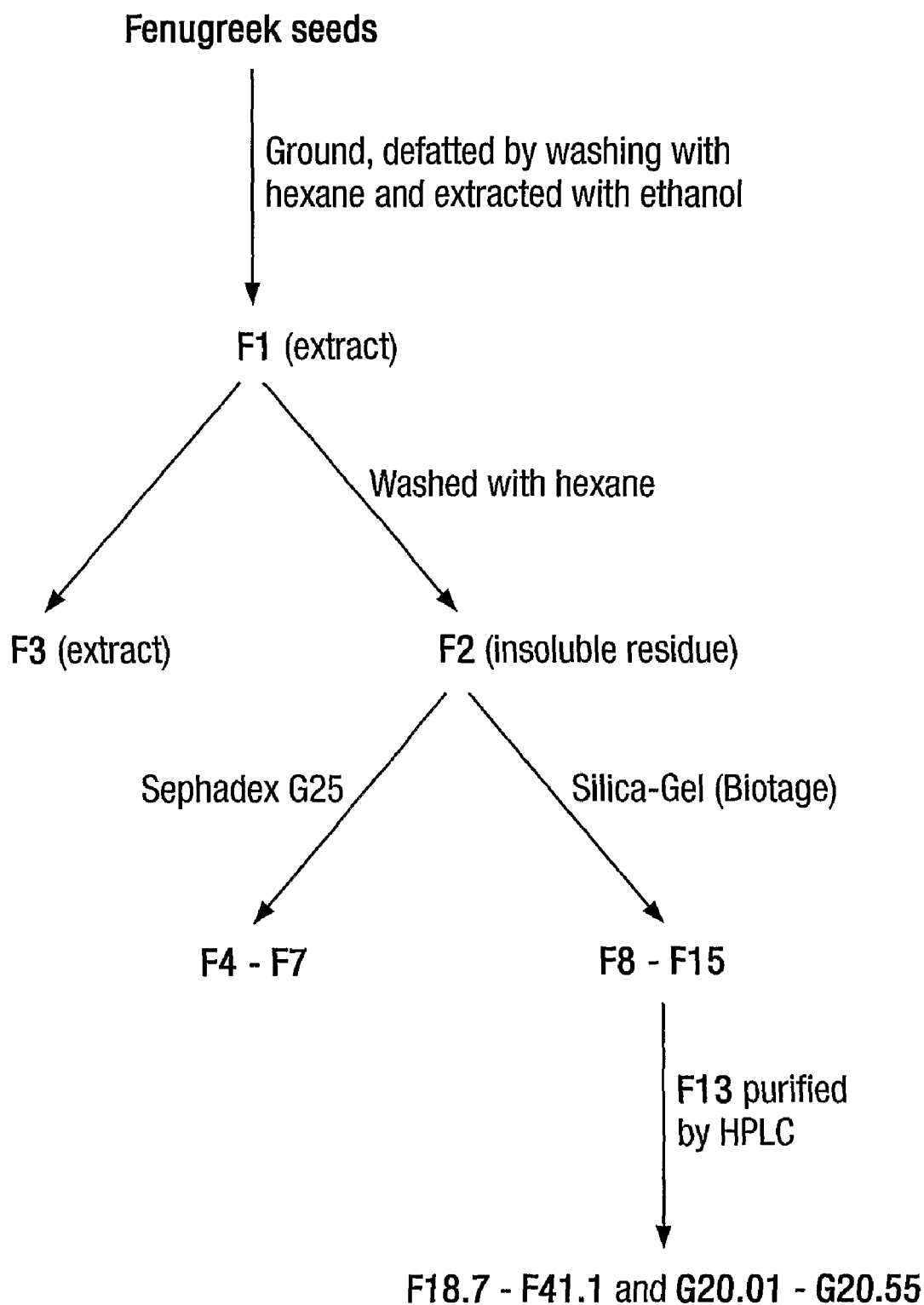
FIG. 4 is a schematic flow chart illustrating the extraction of fenugreek seeds and the subsequent purification of the fenugreek seed extract.

Fenugreek seed extracts were obtained as follows (see FIG. 4). Fenugreek seeds (Indian fenugreek seeds obtained as Methi seeds from FUDCO, 184 Ealing Road, Wembley, Middlesex, UK) were ground in a hammer mill and filtered through nylon mesh. 820 g of the dark-yellow powder obtained were defatted by continuous washing with hexane in a soxhlet apparatus for eight hours. Then the plant material was dried and continuously extracted for 8 hours with ethanol. Filtration to remove solid residues and concentration in vacuo of the ethanol yielded a semi-solid brown crude extract labelled F1 (65 g). Since this appeared to contain residual oil, 50 g of the crude extract F1 were shaken with cold hexane (500 ml). The hexane soluble material was filtered off and the solvent removed to give F3 (15.4 g), while the insoluble residue was collected on the filter paper and dried to give F2 (27 g).

Normal phase silica-gel flash chromatography was now employed using a commercial kit (Biotage). F2 (5 g) was adsorbed onto silica-gel (5 g) and packed into the sample barrel that was connected by short tubing to the main chromatography column (20 cm×4 cm) containing silica-gel KP- Sil. The sample was eluted onto and through the column with a succession of solvents of increasing polarity consisting of varying mixtures of light petroleum (40/60), chloroform, methanol and acetone. Eluting sub-fractions were examined by TLC and similar ones pooled to give seven main eluted sub-fractions F8 to F14 representing compounds of increasing polarity. The silica was removed and shaken with 100% methanol, filtered and dried to give a residue labelled F15. Weights and approximate elution solvents for each sub-fraction are set out in Table 2.

TABLE 2

Separation of sub-fraction F2 into sub-fractions F8-F15 using flash chromatography

| Sub-fraction | Weight | Eluent |
|---|---|---|
| F8 | 0.03 g | light petroleum (40/60) 100% to chloroform 100% |
| F9 | 0.10 g | chloroform:methanol 90:10 |
| F10 | 0.02 g | chloroform:methanol from 90:10 to 80:20 |
| F11 | 0.03 g | chloroform:methanol from 80:20 to 70:30 |
| F12 | 0.82 g | chloroform:methanol from 70:30 to 60:40 |
| F13 | 1.58 g | chloroform:methanol 50:50 |
| F14 | 0.01 g | chloroform:methanol:acetone 30:30:40 to acetone 100% |
| F15 | 0.14 g | eluted from silica-gel with methanol |

Biological Activity of Purified Fenugreek Seed Extracts

Figure 5:
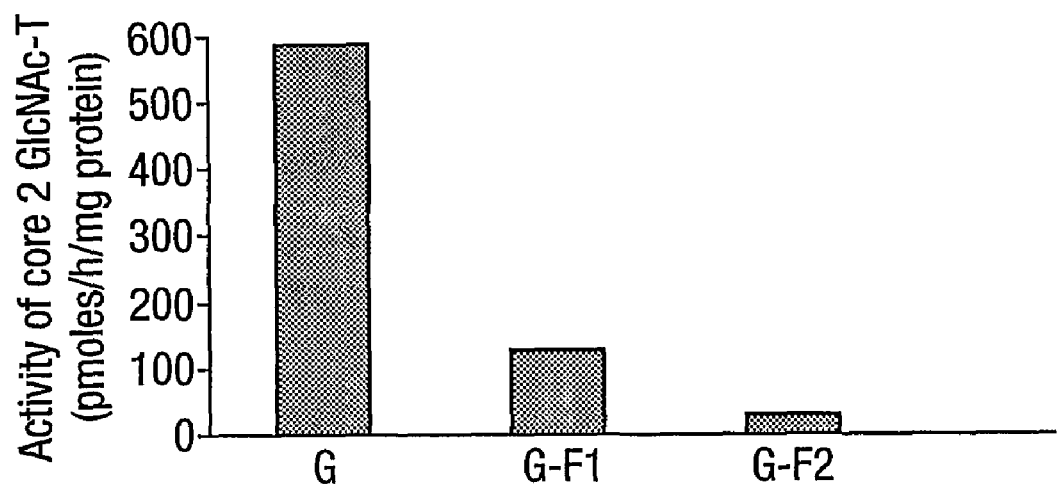
FIG. 5 is a graph illustrating the inhibitory effect of crude fenugreek seed extract F1 and sub-fraction F2 purified from crude extract F1 on glucose-induced activity of core 2 GlcNAc-T in human leukocytes (U937). Cells were exposed to elevated glucose (15 mM) in the presence and absence of sub-fractions F1 and F2. After 24 hours incubation, the core 2 GlcNAc-T activity was determined in leukocyte cell lysates. The data represents the mean of two separate experiments.
Figure 6A:
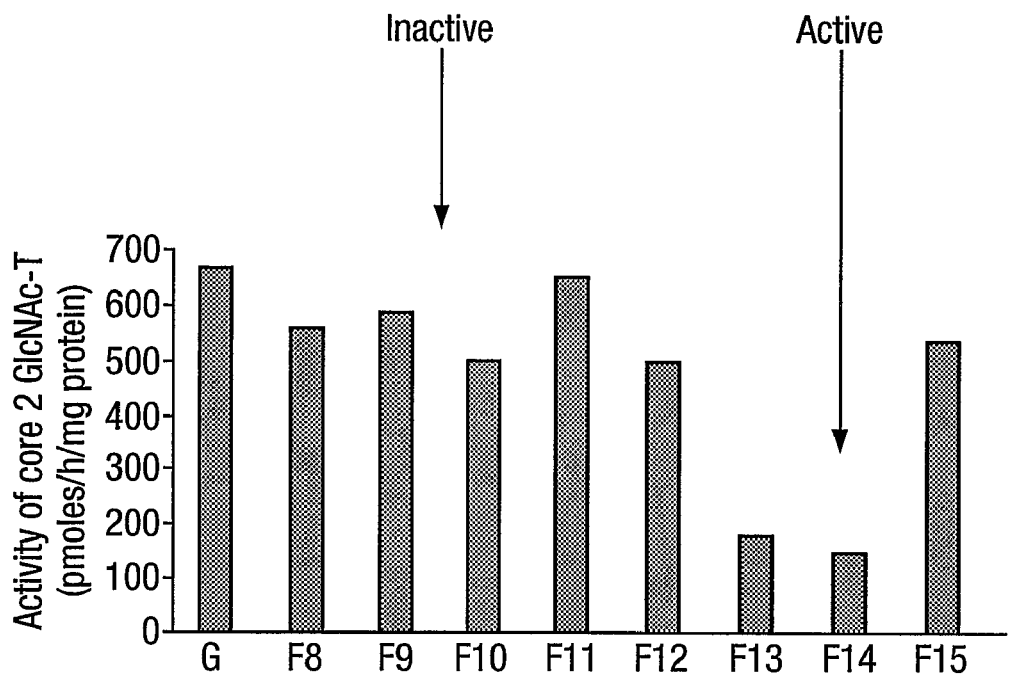
FIGS. 6a and 6b are graphs illustrating the inhibitory effect of sub-fractions F8-F15 purified from crude extract F1 by silica-gel flash chromatography (Biotage) on glucose induced activity of core 2 GlcNAc-T in human leukocytes (U937). Cells were exposed to elevated glucose (G, 15 mM) in the presence of the sub-fractions. After 24 hours incubation, the core 2 GlcNAc-T activity was determined in leukocyte cell lysates. The data is presented as the mean±s.e.m., n=3, the asterisk representing a significant difference (P<0.05).
Figure 6B:
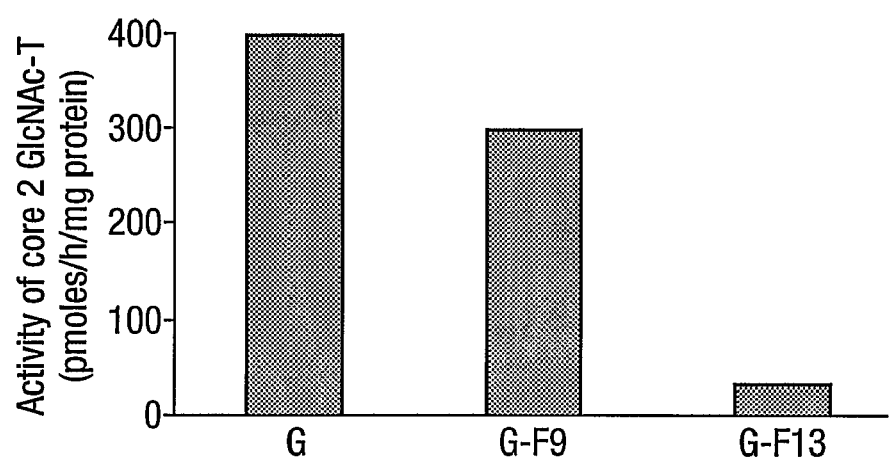

The potential of these purified sub-fractions to inhibit glucose-induced activity of core 2 GlcNAc-T in leukocytes was examined. Firstly, it was demonstrated that sub-fraction F2 can inhibit glucose-induced core 2 GlcNAc-T activity in leukocytes (FIG. 5). Further experiments demonstrated the presence of the inhibitor of core 2 GlcNAc-T in sub fractions F13 and F14 (FIGS. 6a and 6b).

Figure 7:
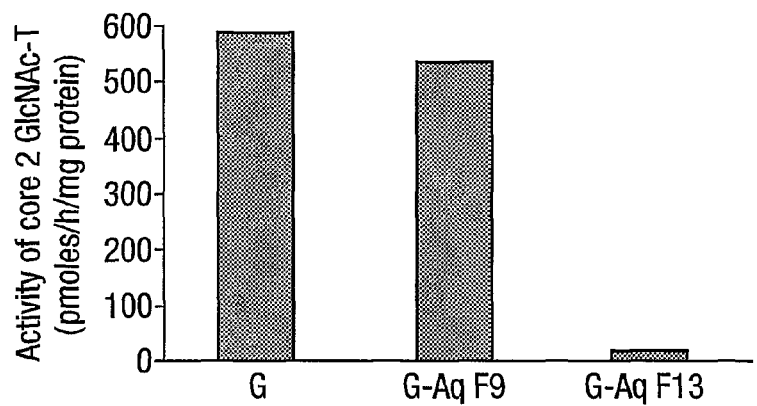
FIG. 7 is a graph illustrating that the aqueous phase of sub-fraction F13 inhibits glucose induced activity of core 2 GlcNAc-T in human leukocytes (U937). Sub-fractions F9 and F13 were thoroughly mixed with dichloromethane and the aqueous phase was filter sterilised and used in the cell-based assay for core 2 GlcNAc-T activity. Human leukocytes were exposed to elevated D-glucose (15 mM) in the presence and absence of the aqueous phases of sub-fractions F9 and F13. The results are presented as the mean of two separate experiments.

Sub-fractions F9 and F13 were then analysed. An aqueous aliquot (0.5 ml) of both subfractions F9 and F13 was extracted with 1 ml of dichloromethane, the aqueous phase was removed, filter-sterilised by filtration through 0.22 μm filter and used in the cell-based assay for core 2 GlcNAc-T activity. Human leukocytes were exposed to elevated D-glucose (15 mM) in the presence and absence of the aqueous phases of sub-fractions F9 and F13, The results are presented in FIG. 7 showing the presence of the core 2 GlcNAc-T inhibitor in the aqueous phase of sub-fraction F13.

Figure 8:
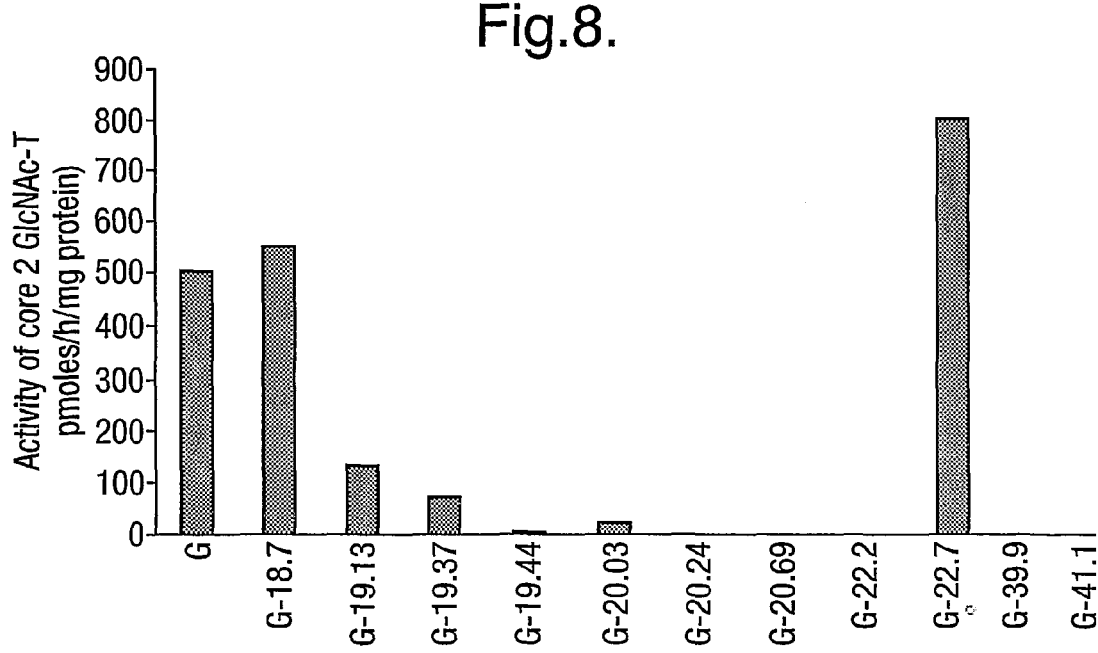
FIG. 8 is a graph illustrating the inhibitory effect on glucose-induced activity of core 2 GlcNAc-T of sub-fractions purified from the aqueous phase of sub-fraction F 13 by HPLC with retention times F18.7-F41.1. Human leukocytes (U937) were exposed to elevated D-glucose (15 mM) in the presence and absence of the HPLC sub-fractions with retention times F18.7-F41.1. The data presented is from one experiment. Sub-fractions G20.24, G20.69, G22.2, G39.9 and G41.1 (represented without a column in FIG. 8) were not tested for their inhibitory effect on glucose-induced activity of core 2 GlcNAc-T.
Figure 9:
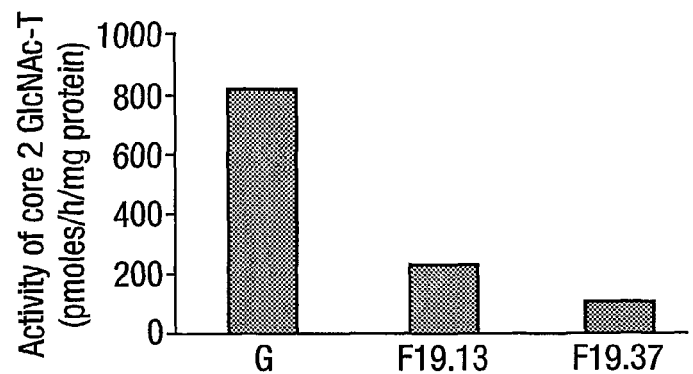
FIG. 9 is a graph illustrating the inhibitory effect of HPLC sub-fractions with retention times F19.13 and F19.37. Human leukocytes (U937) were exposed to elevated D-glucose (15 mM) for 24 hours in the presence and absence of the sub-fractions with retention times F19.13 and F19.37 (1:1000 dilution). The data is presented as the mean±s.e.m., n=3, the asterisk representing a significant difference (P<0.05).

The aqueous phase of sub-fraction F13 was purified by HPLC into sub-fractions F18.7-F41.1 coded by their HPLC retention times. The aqueous phase of sub-fraction F13 was directly injected onto the HPLC operating under reversed-phase conditions (Hewlett Packard 1050/\100 series), Separation was achieved with an octadecyl-bonded column with a methanol/water mobile phase, Components eluted from the column were detected by a UV detector operating at a fixed wavelength of 22 nm, These components were revealed as peaks on the chromatographic trace from the mass spectrometer detector. The sub-fractions thus obtained were concentrated in vacuo to dryness, re-dissolved in phosphate buffered saline (PBS) and filter-sterilised. Cell-based assays for core 2 GlcNAc-T activity were carried out and the results suggested the presence of core 2 GlcNAc-T inhibitor in sub-fractions F19-F20.03 (see FIGS. 8 and 9).

Figure 10:
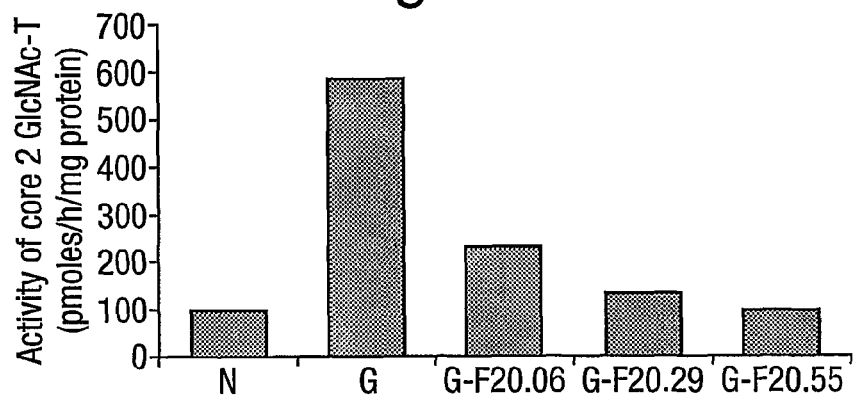
FIG. 10 is a graph illustrating the inhibitory effect on glucose-induced activity of core 2 GlcNAc-T of sub-fractions purified from the aqueous phase of sub-fraction F13 by HPLC with retention times F20.01, F20.29 and F20.55. Human leukocytes (U937) were exposed to elevated D-glucose (15 mM) in the presence and absence of the sub-fractions with retention times F20.01, F20.29 and F20.55 and the activity of core 2 GlcNAc-T was measured after 24 hours. The data is the mean of two separate experiments.
Figure 11:
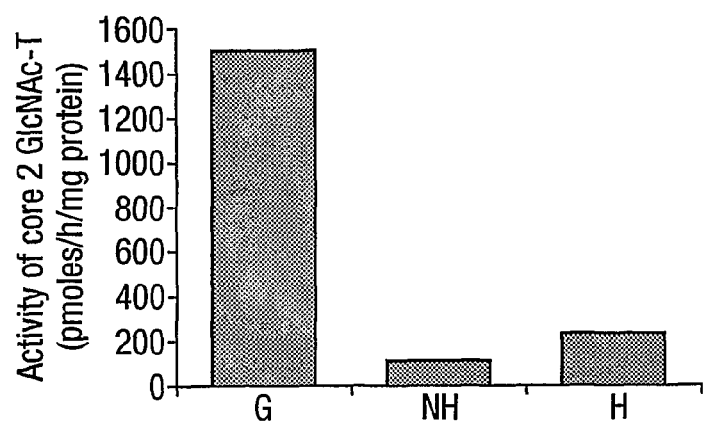
FIG. 11 is a graph illustrating that sub-fraction F20.55 inhibits core 2 GlcNAc-T in a cell-free assay. After exposing human leukocytes (U937) to 15 mM glucose for 24 hours at 37° C., the cells were lysed and then exposed to heated (H, 100° C.) and non-heated (NH) sub-fraction F20.55 (1:500 dilution). After 30 minutes exposure at 37° C., the activity of core 2 GlcNAc-T was measured. The level of core 2 GlcNAc-T activity was measured by determining the formation of core 2 oligosaccharide (attachment of β-1,6-linked GlcNAc to the Gal-1,3-GlcNAc-acceptor). The data is presented as mean±s.e.m. of three separate experiments.
Figure 12A:
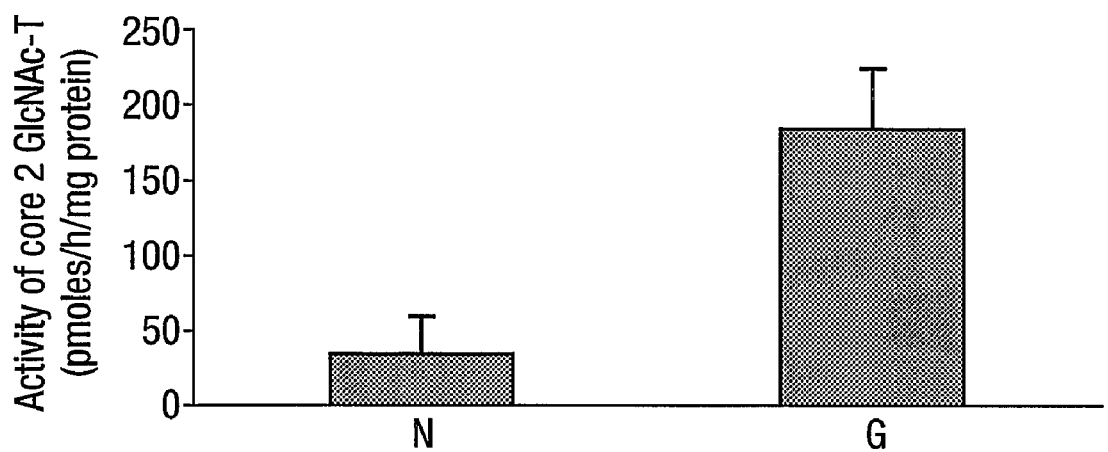
FIGS. 12a and 12b are graphs illustrating that elevated glucose increases core 2 GlcNAc-T activity in cultured bovine retinal vascular cells, namely capillary pericytes (FIG. 13a) and capillary endothelial cells (FIG. 13b). Near confluent cultures were exposed to normal glucose (N, 5.8 mM) and high glucose (G, 15 mM) for 24 hours at 37° C. The cells were lysed and the activity of core GlcNAc-T measured in cell lysates. The data is presented as the mean±s.e.m. (n=3-4), the asterisk representing a significant difference (P<0.05).
Figure 12B:
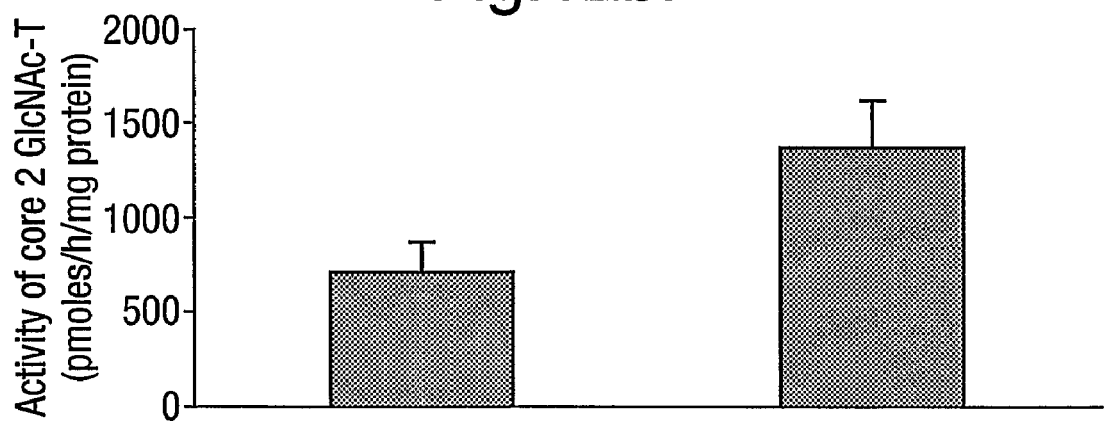

Subsequently larger amounts of the aqueous phase of sub-fraction F13 were purified similarly by HPLC operating under reversed-phase conditions on a phenylbonded column with a methanol/water mobile phase into sub-fractions with retention times of 20.01, 20.29 and 20.55, which are equivalent to sub-fractions F19.13, F19.37 and F19.44 above. Cell based assays for core 2 GlcNAc-T activity confirmed the presence of the core 2 GlcNAc-T inhibitor in these sub-fractions F20.01, F20.29 and F20.55 (FIG. 10a). The inhibition of core 2 GlcNAc-T by HPLC purified sub-fraction F20.55 has been demonstrated using the cell-free assay system (FIG. 11). After exposing human leukocytes (U937) to 15 mM glucose for 24 hours at 37° C., the cells were lysed and then exposed to heated (H, 100° C.) and non-heated (NH) sub-fraction F20.55 (1:500 dilution). After 30 minutes exposure at 37° C., the activity of core 2 GlcNAc-T was measured. As shown in FIG. 11, it was found that sub-fraction F20.55 directly inhibits core 2 GlcNAc-T in a cell-free assay. Heating of sub-fraction F20.55 only slightly altered the level of core 2 GlcNAc-T inhibition.

Structural Analysis of the Core 2 GlcNAc-T Inhibitor.

The core 2 GlcNAc-T inhibitor in the sub-fraction F20.55 has been identified through NMR analysis of a sample dissolved in $CD_3OD$. The following NMR experiments were performed: 1D proton, 2D DQF-COSY ($^1H$-$^1H$ correlation) [8 hours], 2D edited HSQC ($^1H$-$^{13}C$ one-bond correlation with multiplicity editing) [22 hours], 2D TOCSY ($^1H$-$^1H$ relayed correlation) [2×8 hours].

$^1H$ and $^{13}C$ NMR data for the core 2 GlcNAc-T inhibitor in sub-fraction F20.55 is presented in Tables 3 and 4.

TABLE 3

$^1H$ NMR data (sample in deuteriopyridine)

| Sample | Assignment |
|---|---|
| 0.90 singlet | 18-H |
| 1.03 doublet 1 6.7 Hz | 27-H |
| 1.06 singlet | 19-H |
| 1.33 doublet J 7.1 Hz | 21-H |
| 1.77 doublet J 604 Hz | Sugar-Me |
| 2.24 dq J 6.9 Hz | 20-H |
| 5.29 multiplet | 6-H |

TABLE 4

$^{13}C$ NMR data (sample in deuteriopyridine)

| Sample | Assignment |
|---|---|
| Aglycone portion | |
| 37.5 | 1 |
| 30.1 | 2 |
| 78.0 | 3 |
| 38.9 | 4 |
| 140.7 | 5 |
| 121.8 | 6 |
| 32.3 | 7 |
| 31.6 | 8 |
| 50.3 | 9 |
| 37.2 | 10 |
| 21.1 | 11 |
| 39.9 | 12 |
| 40.7 | 13 |
| 56.5 | 14 |
| 32.5 | 15 |
| 81.1 | 16 |
| 63.8 | 17 |
| 16.4 | 18 |
| 19.4 | 19 |
| 40.7 | 20 |
| 16.4 | 21 |
| 10.6 | 22 |
| 110.6 | 23 |
| 37.1 | 24 |
| 28.3 | 25 |
| 34.4 | 26 |

TABLE 4-continued

<sup></sup>13C NMR data (sample in deuteriopyridine)

| Sample | Assignment |
|---|---|
| 75.3 | 27 |
| 17.4 | 28 |
| Sugar portion | |
| 100.2 | Glc 1' |
| 77.7 | 2' |
| 76.3 | 3' |
| 81.9 | 4' |
| 77.7 | 5' |
| 62.1 | 6' |
| 102.0 | Rha 1" |
| 72.5 | 2" |
| 72.7 | 3" |
| 74.1 | 4" |
| 69.5 | 5" |
| 18.6 | 6" |
| 105.1 | Glc 1''' |
| 75.1 | 2''' |
| 78.4 | 3''' |
| 71.6 | 4''' |
| 78.2 | 5''' |
| 61.6 | 6''' |
| 105.1 | Glc 1'''' |
| 75.2 | 2'''' |
| 78.6 | 3'''' |
| 71.6 | 4'''' |
| 78.4 | 5'''' |
| 62.8 | 6'''' |

The compound of interest was identified as Trigoneoside IVa, a known constituent of Fenugreek seeds (55)

Bulk Preparation of Trigoneoside IVa, Protodioscin, Compound 3 and Glycoside F

Crushed seeds (360 g, product of Deep Foods, Inc., Union, N.J. 07083, USA) were extracted successively with heptane (2×700 ml), acetone (4×600 ml) and MeOH (4×600 ml) by boiling under reflux for 2 hrs each. The extracts were filtered and evaporated to dryness under vacuum and analyzed by LC/MS for the presence of furostanol saponins previously reported from this plant (55, 74, 75). The methanol extract (82 g, 22.7% (w/w) of the seeds) was found to contain the target compounds.

The initial extraction of the seeds with heptane and acetone removed most of the less polar materials and improved subsequent chromatography. Further de-fatting can be accomplished by partitioning the methanol extract between butanol and water. However, methanol extract contained relatively little polar material and an enriched saponin containing fraction can be obtained by a solid phase extraction using a styrenic resin such as Diaion HP20 (or SP207, HP20SS, SP207SS, all available from Sigma-Aldrich) resin without subjecting the extract to further de-fatting.

The MeOH extract (CDXA-13-132-1, 81.2 g) was dissolved in water-MeOH (6:4, 400 ml) and loaded onto a Diaion HP20 (Supelco Diaion BP 20, 350 g, 5.0×30 cm) and eluted with water-MeOH (4:6, 600 ml), MeOH (2 L), and acetone (2 L). 250 ml fractions were collected. The fractions were analyzed by HPLC and those with similar compositions were combined to produce 7 pools (CDXA-13-133 F1 to F7). The pool CDXA-13-133-F5 (22.5 g, 27.7% w/w of the extract) was found to contain the majority of the desired saponins.

This pool (22.0 g,) was chromatographed on normal phase silica (445 g, Merck silica gel 60, 70-230 mesh, 0.0763 to 0.200 mm, 5.0×30 cm) and eluted with 3 L each of dichloromethane-MeOH-water systems of following compositions: a) 80:20:3, b) 75:25:3, c) 70:30:3, and d) 65:35:3. 250 ml fractions were collected, analyzed by HPLC and combined into 11 pools (CDXA-13-137-F1 to F11).

The fractions F6 and F7 were combined, dried (10.0 g, 45%) and chromatographed on C8 Silica (350 g, Phenomenex Luna C8(2), 5 micron, 100 A, 5.0×28 cm) and eluted with MeOH-water systems of following compositions: 4:6 (800 ml), b) 5:5 (2 L), c) 55:45 (5 L) 6:4 (1 L), d) 65:35 (1 L), e) 7:3 (1 L), f) 8:2 (1 L) and MeOH (1 L). The fractions were analyzed by HPLC and combined to give 29 pools (CDXA-13-138-F1 to F29). 250 ml fractions were collected.

Fractions F13 to F16 were dried (1.155 g, 11.6%) and purified by reverse phase HPLC using a Gilson semi preparative HPLC system consisting of a UV/Vis detector model 155, pump model 321, and liquid handler model 215.

Chromatographic Conditions:

Column: Phenomenex Luna C18(2), 5 micron, 150×21.2 mm

Mobile Phase Acetonitrile-Water (28:72)

Sample size: 15 mg of each fraction per injection

Detection: UV 205 nm

Five peaks were collected, P1 to P5, (FIG. ** 1 to 5) and were identified by comparison of $^1$H, $^{13}$C NMR and Mass spectral data with those reported in the literature for trigoneoside IVa, its 25 (S) isomer—glycoside F. A further similar compound, compound 3 was detected. This compound has not been previously described.

NMR spectra were recorded in $d_5$ Pyridine. The proton spectra were recorded on a Varian Inova VXRs-300 instrument at 300 MHz and the carbon spectra were recoded on a Varian Inova 400 instrument at 100 MHz.

Mass spectra were recorded on a Finnigan LCQ Deca instrument in APCI mode.

Peak 1, Trigoneoside IVa: White solid (90 mg, 0.025% w/w of the seeds).

$^1$H NMR (pyridine-d5, 400 MHz, δ): 0.90 (3H, s, 18-$H_3$), 1.04 (3H, d, J=6.8 Hz, 27-$H_3$), 1.07 (3H, s, 19-$H_3$), 1.34 (3H, d, J=6.8 Hz, 21-$H_3$), 1.79 (3H, s, J=6.0 Hz, Rha-6"-$H_3$), 3.88 (1H, m, 3-H), 4.09 (2H, m, 16-$H_2$), 4.84 (1H, d, J=7.6 Hz, Glc-1'''-H), 4.97 (1H, overlapped, Glc-1'-H), 5.16 (1H, d, J=7.6 Hz, Glc-1''''-H), 5.29 (1H, d like, 6-H), 6.29 (1H, br s, Rha-1"-H).

Peak 2, Compound C/protodioscin: White solid (120 mg, 0.033%). $^1$H NMR (pyridine-d5, 400 MHz, δ): 0.90 (3H, s, 18-$H_3$), 1.04 (3H, d, J=6.8 Hz, 27-$H_3$), 1.07 (3H, s, 19-$H_3$), 1.34 (3H, d, J=6.8 Hz, 21-$H_3$), 1.66 (3H, s, J=6.0 Hz, Rha-6'''-$H_3$), 1.79 (3H, s, J=6.0 Hz, Rha-6"-$H_3$), 3.88 (1H, m, 3-H), 4.09 (2H, m, 16-$H_2$), 4.84 (1H, d, J=8.0 Hz, Glc-1'''-H), 4.97 (1H, overlapped, Glc-1'-H), 5.90 (1H, br s, Rha-1'''-H), 5.32 1H, d like, 6-H), 6.45 (1H, br s, Rha-1"-H).

Peak 3, Compound 3: White solid (30 mg, 0.008%). $^1$H NMR (pyridine-d5, 400 MHz, δ): 0.89 (3H, s, 18-$H_3$), 1.06 (3H, s, 19-$H_3$), 1.34 (3H, d, J=6.4 Hz, 21-$H_3$), 1.66 (3H, s, J=6.0 Hz, Rha-6'''-$H_3$), 1.79 (3H, s, J=6.0 Hz, Rha-6"-$H_3$), 3.88 (1H, m, 3-H), 4.84 (1H, d, J=8.0 Hz, Glc-1'''-H), 4.97 (1H, overlapped, Glc-1'-H), 5.32 1H, d like, 6-H), 5.90 (1H, br s, Rha-1'''-H), 6.45 (1H, br s, Rha-1"-H).

Peak 4, Glycoside F: White solid (120 mg, 0.033%). $^1$H NMR (pyridine-d5, 400 MHz, δ): 0.90 (3H, s, 18-$H_3$), 1.00 (3H, d, J=6.4 Hz, 27-$H_3$), 1.06 (3H, s, 19-$H_3$), 1.35 (3H, d, J=6.4 Hz, 21-$H_3$), 1.79 (3H, s, J=6.0 Hz, Rha-6-$H_3$), 3.88 (1H, m, 3-H), 3.97 (2H, m, 16-$H_2$), 4.84 (1H, d, J=7.6 Hz, Glc-1''-H), 4.97 (1H, overlapped, Glc-1'-H), 5.16 (1H, d, J=7.6 Hz, Glc-1'''-H), 5.29 (1H, d like, 6-H), 6.29 (1H, br s, Rha-1"-H).

TABLE 5

13C NMR data of Peaks 1 to 5 (in pyridine-d5, 100 MHz)

| Carbon | Peak 1 | Peak 2 | Peak 3 | Peak 4 | Peak 5 |
|---|---|---|---|---|---|
| 1 | 37.5 | 38 | 38 | 38 | 38 |
| 2 | 30.1 | 30.7 | 30.7 | 30.6 | 30.7 |
| 3 | 78.1 | 78.6 | 78.6 | 78.6 | 78.6 |
| 4 | 38.9 | 39.4 | 39.5 | 39.4 | 39.5 |
| 5 | 140.7 | 141.2 | 141.3 | 141.2 | 141.2 |
| 6 | 121.8 | 122.4 | 122.4 | 122.4 | 122.4 |
| 7 | 32.3 | 32.9 | 32.9 | 32.7 | 32.8 |
| 8 | 31.7 | 32.2 | 32.2 | 32.2 | 32.2 |
| 9 | 50.3 | 50.8 | 50.9 | 50.8 | 50.8 |
| 10 | 37.1 | 37.6 | 37.6 | 37.6 | 37.6 |
| 11 | 21.1 | 21.6 | 21.6 | 21.6 | 21.6 |
| 12 | 39.9 | 40.4 | 40.4 | 40.4 | 40.4 |
| 13 | 40.8 | 41.3 | 41.3 | 41.3 | 41.3 |
| 14 | 56.6 | 57.1 | 57.1 | 57.1 | 57.1 |
| 15 | 32.5 | 33 | 33 | 32.8 | 33 |
| 16 | 81.1 | 81.6 | 81.6 | 81.6 | 81.6 |
| 17 | 63.8 | 64.3 | 64.3 | 64.3 | 64.3 |
| 18 | 16.5 | 17 | 17 | 17 | 17 |
| 19 | 19.4 | 19.9 | 20 | 19.9 | 19.9 |
| 20 | 40.7 | 41.2 | 41.2 | 41.2 | 41.2 |
| 21 | 16.5 | 17 | 17 | 17 | 17 |
| 22 | 110.7 | 111.2 | 111.2 | 111.2 | 111.2 |
| 23 | 37.1 | 37.6 | 37.7 | 37.7 | 37.7 |
| 24 | 28.3 | 28.8 | 28.9 | 28.9 | 28.9 |
| 25 | 34.4 | 34.9 | 35 | 34.8 | 34.8 |
| 26 | 75.4 | 75.9 | 75.9 | 75.8 | 75.8 |
| 27 | 17.4 | 18 | 18 | 18 | 18 |
| G1' | 100 | 100.5 | 100.8 | 100.5 | 100.8 |
| G2' | 77.3 | 77.8 | 78.5 | 77.7 | 78.4 |
| G3' | 76.2 | 76.7 | 78.3 | 76.6 | 78.2 |
| G4' | 81.9 | 82.5 | 78.8 | 82.5 | 78.9 |
| G5' | 77.7 | 78.2 | 77.4 | 78.2 | 77.4 |
| G6' | 62.1 | 62.5 | 61.8 | 62.5 | 61.7 |
| rha1'' | 101.8 | 102.3 | 102.6 | 102.3 | 102.5 |
| rha2'' | 72.4 | 73 | 73.1 | 73 | 73 |
| rha3'' | 72.7 | 73.3 | 73.3 | 73.3 | 73.3 |
| rha4'' | 74.1 | 74.6 | 74.6 | 74.6 | 74.6 |
| rha5'' | 69.5 | 70 | 70.1 | 70 | 70 |
| rha6'' | 18.7 | 19.2 | 19.2 | 19.2 | 19.2 |
| glc1/rha1''' | 105.2 | 105.7 | 103.4 | 105.7 | 103.4 |
| glc2/rha2''' | 75 | 75.5 | 73.1 | 75.5 | 73 |
| glc3/rha3''' | 78.4 | 79 | 73.2 | 79 | 73.2 |
| glc4/rha4''' | 71.2 | 71.7 | 74.4 | 71.7 | 74.4 |
| glc5/rha5''' | 78.2 | 78.7 | 70.9 | 78.8 | 70.9 |
| glc6/rha6''' | 61.8 | 62.3 | 19 | 62.3 | 19 |
| 26-O-G1'''' | 105.1 | 105.7 | 105.7 | 105.4 | 105.4 |
| G2'''' | 75.2 | 75.7 | 75.7 | 75.7 | 75.7 |
| G3'''' | 78.6 | 79.1 | 79 | 79.1 | 79.1 |
| G4'''' | 71.6 | 72.1 | 72.1 | 72.1 | 72.1 |
| G5'''' | 78.4 | 79 | 79 | 79 | 79 |
| G6'''' | 62.8 | 63.3 | 63.3 | 63.3 | 63.3 |

TABLE 6

Summary

| Compound ID | Name | Yield (mg) |
|---|---|---|
| F1 | Trigoneoside IVa | 90 mg |
| F2 | Compound C/Protodioscin | 120 mg |
| F3 | Compound 3 | 30 mg |
| F4 | Glycoside F | 120 mg |
| F5 | Trigonelloside C | 300 mg |

Chemical structures for the five compounds are given in FIG. 15.

Other Compounds

Figure 15A:
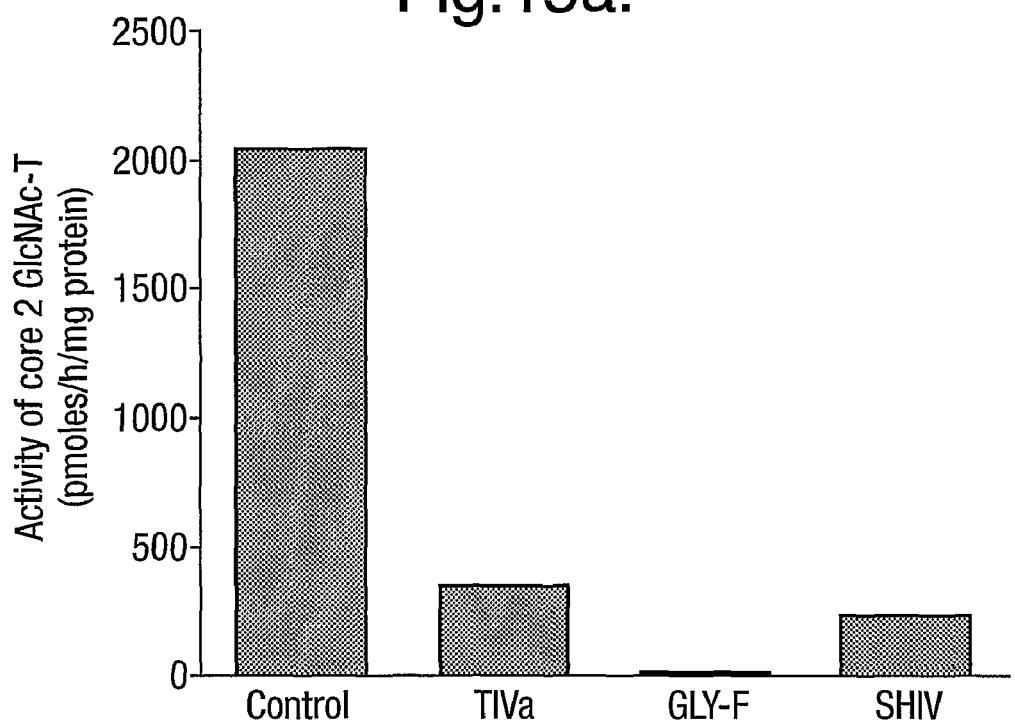
FIG. 15a and FIG. 15b are graphs illustrating the effect of purified trigoneoside IVa, glycoside F, and shatavarin IV on Core 2 GlcNAc-T activity in cell free (FIG. 15a) and cell based (FIG. 15b) assays.

Shatavarin IV (FIG. 15) isolated from *Asparagus racemosus* (56) and protodioscin from *Tribulus terrestris* (but also isolatable from fenugreek as compound C of (55)) were both supplied by Chromadex inc. 2952 S. Daimler St. Santa Ana Calif. Protodioscin was also isolated from the above preparation of fenugreek as peak 2 conforming to published NMR spectra of protodioscin Biological Activity of Trigoneoside IVa, Glycoside F, Protodioscin and Shatavarin IV Cell-Free Assay Heart lysate from BB rats were incubated in the presence, and absence of 20 ng/ml of each compound. After 1 h incubation at 37° C., the activity of core 2 GlcNAc-T was measured, and expressed as pmoles/h/mg protein. The results are the mean of 3-5 separate experiments. The results are shown in FIG. 15a Trigoneoside IVa, its 25(R) isomer glycoside F and shatavarin IV are highly active inhibitors of Core 2 GlcNAc-T in cell free assays, whilst protodioscin, in which the glucose at the 4 position is replaced by rhamnose, is not active.

Cell Based Assay

Figure 15B:
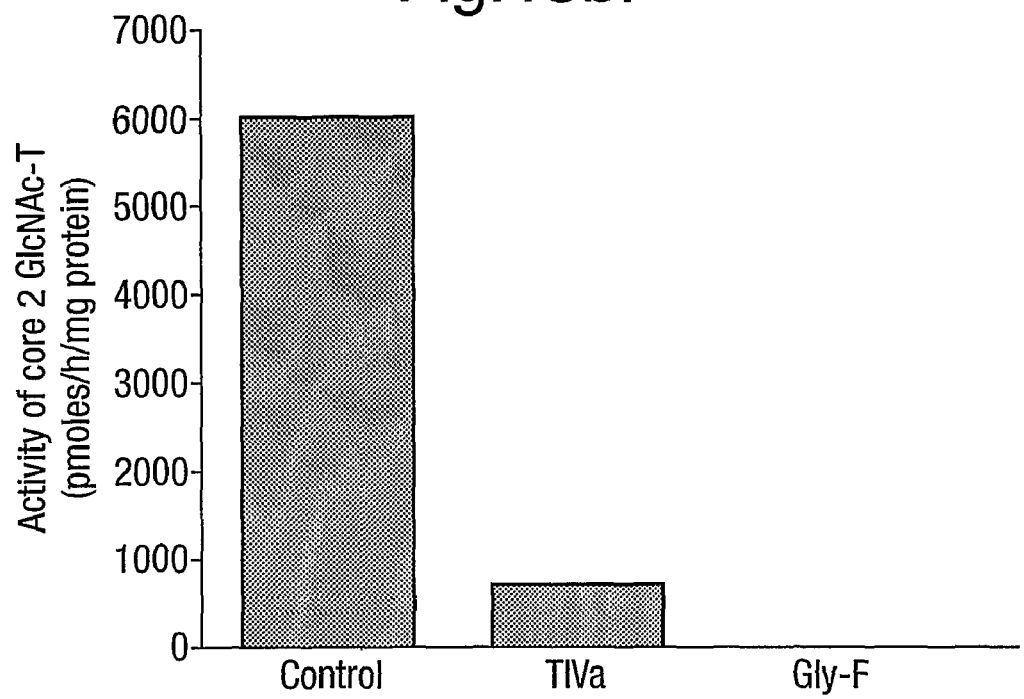

Human leukocytes (U937 cells) were exposed to 8 pg/ml human recombinant TNF-alpha in the presence and absence of 20 ng/ml of the test compound. After 24 h incubation, the activity of core 2 GlcNAc-T was measured, and expressed as pmoles/h/mg protein. The results are shown in FIG. 15b.

Trigoneoside IVa, and glycoside F are highly active inhibitors of Core 2 GlcNAc-T in cell free assays, whilst protodioscin is not active.

The Core 2 GlcNAc-T Inhibitor Trigoneoside IVa and Diabetic Retinopathy

Figure 13A:
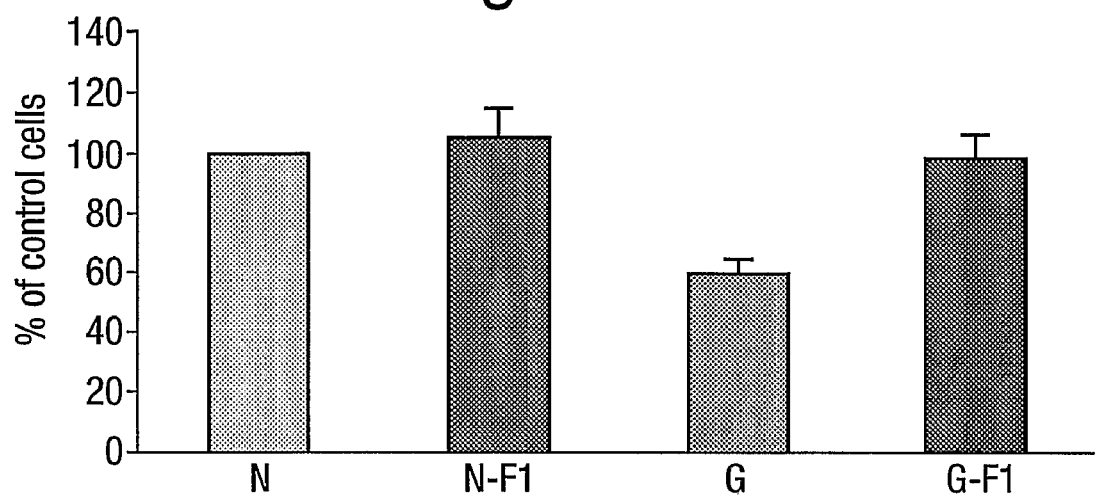
FIGS. 13a and 13b are graphs illustrating that a crude extract F1 of fenugreek seeds prevents glucose-induced toxicity in cultured bovine retinal vascular cells, namely capillary pericytes (FIG. 14a) and capillary endothelial cells (FIG. 14b). Cells were exposed to normal (N, 5.8 mM) and high glucose (G, 25 mM) in the presence (N-F, G-F) and absence (N, G) of the fenugreek seed extract. After 4 days incubation, the number of viable cells was determined using a haemocytometer and trypan blue exclusion. The data is presented as the mean±s.e.m., n=18 separate experiments, the asterisk representing a significant difference (P<0.05).
Figure 13B:
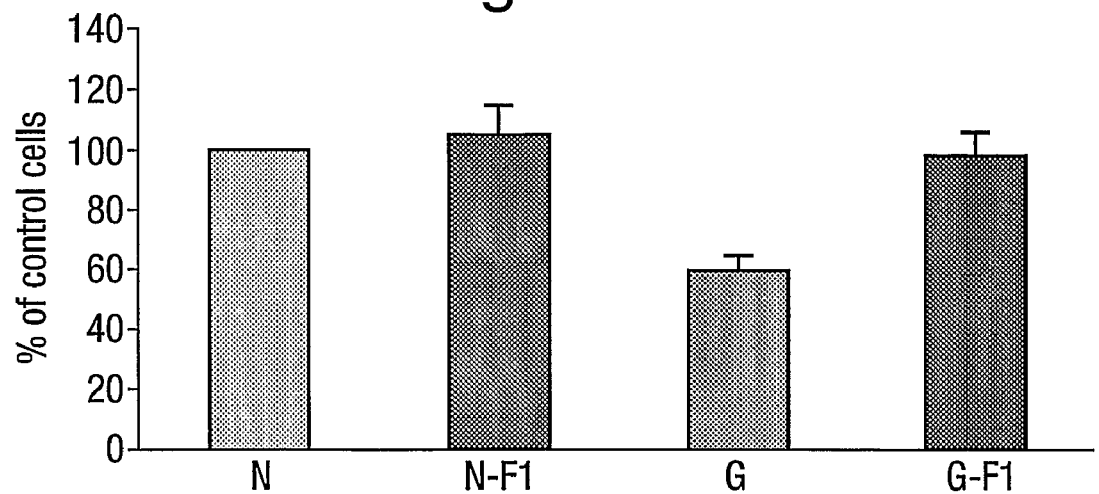

It has been found that elevated glucose levels significantly increase the activity of core 2 GlcNAc-T in cultured bovine retinal vascular cells, namely capillary pericytes (BRP) and capillary endothelial cells (BREC) (FIG. 13). Near confluent cultures were exposed to normal glucose (N, 5.8 mM) and high glucose (G, 15 mM) for 24 hours at 37° C. The cells were lysed and the activity of core GlcNAc-T measured in cell lysates.

Figure 14I:
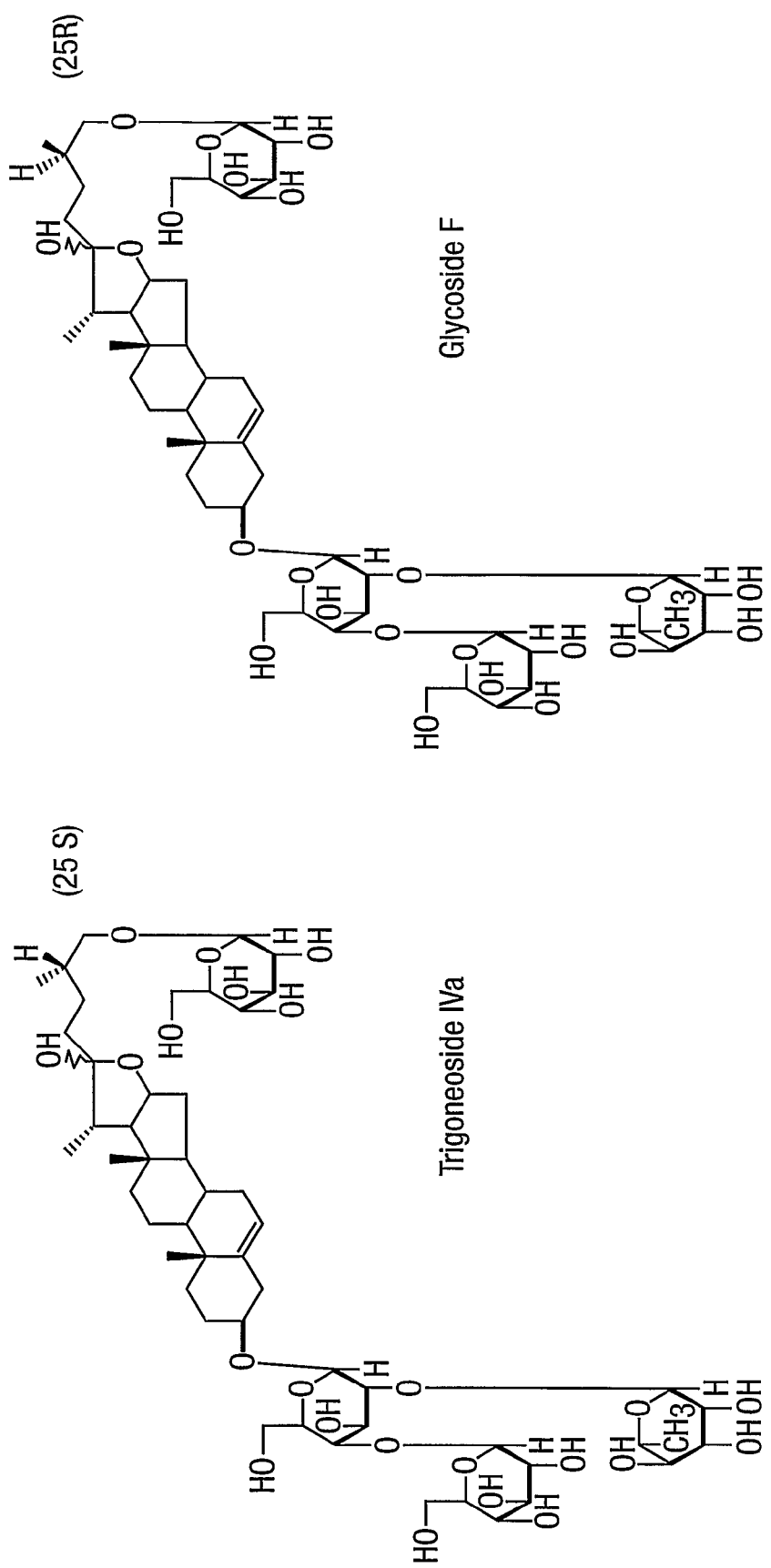
FIG. 14 illustrates the structures of the five compounds isolated from fenugreek seeds.
Figure 14:
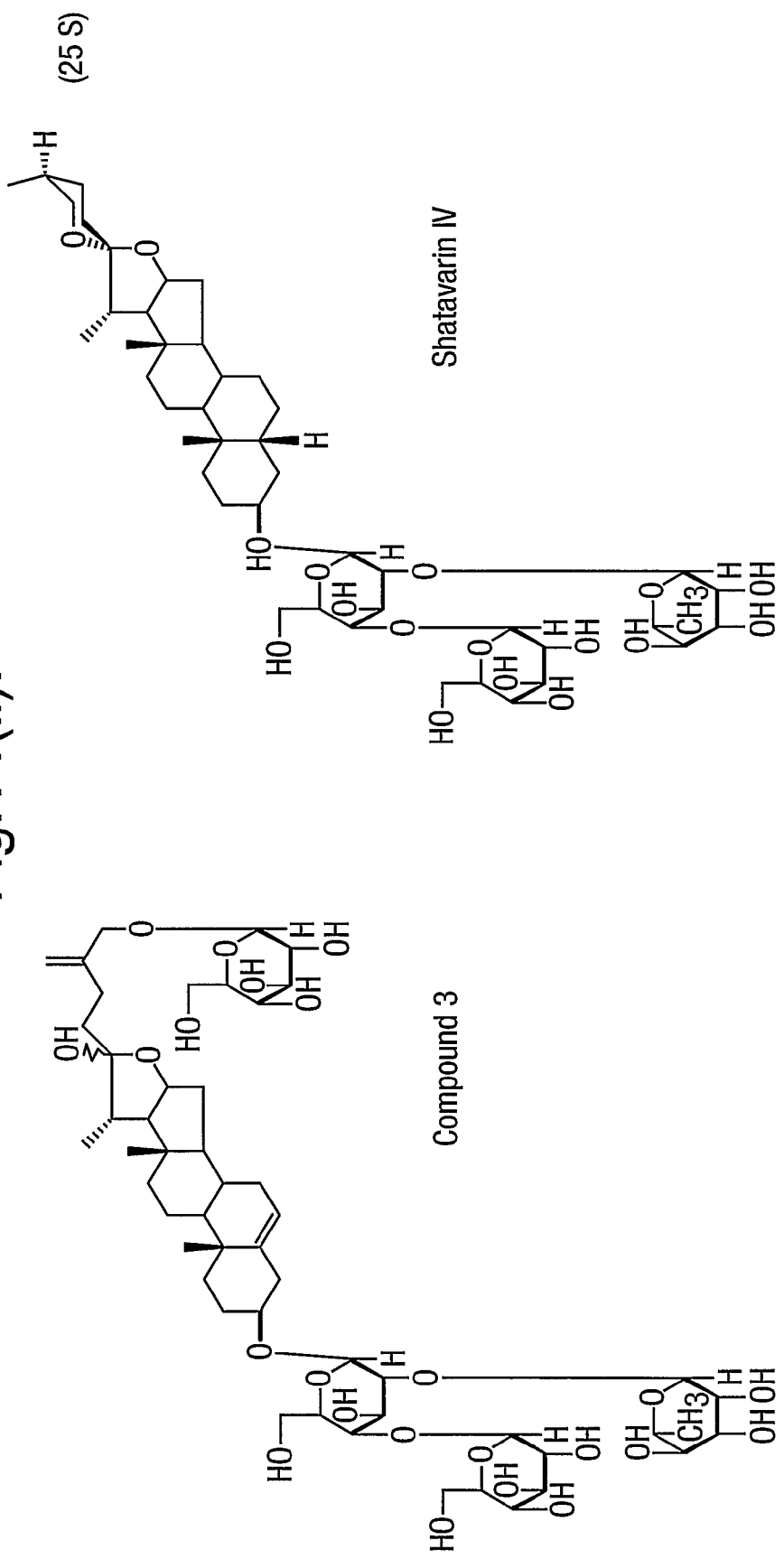

It has further been demonstrated that fenugreek seed extract has the potential to reverse glucose-induced toxicity (FIG. 14) in cultured bovine retinal capillary pericytes (BRP) and endothelial cells (BREC). Cells were exposed to normal (N, 5.8 mM) and high 15 glucose (G, 25 mM) in the presence (N-F, G-F) and absence (N, G) of the fenugreek seed extract. After 4 days incubation, the number of viable cells was determined using a haemocytometer and trypan blue exclusion. It was found that fenugreek seed extract indeed reverses glucose-induced toxicity in cultured bovine retinal capillary pericytes and endothelial cells. However, it is not established yet whether fenugreek seed extract reverses glucose-induced toxicity by normalising the activity of core 2 GlcNAc-T.

This protection of retinal vascular cells fenugreek seed extract is significant, because damage to retinal vascular cells is a hallmark of early diabetic retinopathy. Diabetic retinopathy in humans is mainly a vascular disease, primarily affecting the capillaries. The first ultrastructural and microscopic changes reported are retinal capillary basement membrane thickening and pericyte degeneration, both of which compromise the integrity of the capillary wall. Pericyte degeneration leaves lightly stained compartments in the basement membrane sheath called pericyte "ghosts". Damage to both pericytes and endothelial cells leads to the formation of acellular capillaries.

Treatment

Medicaments comprising the compounds of the formula I described herein can be administered by oral or parenteral routes, including intravenous, intramuscular, intraperitoneal, subcutaneous, transdermal, airway (aerosol), rectal, vaginal and topical (including buccal and sublingual) administration. For oral administration, the compounds of the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatine, while the lubricating agent, if present, may be magnesium stearate, stearic acid or talc. If desired, the tablets may be coated with a material, such as glyceryl mono stearate or glyceryl distearate, to delay absorption in the gastrointestinal tract. Capsules for oral use include hard gelatine capsules in which the active ingredient is mixed with a solid diluent, and soft gelatine capsules wherein the active ingredients is mixed with water or an oil such as peanut oil, liquid paraffin or olive oil Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The fenugreek seed extracts and core 2 GlcNAc-T inhibitors of the present invention may also be presented as liposome formulations.

In general a suitable dose will be in the range of 0.01 to 10 mg per kilogram body weight of the recipient per day of the core 2 GlcNAc-T inhibitor, preferably in the range of 0.2 to 1.0 mg per kilogram body weight per day. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

REFERENCES

1. Colley K. J., "Golgi localization of glycosyltransferases: more question than answers", *Glycobiology* 7, 1-13 (1997)
2. Varki A., "Biological roles of oligosaccharides: all of the theories are correct", *Glycobiology* 3, 97-130 (1993)
3. Williams D. et al. "Mucin synthesis. Detection in canine submaxillary glands of an N-acteylglucosaminyltransferase which acts on mucin substrates", *J. Biol. Chem.* 255, 11247-11252 (1980)
4. Schachter H. et al., "Composition, Structure and Function" in *Glyconjugates*, eds. Allen H. J. and Kisailus E. C., pages 263-332, Marcel Dekker, New York (1992)
5. Leferte S. et al., "Glycosylation-dependent collagen-binding activities of two membrane glycoproteins in MDAY-D2 tumour cells", *Cancer Res.* 48, 4743-4748 (1988)
6. Ellies L. G. et al., "Core 2 oligosaccharide biosynthesis distinguishes between selectin ligands essential for leukocyte homing and inflammation", *Immunity* 9, 881-890 (1998)
7. Brockhausen I. et al., "Biosynthesis of O-glycans in leukocytes from normal donors and from patients with leukemia: increase in O-glycan core 2 UDPGlcNAc:Gal[β]3GalNAc[α]-R(GlcNAc to GalNAc)[p](1,6)-N-acetylglucosaminy ltransferase in leukemic cells", *Cancer Res.* 51, 1257-1263 (1991)
8. Renkonen J. et al., "Core 2 beta-1,6-N-acetylglucosaminyltransferases and alpha-1,3-fucosyltransferases regulate the synthesis of O-glycans on selectin ligands on oral cavity carcinoma cells", *APMIS* 109, 500-506 (2001)
9. Machida E. et al., "Clinicopathological significance of core 2 beta-1,6-N-acetylglucosaminyltransferase messenger RNA expressed in the pulmonary adenocarcinoma determined by in situ hybridisation", *Cancer Res.* 61, 2226-2231 (2001)
10. Dalziel M. et al., "The relative activities of the C2GnT1 and ST3Gal-I glycosyltransferases determine O-glycan structure and expression of a tumor-associated epitope on MUC1", *Biol. Chem.* 276, 11007-11105 (2001)
11. Perandio M. et al., "Severe impairment of leukocyte rolling in venules of core 2 glucosaminyltransferase-deficient mice", *Blood* 97, 3812-3819 (2001)
12. Yousefi S. et al., "Increased UDP-GlcNAc:Gal[beta]1-3GalNAcR(GlcNAc to GalNAc) [beta]-1,6-acetylglucosaminyltransferase activity in metastic murine tumour cell lines", *J. Biol. Chem.* 266, 1772-1782 (1991)
13. Higgins E. A. et al., "Aberrant O-linked oligosaccharide biosynthesis and platelets from patients with the Wiskott-Aldrich syndrome", *J. Biol. Chem.* 266, 6280-6290 (1991)
14. Piller F. et al., "Human T-lymphocyte activation is associated with changes in O-glycans biosynthesis", *J. Biol. Chem.* 263, 15146-15150 (1988)
15. Koya D. et al., "Overexpression of core 2 N-acetylglycosaminyltransferase enhances cytokine actions and induces hyperetropic myocardium in transgenic mice", *FASEB J.* 13, 2329-2337 (1999)
16. Nishio Y. et al., "Identification and characterization of a gene regulating enzymatic glycosylation which is induced by diabetes and hyperglycemia specifically in rat cardiac tissue", *J. Clin. Invest.* 96, 1759-1767 (1995)
17. Tsuboi S. et al., "Roles of O-linked oligosaccharides in immune responses", *Bioassays* 23, 46-53 (2001)
18. Tsuboi S. et al., "Branched o-linked oligosaccharides ectopically expressed in transgenic mice reduce primary T-cell immune responses", *EMBO J.* 16, 6364-6373 (1997)
19. Tsuboi S. et al., "Roles of O-linked oligosaccharides in immune responses", *Bioassays* 23, 46-53 (2001)
20. Piller F. et al., "Human T-lymphocyte activation is associated with changes in O-glycans biosynthesis", *J. Biol. Chem.* 263, 15146-15150 (1988)
21. Tsuboi S. et al., "Overexpression of branched O-linked oligosaccharides on T cell surface glycoproteins impairs humoral immune responses in transgenic mice", *J. Biol. Chem.* 273(46), 30680-30687 (1998)
22. Maemura K. et al., "Poly-N-acetyllactosaminyl O-glycans attached to Leukosialin. The presence of sialyl Le(x) structures in O-glyeans", *J. Biol. Chem.* 267(34), 24379-24386 (1992)
23. Nakamura M. et al., "Simultaneous core 2 beta1→6N-acteylglucosaminyltransferase up-regulation and sialyl-Le (X) expression during activation of human tonsillar B lymphocytes", *FEBS Lett.* 463(1-2), 125-128 (1999)
24. Wilkins P. P. et al., "Structures of the O-glycans on P-selectin glycoprotein ligand-1 from HL-60 cells", *J. Biol. Chem.* 271(31), 18732-18742 (1996)
25. Ohmori K. et al., "A distinct type of sialyl Lewis X antigen defined by a novel monoclonal antibody is selectively expressed on helper memory T cells", *Blood* 82(9), 2797-805 (1993)
26. Kumamoto K. et al., "Specific detection of sialyl Lewis X determinant carried on the mucin GlcNAcbeta1→6GalNAcalpha core structure as a tumor-associated antigen", *Biochem. Biophys. Res. Commun.* 247 (2), 514-517 (1998)
27. Varki A. "Biological roles of oligosaccharides: all of the theories are correct", *Glycobiology* 3, 97-130 (1993)
28. Walz G. et al., "Recognition by ELAM-1 of the sialyl-Lex determinant on myeloid and tumor cells", *Science* 250 (4984), 1132-1135 (1990)
29. Majuri M. L et al., "Recombinant E-selectin-protein mediates tumor cell adhesion via sialyl-Le(a) and sialyl-Le(x)", *Biochem. Biophys. Res. Commun.* 182(3), 1376-82 (1992)
30. Takada A. et al., "Contribution of carbohydrate antigens sialyl Lewis A and sialyl Lewis X to adhesion of human cancer cells to vascular endothelium", *Cancer Res.* 53(2), 354-361 (1991)
31. Yousefi S. et al., "Acetylglucosaminyltransferase activity in metastic murine tumour cell lines", *J. Biol. Chem.* 266, 1772-1782 (1991)
32. Beaum P. V. et al., "Expression of core 2 beta-1,6-N-acetylglucosaminytransferase in a human pancreatic cancer cell line results in altered expression of MUC1 tumour-associated epitopes", *J. Biol. Chem.* 274, 24641-24648 (1999)
33. Saitoh O. et al., "Expression of aberrant O-glycans attached to leukosialin in differentiation-deficient HL-60 cells", *Cancer Res.* 51(11), 2854-2862 (1991)
34. Brockhausen I. et al., "Biosynthesis of O-glycans in leukocytes from normal donors and from patients with leukemia: increase in O-glycan core 2 UDPGlcNAc:Gal[beta]3GalNAc[alpha]-R(GlcNAc to GalNAc)[beta](1,6)-N-acetylglucosaminyltransferase in leukemic cells", *Cancer Res.* 51, 1257-1263 (1991)
35. Renkonen J. et al., "Core 2 beta1,6-N-acetylglucosaminyltransferases and alpha-1,3-fucosyltransferases regulate the synthesis of O-glycans on selectin ligands on oral cavity carcinoma cells", *APMIS* 109, 500-506 (2001)
36. Shimodaira K. et al., "Carcinoma-associated expression of core 2 beta-1,6-N-acetylglucosaminyltransferase gene in human colorectal cancer: role of O glycansin tumor progression", *Cancer Res.* 1; 57(23), 5201-5216 (1997)
37. Numahata K. et al., "A distinct type of sialyl Lewis X antigen defined by a novel monoclonal antibody is selectively expressed on helper memory T cells", *Blood* 82(9), 2797-805 (2002)
38. Klein R., et al., "The Winconsin epidemiology study of diabetic retinopathy X. Four-year incidence and progression of diabetic retinopathy when age at diagnosis is 30 or more years", *Arch. Opthalmol.* 107, 244-250 (1989)
39. Davis M. D., "Diabetic retinopathy—a clinical overview", *Diabetes Care* 15, 1844-1873 (1993)
40. Kohner E. M. et al., "Diabetic retinopathy" in *Diabetic Angiopathy*, ed. Tooke J. E., pages 233-247, Oxford University Press (1999)
41. Chibber R. et al., "Activity of core 2 GlcNAc-(beta 1,6) transferase, is higher in polymorphonuclear leukocytes from diabetic patients compared to age-matched control subjects", *Diabetes* 49, 1724-1730 (2000)
42. Koya D. et al., "Protein kinase C activation and the development of diabetic complications", *Diabetes* 47, 859-866 (1998)
43. Meier M. et al., "Protein kinase C activation and its pharmacological inhibition in vascular disease", *Vasc. Med.* 5, 173-185 (2000)
44. Sharma R. D. et al., "Effect of fenugreek seeds on blood glucose and serum lipids in type I diabetes", *Eur. J. Clin. Nutr.* 44, 301-306 (1990)
45. Broca C. et al., "4-Hydroxyisoleucine: effects of synthetic and natural analogues on insulin secretion", *Eur. J. Pharmacol.* 390(3), 339-345 (2000)
46. Sauvaire Y. et al., "4-Hydroxyisoleucine: a novel amino acid potentiator of insulin secretion", *Diabetes* 47(2), 206-210 (1998)
47. Kuhns W. et al., (1993) Processing O-glycan core 1, Galβ1-3GalNAcα-R. Specificities of core 2 UDP-GlcNAc: Galβ1-3 GalNAc-R (GlcNAc to GlcNAc)β6-N-acetylaminotransferase and CMP sialic acid:Galβ1-3GalNAcRα3sialyltransferase. *Glycoconjugate Journal* 10 381-394
48. Paulsen H. et al., Leibigs Ann. Chem. 747-758. (1992)
49. Mulvihill N. T. et al., Inflammation in acute coronary syndromes. Heart. 87(3):201-4. (2002).
50. Guray U. et al., Poor coronary collateral circulation is associated with higher concentrations of soluble adhesion molecules in patients with single-vessel disease. Coron Artery Dis. 15(7):413-7 (2004)
51. Guray U. et al., Levels of soluble adhesion molecules in various clinical presentations of coronary atherosclerosis. Int J Cardiol. 2004 96(2):235-40.
52. O'Brien K D et al., Neovascular expression of E-selectin, intercellular adhesion molecule-1, and vascular cell adhesion molecule-1 in human athero-sclerosis and their relation to intimal leukocyte content. Circulation. 15; 93(4): 672-82. (1996).
53. Davies M J et al., The expression of the adhesion molecules ICAM-1, VCAM-1, PECAM, and E-selectin in human atherosclerosis. J Pathol. 171(3):223-9 (1993).
54. Chibber R et al., Activity of the glycosylating enzyme, core 2 GlcNAc (β, 1,6) transferase, is higher in polymorphonuclear leukocytes from diabetic patients compared with age-matched control subjects: relevance to capillary occlusion in diabetic retinopathy. Diabetes; 49(10):1724-30 (2000).
55. Yoshikawa M. et al., Medicinal Foodstuffs. VIII. Fenugreek seed. (2): Structures of six new furostanol saponins, trigoneosides Iva, Va, Vb, VI, VIIb, and VIIIb from the seeds of indian *Trigonella foenum-graecum* L. Heterocycles 47, 397-405 (1998).
56. Ravikumar P. R. et al., Dev. Chemistry of Ayurvedic crude drugs part VI—(Shatavari-1): Structure of shatavarin-IV. Indian J. Chem. 26B, 1012-1017 (1987).
57. Shimomura H. et al., Steroidal saponins, Pardarinoside A-G from the bulbs of *Lilium pardarinum*. Phytochemistry 28, 3163-3170 (1989).
58. Minaki Y et al., Steroidal saponins and alkaloids from the bulbs of *Lilium brownii* var. *colchesteri*. Chemical & Pharmaceutical Bulletin 38(11), 3055-9 (1990).
59. Sashida Y et al., Studies on the chemical constituents of the bulbs of *Lilium mackliniae*. Chemical & Pharmaceutical Bulletin 39(9), 2362-8 (1991)
60. Akhov L. S. et al., Structure of steroidal saponins from underground parts of *Allium nutans* L. Journal of Agricultural and Food Chemistry 47(8), 3193-3196 (1999)

61. Joshi J. et al., Chemistry of Ayurvedic crude drugs part VIII—Shatavari-2: Structure elucidation of bioactive shatavarin I and other glycosides. Indian J. Chem. 27B, 12-16 (1988).
62. Vasil'eva I. S. et al., Composition and biologiucal activity of steroid glycosides from cell suspensions of dioscorea deltoidea wall. Appl. Biochem. Microbiol. 31, 206-209 (1995).
63. Sharma et al., Oligofurostanosides from *Asparagus curillus* leaves. Phytochemistry. 33(3):683-6. (1993).
64. Petit G. et al., Isolation and structure of cytostatic steroidal saponins from the African medicinal plant *Balanites aegyptica*. Journal of natural products 54, 1491-1502.
65. Hostettman K. Saponins. Cambridge University Press UK. (1995).
66. Li C et al, Synthesis of diosgenyl alpha-L-rhamnopyranosyl-(1-->2)-[beta-D-glucopyranosyl-(1-->3)]-beta-D-glucopyranoside (gracillin) and related saponins. Carbohydr Res.; 306(1-2):189-95. (1998).
67. Deng S et al., Synthesis of three diosgenyl saponins: dioscin, polyphyllin D, and balanitin 7. Carbohydr Res.; 30; 317(1-4):53-62. (1999)
68. Li B et al, An improved synthesis of the saponin, polyphyllin D. Carbohydr Res.; 9; 331(1):1-7. (2001).
69. Yu B et al., A "double random" strategy for the preparation of saponin libraries. J Comb Chem.; 3(5):404-6. (2001).
70. Yu B., et al., The first synthetic route to furostan saponins. Tetrahedron letters, 42, 77-79 (2001).
71. Yu B et al., Glycosyl trifluoroacetimidates. 2. Synthesis of dioscin and xiebai saponin I. J Org. Chem.; 13; 67(25): 9099-102 (2002).
72. Cheng M S et al., Total synthesis of methyl protodioscin: a potent agent with antitumor activity. J Org. Chem.; 2; 68(9):3658-62 (2003)
73 Du Y et al., Synthesis of saponins using partially protected glycosyl donors. Org. Lett.; 2; 5(20):3627-30. (2003).
74. Yoshikawa et al., Medicinal foodstuffs. IV. Fenugreek seed. (1): structures of trigoneosides Ia, Ib, IIa, IIb, IIIa, and IIIb, new furostanol saponins from the seeds of Indian *Trigonella foenum-graecum* L. Chem Pharm Bull (Tokyo); 45(1):81-7 (1997).
75. Murakami T et al., Medicinal foodstuffs. XVII. Fenugreek seed. (3): structures of new furostanol-type steroid sap onins, trigoneo sides Xa, Xb, XIb, XIIa, XIIb, and XIIIa, from the seeds of Egyptian *Trigonellafoenumgraecum* L. Chem Pharm Bull (Tokyo); 48(7):994-1000 (2000).

The invention claimed is:
1. A method of treatment of a condition associated with raised activity of the enzyme Core 2 GlcNAc-T comprising administration of an effective amount of a compound of the formula IV to a patient in need thereof:

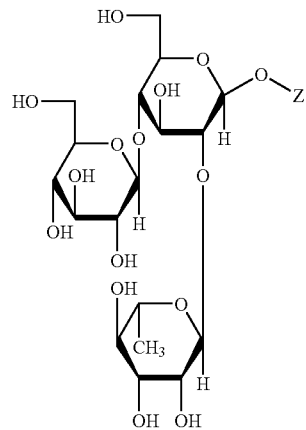

wherein
Z is either a group of the formula VII:

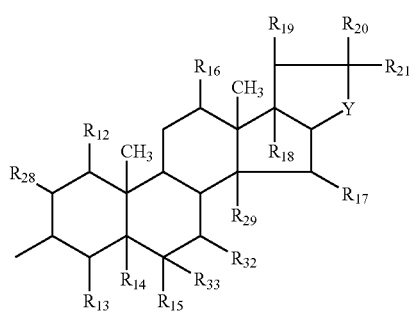

wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$ is H or —OH;
$R_{18}$ is H or —OH;
$R_{19}$ is H, or —CH$_3$;
$R_{20}$ is —OH or $C_{1-6}$ alkoxy;
$R_{21}$ is of the formula VIII;

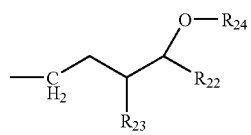

$R_{22}$ is H, —OH, or —OMe;
$R_{23}$ is CH$_2$H$_4$OH, —CH$_2$OH, —CH$_3$ or =CH$_2$;
$R_{24}$ is $C_{1-6}$ alkyl, $C_{1-6}$ acyl, or glucose;
$R_{29}$ is H or —OH;
$R_{32}$ is H or —OH;
$R_{33}$ is H; and
Y is O;
or a group of the formula XI:

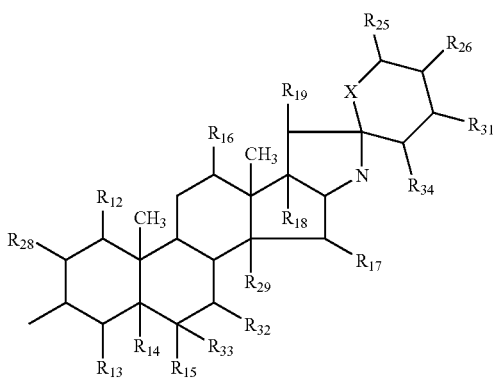

wherein:

$R_{12}$, $R_{13}$, $R_{15}$ and $R_{28}$ each represent H;

$R_{14}$ is H, or $R_{14}$ and $R_{33}$ taken together represent the second bond of a double bond joining adjacent carbon atoms;

$R_{16}$ is H, or =O;

$R_{17}$, $R_{18}$, $R_{25}$, $R_{29}$, $R_{31}$, $R_{32}$, and $R_{34}$ are independently selected from H and —OH;

$R_{19}$ is H, or —CH$_3$;

$R_{26}$ is —CH$_2$H$_4$OH, —CH$_2$OH, —CH$_3$ or =CH$_2$;

$R_{33}$ is H; and

X is O or NH;

or a pharmaceutically acceptable salt, ester or tautomeric form thereof; and wherein said condition associated with raised activity of the enzyme Core 2 GlcNAc-T is selected from the group consisting of an inflammatory disease, diabetic cardiomyopathy, myocardial dysfunction, cancer, cancer metastasis and diabetic retinopathy.

2. A method according to claim 1 in which the group of the formula (VII) is selected from the group consisting of:

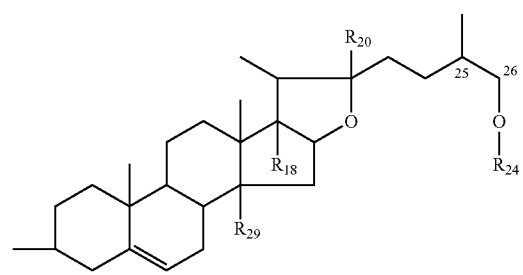

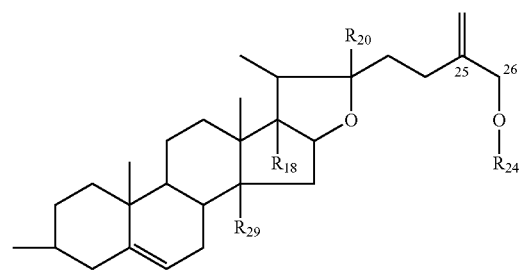

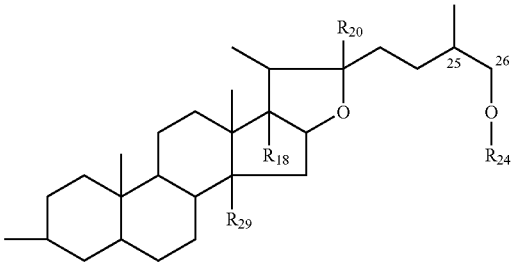

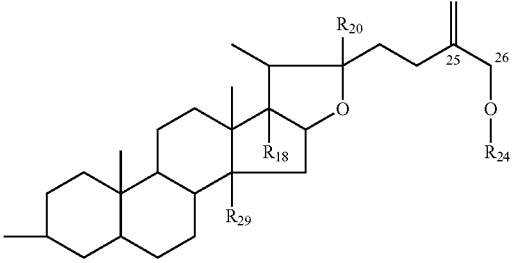

wherein:

$R_{18}$ is H or —OH;

$R_{20}$ is —OH or C$_{1-6}$alkoxy;

$R_{24}$ is glucose or C$_{1-6}$ acyl; and $R_{29}$ is H or —OH.

3. A method according to claim 1 in which the compound of the formula IV is selected from the group consisting of:

trigoneoside IVa which is (3β,25S)-26-(β-D-glucopyranosyloxy)-22-hydroxyfurost-5-en-3-yl-O-α-L-rhamnopyranosyl-(1→2)-O-[β-D-glucopyranosyl-(1→4)]-β-D-glucopyranoside, glycoside F which is (β3)-26-(β3-D-glucopyranosyloxy)-22-hydroxyfurost-5-en-3-yl-O-α-L-rhamnopyranosyl-(1→2)-O-[β3-D-glucopyranosyl-(1→4)]-β-D-glucopyranoside, shatavarin I, compound 3, pardarinoside C.

4. A method according to claim 1 in which the group of the formula XI is selected from the group consisting of:

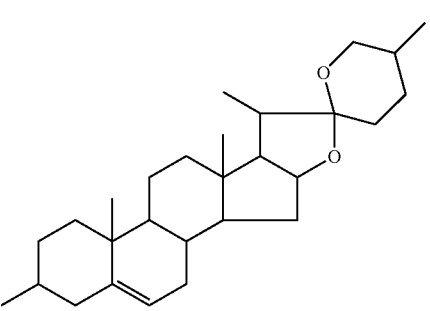

-continued

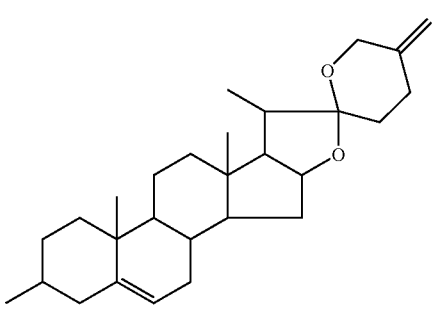
B

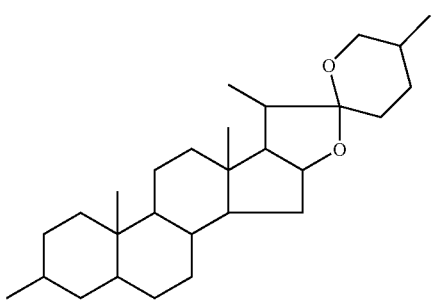
C

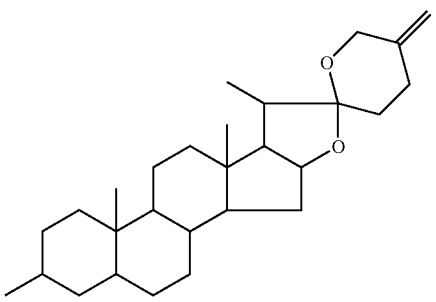
D

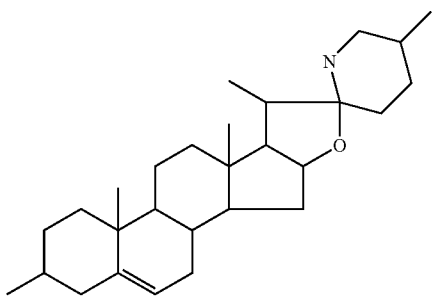
E

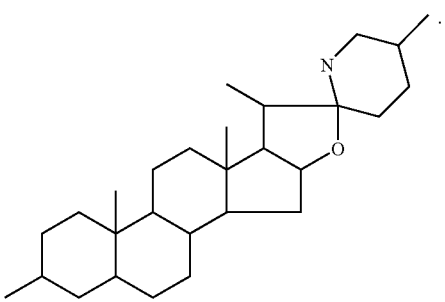
F

5. A method according to claim 1 in which the group of the formula XI is selected from the group consisting of diosgenin, yamogenin, tigogenin, neotigogenin, sarsasapogenin, smilagenin, hecogenin, solasodine or tomatidine.

6. A method of claim 1 in which the compound of the formula IV are selected from the group consisting of:

Shatavarin IV which is sarsasapogenin 3-O-α-L-rhamnopyranosyl-(1→2)-O-[β-D-glucopyranosyl-(1→4)]-β-D-glucopyranoside, Compound 12 which is solasodine 3-O-α-L-rhamnopyranosyl-(1→2)-O-[β-D-glucopyranosyl-(1→4)]-β-D-glucopyranoside, Deltonin which is (3β,25R)-spirost-5-en-3-yl-O-α-L-rhamnopyranosyl-(1→2)-O-[β-D-glucopyranosyl-(1→4)]-β-D-Glucopyranoside, and Balanitin VI is (3β,25S)-spirost-5-en-3-yl-O-α-L-rhamnopyranosyl-(1→2)-O-[β-D-glucopyranosyl-(1→4)]-β-D-Glucopyranoside.

7. A compound of the formula:

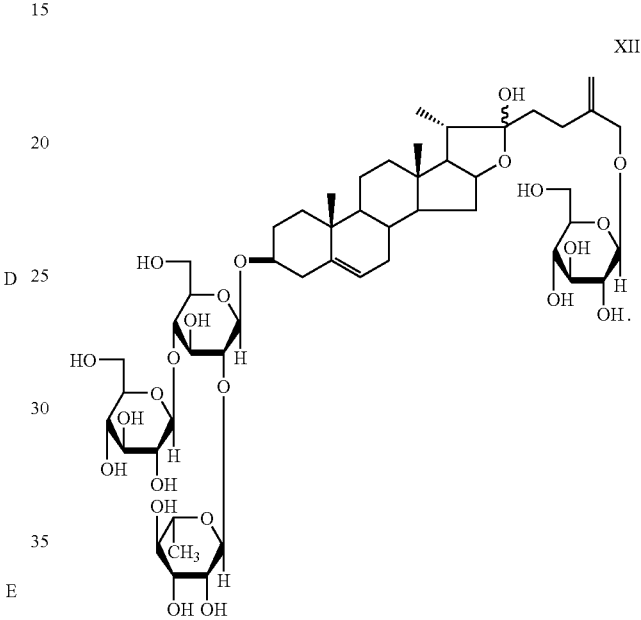

XII

8. A method according to claim 1 wherein, in the group of the formula (VII);

$R_{12}$, $R_{13}$, $R_{15}$, $R_{16}$, $R_{17}$, $R_{22}$, $R_{28}$ and $R_{32}$ each represent H;

$R_{14}$ is H, or $R_{14}$ and $R_{33}$ taken together represent the second bond of a double bond joining adjacent carbon atoms;

$R_{18}$ is H or —OH;

$R_{19}$ is —CH$_3$;

$R_{20}$ is —OH or $C_{1-6}$ alkoxy;

$R_{21}$ is of the formula VIII;

$R_{23}$ is —CH$_3$ or =CH$_2$;

$R_{24}$ is $C_{1-6}$ acyl or glucose;

$R_{29}$ is H or —OH;

$R_{33}$ is H; and

Y is O.

9. A method according to claim 1 wherein, in the formula (XI);

$R_{12}$, $R_{13}$, $R_{15}$, $R_{16}$, $R_{17}$, $R_{25}$, $R_{28}$, $R_{31}$, $R_{32}$ and $R_{34}$, each represent H;

$R_{14}$ is H, or $R_{14}$ and $R_{33}$ taken together represent the second bond of a double bond joining adjacent carbon atoms;

$R_{18}$ is H or —OH;

$R_{19}$ is CH$_3$;

$R_{26}$ is —CH$_3$ or =CH$_2$;

$R_{29}$ is H or —OH;

$R_{33}$ is H; and

X is O or NH.

10. A method according to claim 1 wherein, in the compound of the formula (IV) is selected from

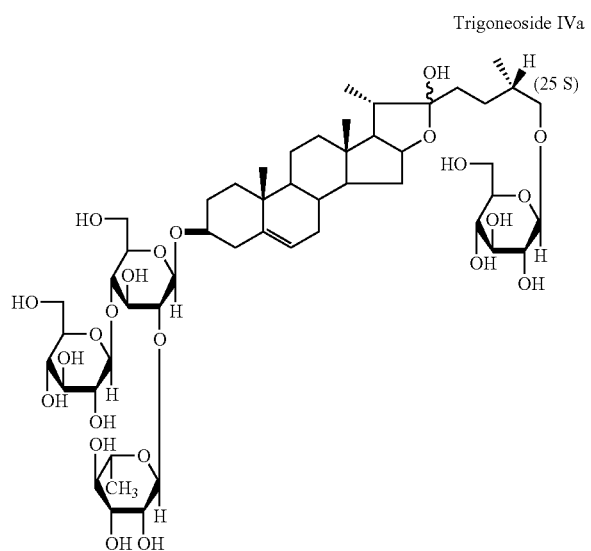

Trigoneoside IVa

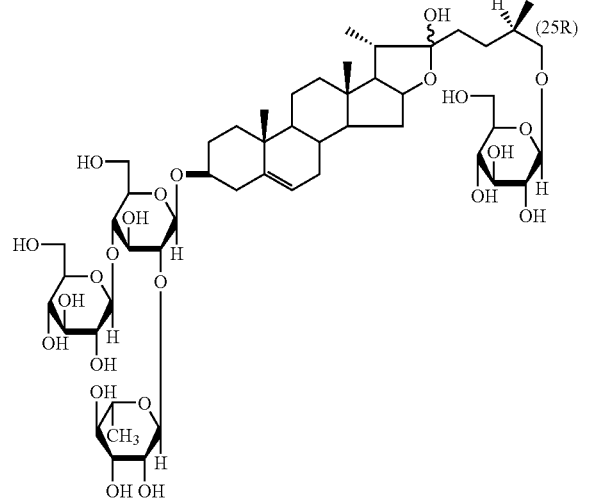

Glycoside F

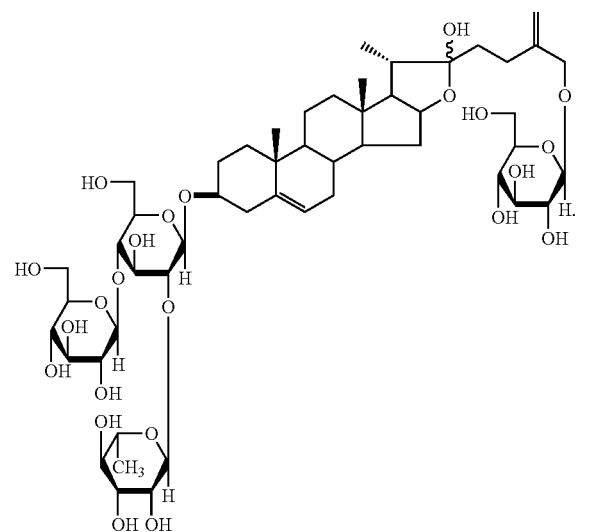

Compound 3

11. A method of treatment of a condition selected from an inflammatory disease, diabetic cardiomyopathy, myocardial dysfunction, cancer metastasis and diabetic retinopathy, comprising administering to a patient in need thereof, a plant extract comprising an effective amount of a compound of the formula (IV), with the proviso that if said plant extract is an extract of fenugreek, then said extract of fenugreek is essentially free of hypoglycemic activity

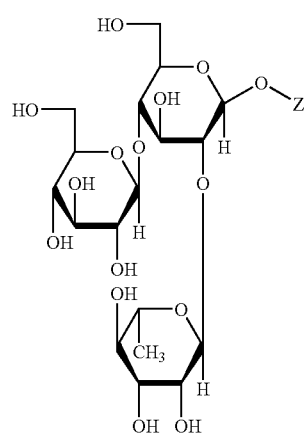

IV wherein Z is a group of the formula VII:

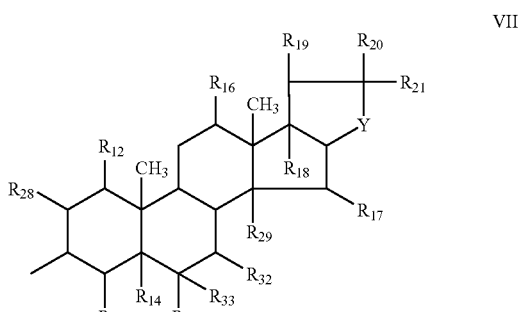

VII wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$ is H or —OH;
$R_{18}$ is H or —OH;
$R_{19}$ is H, or —CH$_3$;
$R_{20}$ is —OH or $C_{1-6}$ alkoxy;
$R_{21}$ is of the formula VIII;

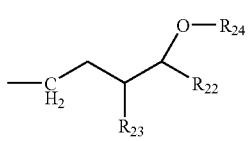

VIII $R_{22}$ is H, —OH, or —OMe;
$R_{23}$ is CH$_2$H$_4$OH, —CH$_2$OH, —CH$_3$ or =CH$_2$;
$R_{24}$ is $C_{1-6}$ alkyl, $C_{1-6}$ acyl, or glucose;
$R_{29}$ is H or —OH;
$R_{32}$ is H or —OH;

$R_{33}$ is H; and
Y is O;
or Z is a group of the formula XI:

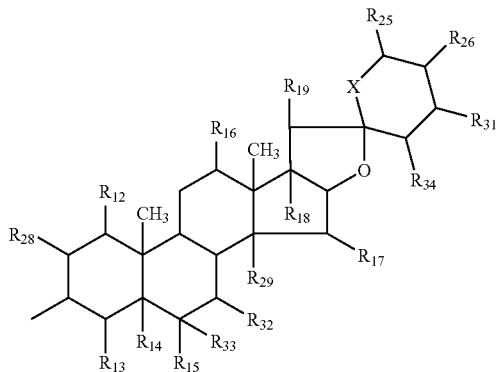

wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$, $R_{18}$, $R_{25}$, $R_{29}$, $R_{31}$, $R_{32}$, and $R_{34}$ are independently selected from H and —OH;
$R_{19}$ is H, or $CH_3$;
$R_{26}$ is $CH_2H_4OH$, —$CH_2OH$, —$CH_3$ or =$CH_2$;
$R_{33}$ is H; and
X is O or NH;
or a pharmaceutically acceptable salt, ester or tautomeric form thereof.

12. A method according to claim 11 wherein, in the group of the formula (VII);
$R_{12}$, $R_{13}$, $R_{15}$, $R_{16}$, $R_{17}$, $R_{22}$, $R_{28}$ and $R_{32}$ each represent H;
$R_{14}$ is H, or $R_{14}$ and $R_{33}$ taken together represent the second bond of a double bond joining adjacent carbon atoms;
$R_{18}$ is H or —OH;
$R_{19}$ is $CH_3$;
$R_{20}$ is —OH or $C_{1-6}$ alkoxy;
$R_{21}$ is of the formula VIII;
$R_{23}$ is —$CH_3$ or $CH_2$;
$R_{24}$ is $C_{1-6}$ acyl or glucose;
$R_{29}$ is H or —OH;
$R_{33}$ is H; and
Y is O.

13. A method according to claim 11 in which the group of the formula (VII) is selected from the group consisting of:

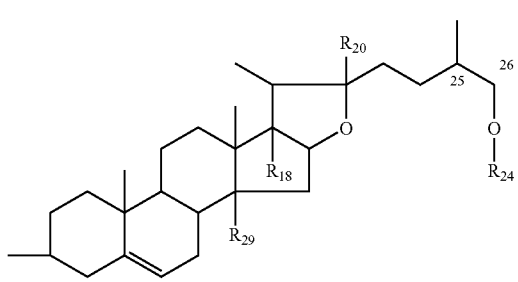

G

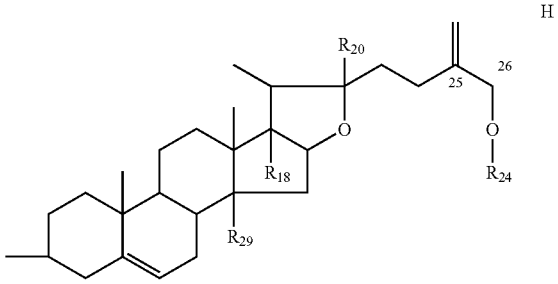

H

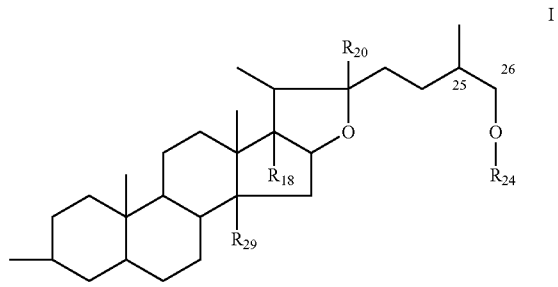

I

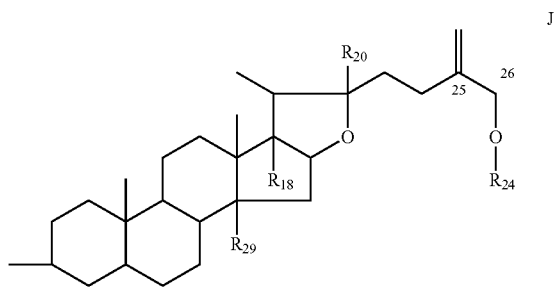

J wherein:
$R_{16}$ is H or —OH;
$R_{20}$ is —OH or $C_{1-6}$ alkoxy;
$R_{24}$ is glucose or $C_{1-6}$ acyl; and
$R_{29}$ is H or —OH.

14. A method according to claim 11 in which the compound of the formula IV is selected from the group consisting of:

Trigoneoside IVa which is (3β,25S)-26-(β-D-glucopyranosyloxy)-22-hydroxy furost-5-en-3-yl-O-α-L-rhamnopyranosyl-(1→2)-O-[β-D-glucopyranosyl-(1→4)]-β-D-glucopyranoside, Glycoside F which is (3β)-26-(β-D-glucopyranosyloxy)-22-hydroxyfurost-5-en-3-yl-O-α-L-rhamnopyranosyl-(1→2)-O-[β-D-glucopyranosyl-(1→4)]-β-D-glucopyranoside, Shatavarin I, Compound 3, Pardarinoside C.

15. A method according to claim 10 in which the compound of the formula IV is selected from the group consisting of

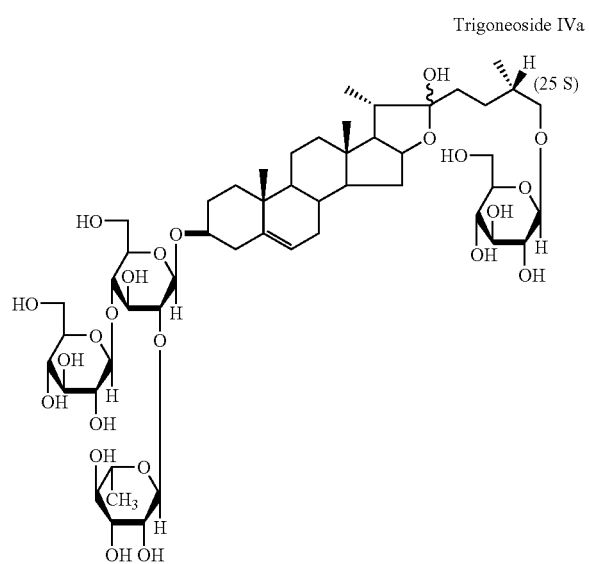

Trigoneoside IVa

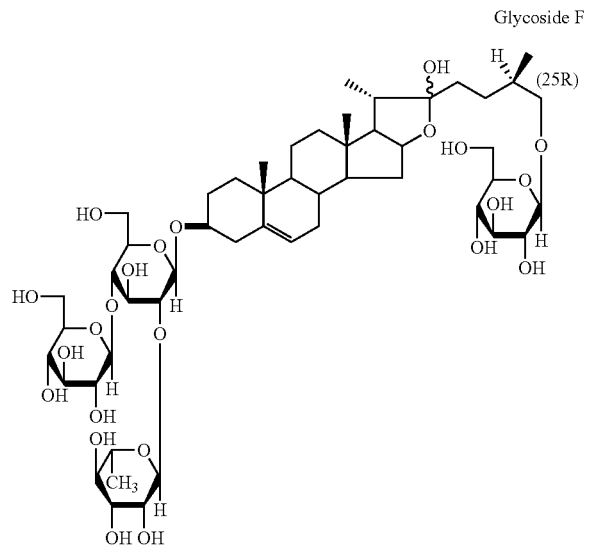

Glycoside F

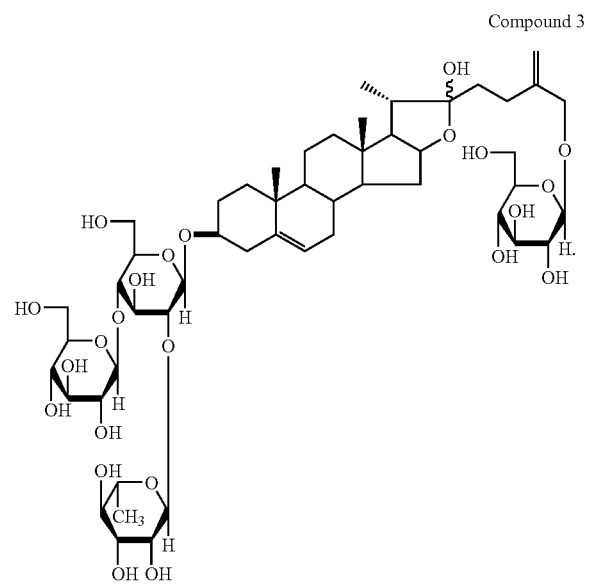

Compound 3

16. A method according to claim 11 wherein, in the formula (XI);

$R_{12}$, $R_{13}$, $R_{15}$, $R_{16}$, $R_{17}$, $R_{25}$, $R_{28}$, $R_{31}$, $R_{32}$ and $R_{34}$, each represent H;

$R_{14}$ is H, or $R_{14}$ and $R_{33}$ taken together represent the second bond of a double bond joining adjacent carbon atoms;

$R_{18}$ is H or —OH;

$R_{19}$ is —CH$_3$;

$R_{26}$ is —CH$_3$ or CH$_2$;

$R_{29}$ is H or —OH;

$R_{33}$ is H; and

X is O or NH.

17. A method according to claim 11 in which the group of the formula XI is selected from the group consisting of:

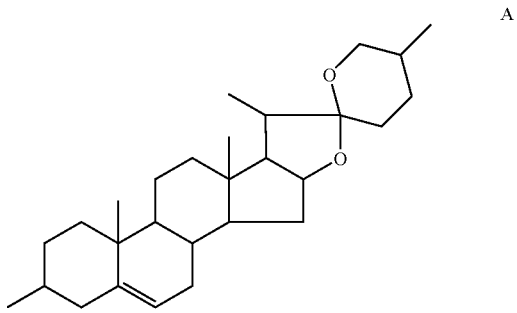

A

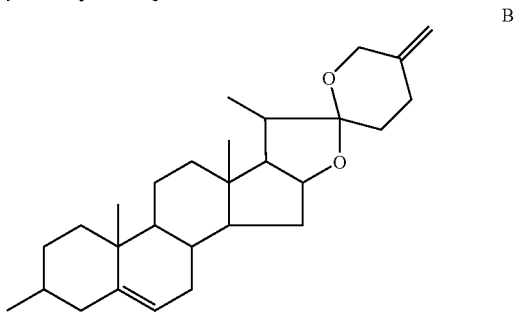

B

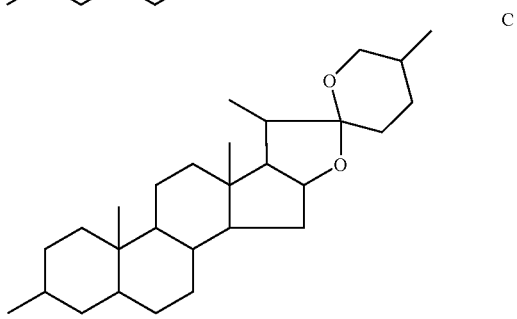

C

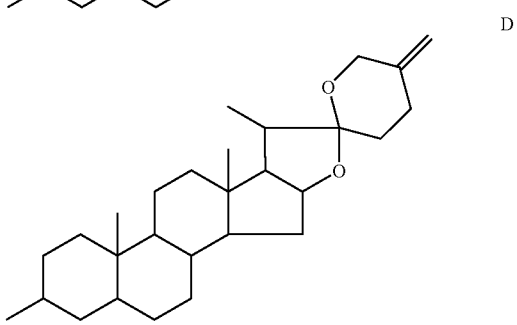

D

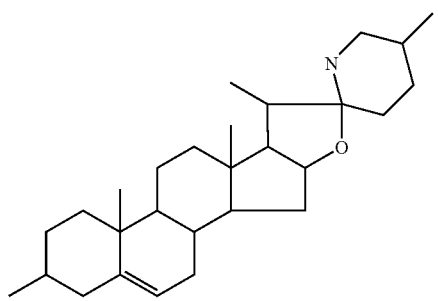

E

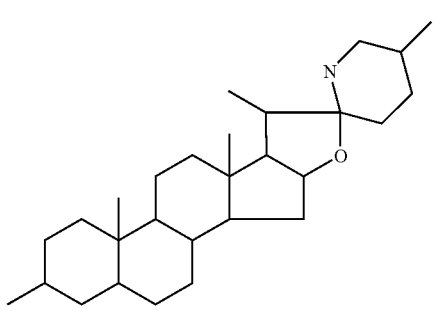

F

18. A method according to claim 11 in which the group of the formula XI is selected from the group consisting of diosgenin, yamogenin, tigogenin, neotigogenin, sarsasapogenin, smilagenin, hecogenin, solasodine or tomatidine.

19. A method according to claim 11 in which the compound of the formula IV is selected from the group consisting of:

Shatavarin IV which is sarsasapogenin 3-O-α-L-rhamnopyranosyl-(1→2)-O-[β-D-glucopyranosyl-(1→4)]-β-D-glucopyranoside, Compound 12 which is solasodine 3-O-α-L-rhamnopyranosyl-(1→2)-O-[β-D-glucopyranosyl-(1→4)]-β-D-glucopyranoside, Deltonin which is (3β,25R)-spirost-5-en-3-yl-O-α-L-rhamnopyranosyl-(1→2)-O-[β-D-glucopyranosyl-(1→4)]-β-D-Gluco-pyranoside, and Balanitin VI is (3β,25S)-spirost-5-en-3-yl-O-α-L-rhamnopyranosyl-(1→2)-O-[β-D-glucopyranosyl-(1→4)]-β-D-Glucopyranoside.

20. A method according to claim 11 wherein said plant extract is a component of a pharmaceutical composition which additionally comprises a pharmaceutically acceptable diluent or excipient.

21. An isolated compound of the formula:

XII

22. A method of treatment of a condition selected from an inflammatory disease, diabetic cardiomyopathy, myocardial dysfunction, cancer metastasis and diabetic retinopathy, comprising administering to a patient in need thereof, a plant extract comprising an effective amount of a compound of the formula (IV), with the proviso that if said plant extract is an extract of fenugreek, then said extract of fenugreek is essentially free of 4-hydroxyisoleucine

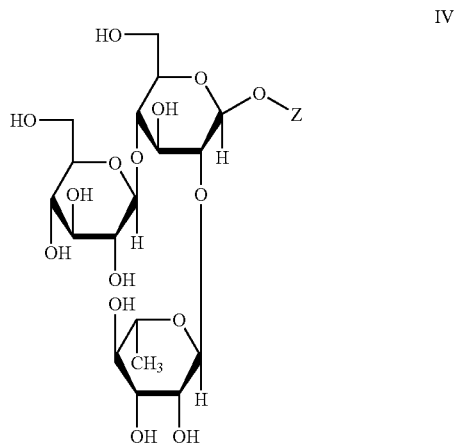

IV wherein Z is a group of the formula VII:

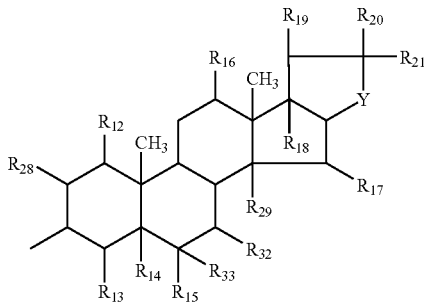

wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$ is H or —OH;
$R_{18}$ is H or —OH;
$R_{19}$ is H, or —CH$_3$;
$R_{20}$ is —OH or C$_{1-6}$ alkoxy;
$R_{21}$ is of the formula VIII;

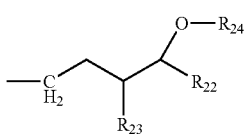

$R_{22}$ is H, —OH, or —OMe;
$R_{23}$ is CH$_2$H$_4$OH, —CH$_2$OH, —CH$_3$ or CH$_2$;
$R_{24}$ is C$_{1-6}$ alkyl, C$_{1-6}$ acyl, or glucose;
$R_{29}$ is H or —OH;
$R_{32}$ is H or —OH;
$R_{33}$ is H; and
Y is O;
or Z is a group of the formula XI:

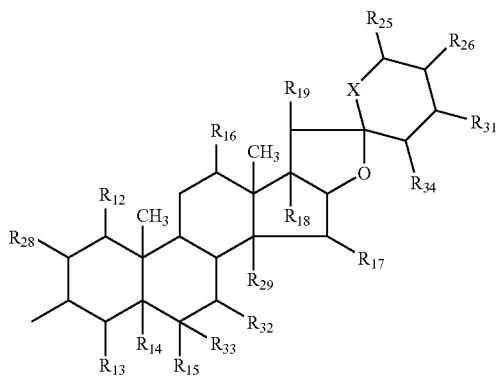

wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$, $R_{18}$, $R_{25}$, $R_{29}$, $R_{31}$, $R_{32}$, and $R_{34}$ are independently selected from H and —OH;

$R_{19}$ is H, or —CH$_3$;
$R_{26}$ is —CH$_{22}$H$_4$OH, —CH$_2$OH, —CH$_3$ or =CH$_2$;
$R_{33}$ is H; and
X is O or NH;
or a pharmaceutically acceptable salt, ester or tautomeric form thereof.

23. A method according to claim 22 wherein, in the group of the formula (VII);
$R_{12}$, $R_{13}$, $R_{15}$, $R_{16}$, $R_{17}$, $R_{22}$, $R_{28}$ and $R_{32}$ each represent H;
$R_{14}$ is H, or $R_{14}$ and $R_{33}$ taken together represent the second bond of a double bond joining adjacent carbon atoms;
$R_{18}$ is H or —OH;
$R_{19}$ is CH$_3$;
$R_{20}$ is —OH or C$_{1-6}$ alkoxy;
$R_{21}$ is of the formula VIII;
$R_{23}$ is —CH$_3$ or =CH$_2$;
$R_{24}$ is C$_{1-6}$ acyl or glucose;
$R_{29}$ is H or —OH;
$R_{33}$ is H; and
Y is O.

24. A method according to claim 22 in which the group of the formula (VII) is selected from the group consisting of:

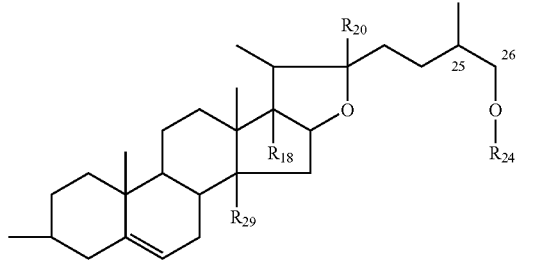

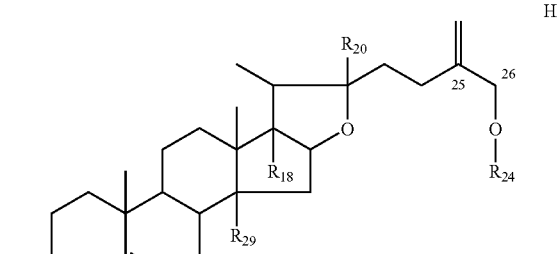

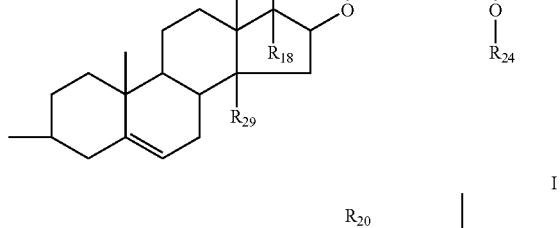

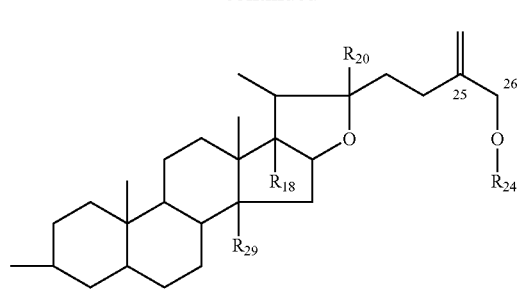

J wherein:

$R_{18}$ is H or —OH;

$R_{20}$ is —OH or $C_{1-6}$ alkoxy;

$R_{24}$ is glucose or $C_{1-6}$ acyl; and $R_{29}$ is H or —OH.

25. A method according to claim 22 in which the compound of the formula IV is selected from the group consisting of:

Trigoneoside IVa which is (3β,25S)-26-(β-D-glucopyranosyloxy)-22-hydroxy furost-5-en-3-yl-O-α-L-rhamnopyranosyl-(1→2)-O-[β-D-glucopyranosyl-(1→4)]-β-D-glucopyranoside, Glycoside F which is (3β)-26-(β-D-glucopyranosyloxy)-22-hydroxyfurost-5-en-3-yl-O-α-L-rhamnopyranosyl-(1→2)-O-[β-D-glucopyranosyl-(1→4)]-β-D-glucopyranoside, Shatavarin I, Compound 3, Pardarinoside C.

26. A method according to claim 22 in which the compound of the formula IV is selected from the group consisting of:

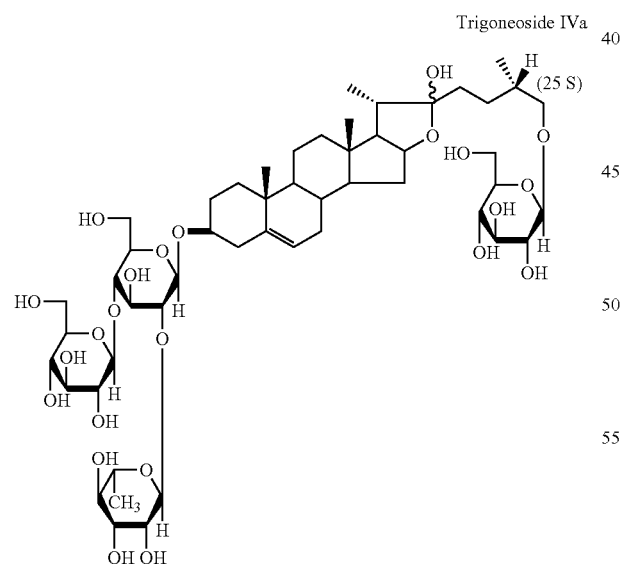

Trigoneoside IVa

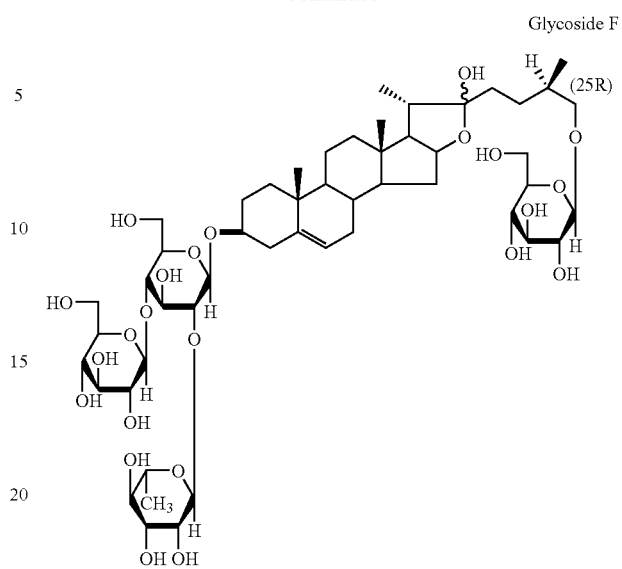

Glycoside F

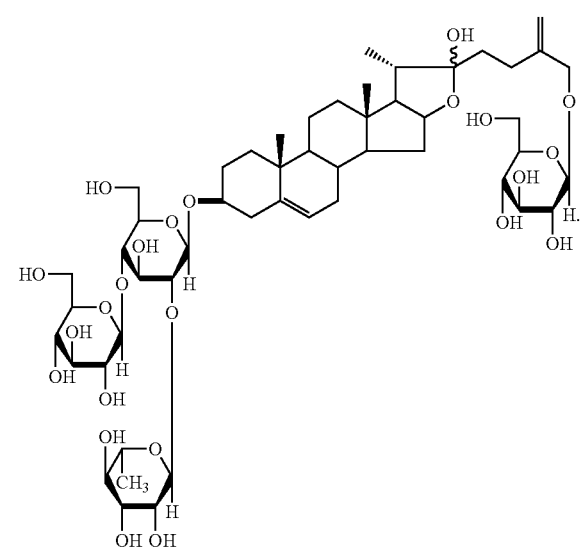

Compound 3

27. A method according to claim 22 wherein, in the formula (XI);

$R_{12}$, $R_{13}$, $R_{15}$, $R_{16}$, $R_{17}$, $R_{25}$, $R_{28}$, $R_{31}$, $R_{32}$ and $R_{34}$, each represent H;

$R_{14}$ is H, or $R_{14}$ and $R_{33}$ taken together represent the second bond of a double bond joining adjacent carbon atoms $R_{18}$ is H or —OH;

$R_{19}$ is —CH₃;

$R_{26}$ is —CH₃ or CH₂;

$R_{29}$ is H or —OH;

$R_{33}$ is H; and

X is O or NH.

28. A method according to claim 22 in which the group of the formula XI is selected from the group consisting of:

A
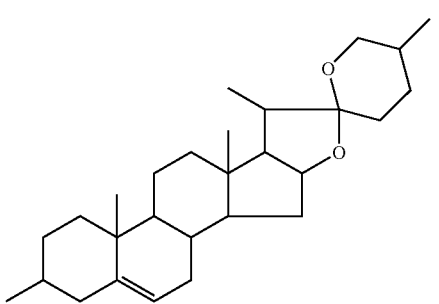

B
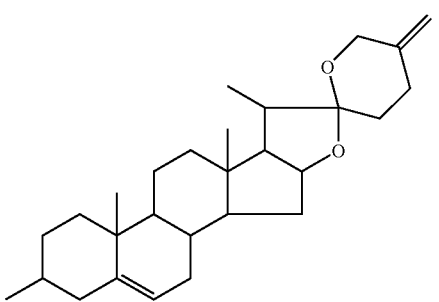

C
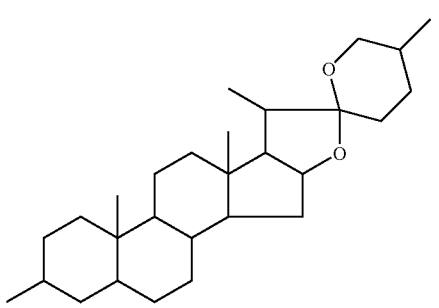

D
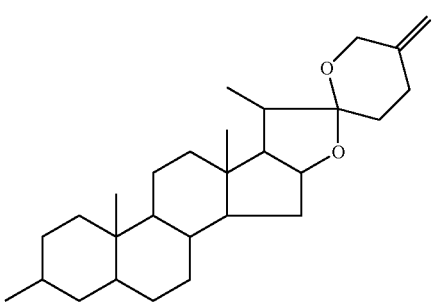

E
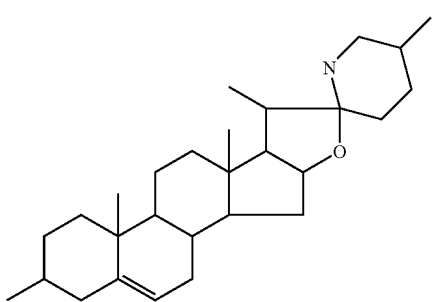

F
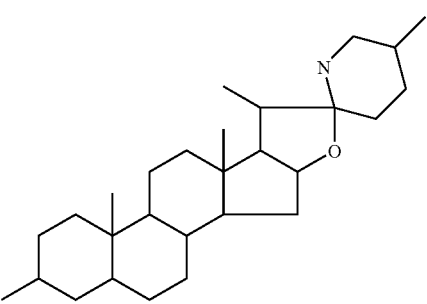

29. A method according to claim 22 in which the group of the formula XI is selected from the group consisting of diosgenin, yamogenin, tigogenin, neotigogenin, sarsasapogenin, smilagenin, hecogenin, solasodine or tomatidine.

30. A method according to claim 22 in which the compound of the formula IV is selected from the group consisting of:

Shatavarin IV which is sarsasapogenin 3-O-α-L-rhamnopyranosyl-(1→2)-O-[β-D-glucopyranosyl-(1→4)]-β-D-glucopyranoside, Compound 12 which is solasodine 3-O-α-L-rhamnopyranosyl-(1→2)-O-[β-D-glucopyranosyl-(1→4)]-β-D-glucopyranoside, Deltonin which is (3β,25R)-spirost-5-en-3-yl-O-α-L-rhamnopyranosyl-(1→2)-O-[β-D-glucopyranosyl-(1→4)]-β-D-Gluco-pyranoside, and Balanitin VI is (3β,25S)-spirost-5-en-3-yl-O-α-L-rhamnopyranosyl-(1→2)-O-[β-D-glucopyranosyl-(1→4)]-β-D-Glucopyranoside.

31. A method according to either of claim 11 or claim 22 wherein said plant extract is a component of a pharmaceutical composition which additionally comprises a pharmaceutically acceptable diluent or excipient.

32. A method of treatment of a condition selected from an inflammatory disease, diabetic cardiomyopathy, myocardial dysfunction, cancer metastasis and diabetic retinopathy, comprising administering to a patient in need thereof, an extract of fenugreek, said extract of fenugreek being essentially free of hypoglycemic activity and comprising an effective amount of a compound selected from

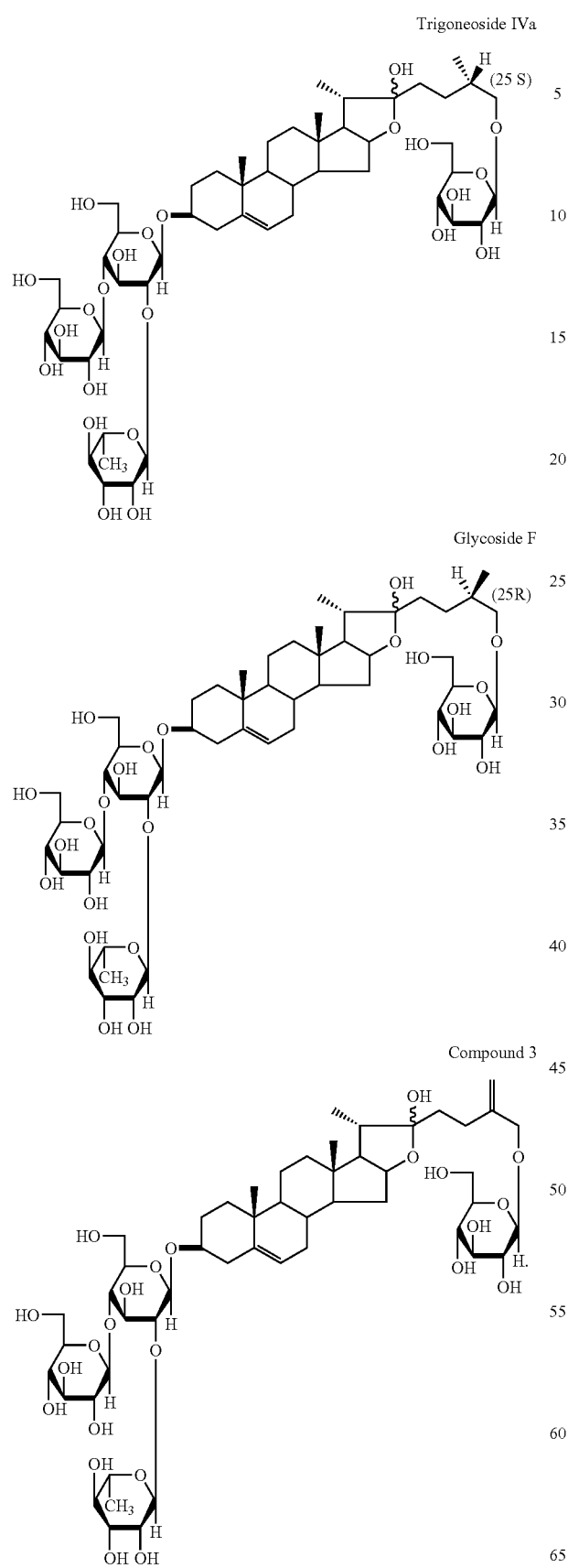

Trigoneoside IVa

Glycoside F

Compound 3

33. A method of treatment of a condition selected from an inflammatory disease, diabetic cardiomyopathy, myocardial dysfunction, cancer metastasis and diabetic retinopathy, comprising administering to a patient in need thereof, an extract of fenugreek, said extract of fenugreek being essentially free of 4-hydroxyisoleucine and comprising an effective amount of a compound selected from

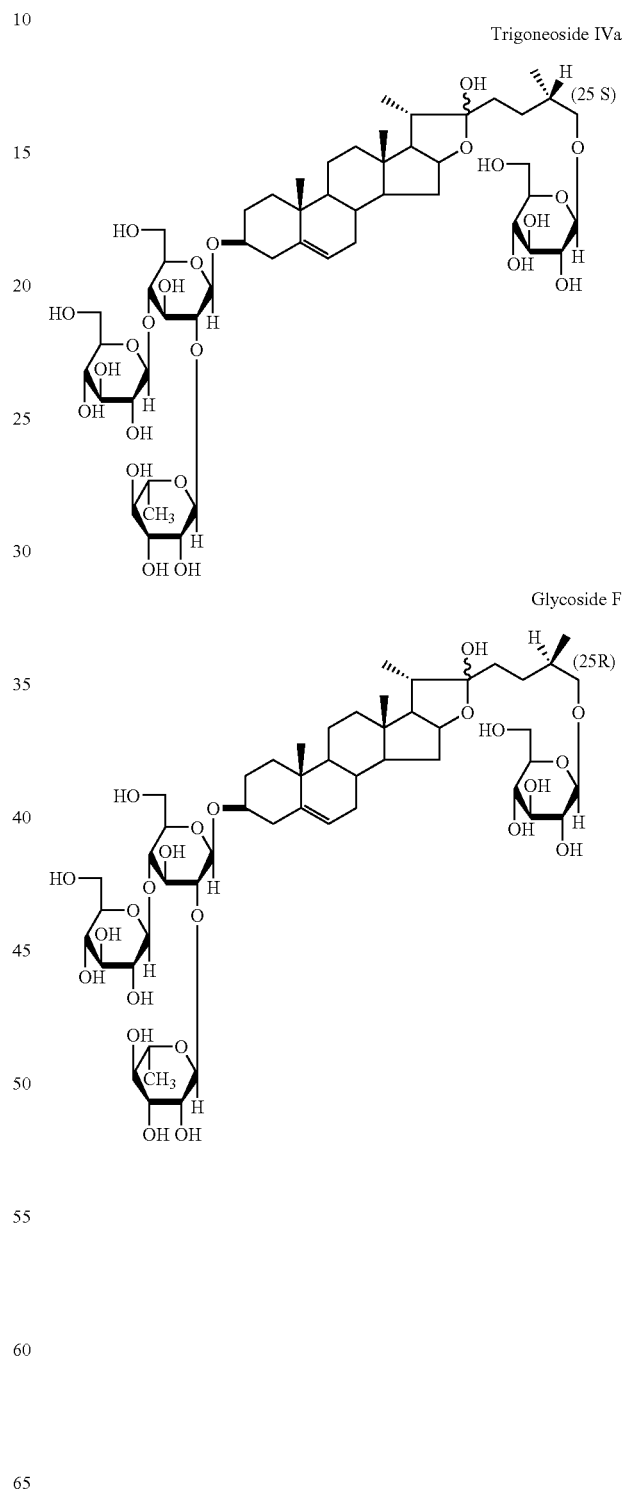

Trigoneoside IVa

Glycoside F

Compound 3

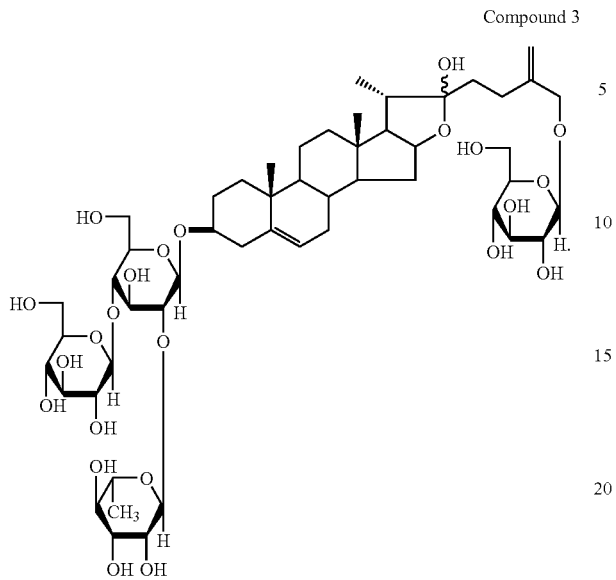

34. A method according to claim 32 or 33 wherein the extract of fenugreek is an extract of fenugreek seeds.

35. A method of treatment of a condition selected from an inflammatory disease, diabetic cardiomyopathy, myocardial dysfunction, cancer metastasis and diabetic retinopathy, comprising administering to a patient in need thereof, a single compound of the formula (IV)

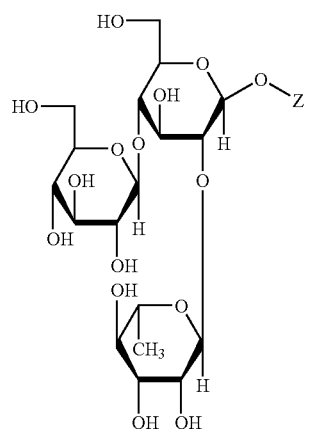

IV wherein Z is a group of the formula VII:

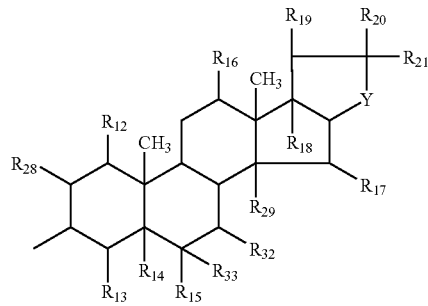

VII wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$ is H or —OH;
$R_{18}$ is H or —OH;
$R_{19}$ is H, or —CH$_3$;
$R_{20}$ is —OH or $C_{1-6}$ alkoxy;
$R_{21}$ is of the formula VIII;

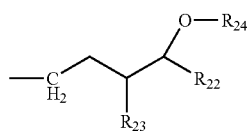

VIII $R_{22}$ is H, —OH, or —OMe;
$R_{23}$ is —CH$_2$H$_4$OH, —CH$_2$OH, —CH$_3$ or =CH$_2$
$R_{24}$ is $C_{1-6}$ alkyl, $C_{1-6}$ acyl, or glucose;
$R_{29}$ is H or —OH;
$R_{32}$ is H or —OH;
$R_{33}$ is H; and
Y is O
or Z is a group of the formula XI:

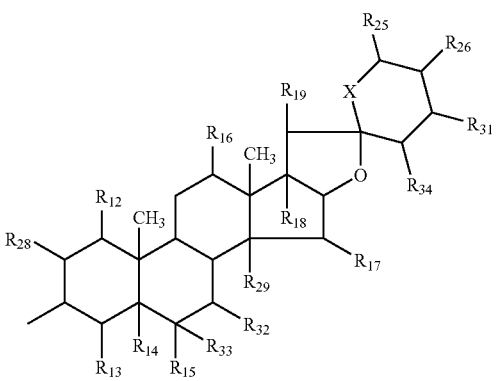

XI wherein:
$R_{12}$, $R_{13}$, $R_{15}$ and $R_{28}$ each represent H;
$R_{14}$ is H, or $R_{14}$ and $R_{33}$ taken together represent the second bond of a double bond joining adjacent carbon atoms;
$R_{16}$ is H, or =O;
$R_{17}$, $R_{18}$, $R_{25}$, $R_{29}$, $R_{31}$, $R_{32}$, and $R_{34}$ are independently selected from H and —OH;

$R_{19}$ is H, or —$CH_3$;

$R_{26}$ is —$CH_2H_4OH$, —$CH_2OH$, —$CH_3$ or =$CH_2$;

$R_{33}$ is H; and

X is O or NH;

or a pharmaceutically acceptable salt, ester or tautomeric form thereof.

36. A method according to claim 35 wherein, in the group of the formula (VII);

$R_{12}, R_{13}, R_{15}, R_{16}, R_{17}, R_{22}, R_{28}$ and $R_{32}$ each represent H;

$R_{14}$ is H, or $R_{14}$ and $R_{33}$ taken together represent the second bond of a double bond joining adjacent carbon atoms;

$R_{18}$ is H or —OH;

$R_{19}$ is —$CH_3$;

$R_{20}$ is —OH or $C_{1-6}$ alkoxy;

$R_{21}$ is of the formula VIII;

$R_{23}$ is —$CH_3$ or =$CH_2$;

$R_{24}$ is $C_{1-6}$ acyl or glucose;

$R_{29}$ is H or —OH;

$R_{33}$ is H; and

Y is O, and in the group of the formula XI;

$R_{12}, R_{13}, R_{15}, R_{16}, R_{17}, R_{25}, R_{28}, R_{31}, R_{32}$ and $R_{34}$, each represent H;

$R_{14}$ is H, or $R_{14}$ and $R_{33}$ taken together represent the second bond of a double bond joining adjacent carbon atoms;

$R_{18}$ is H or —OH;

$R_{19}$ is —$CH_3$;

$R_{26}$ is —$CH_3$ or =$CH_2$, $R_{29}$ is H or —OH;

$R_{33}$ is H; and

X is O or NH.

37. A method according to claim 35 in which the group of the formula (VII) is selected from the group consisting of:

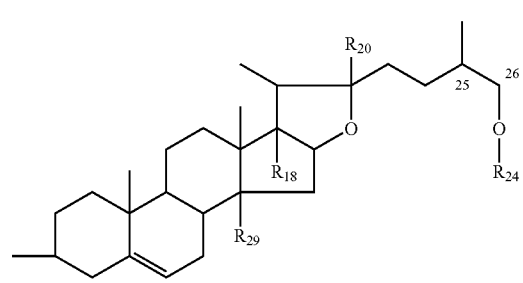

G

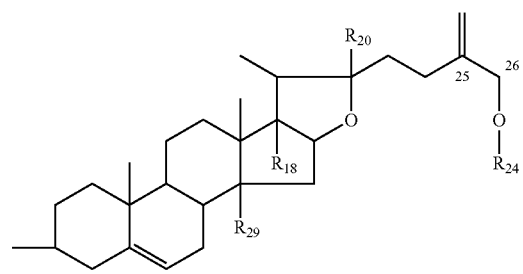

H

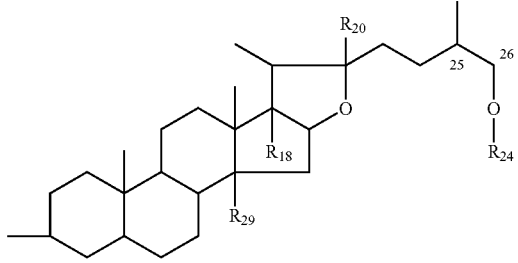

I

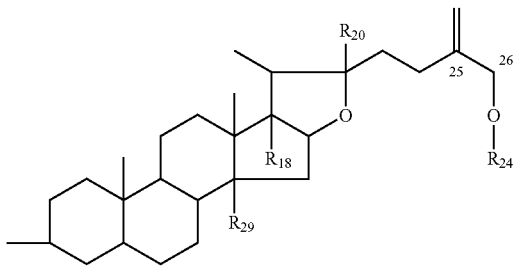

J wherein:

$R_{18}$ is H or —OH;

$R_{20}$ is —OH or $C_{1-6}$ alkoxy;

$R_{24}$ is glucose or $C_{1-6}$ acyl; and $R_{29}$ is H or —OH;

and the group of the formula XI is selected from the group consisting of

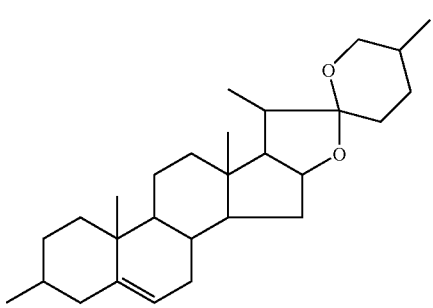

A

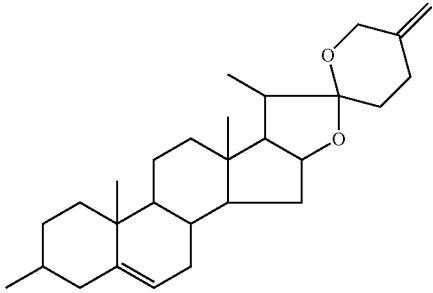

B

-continued

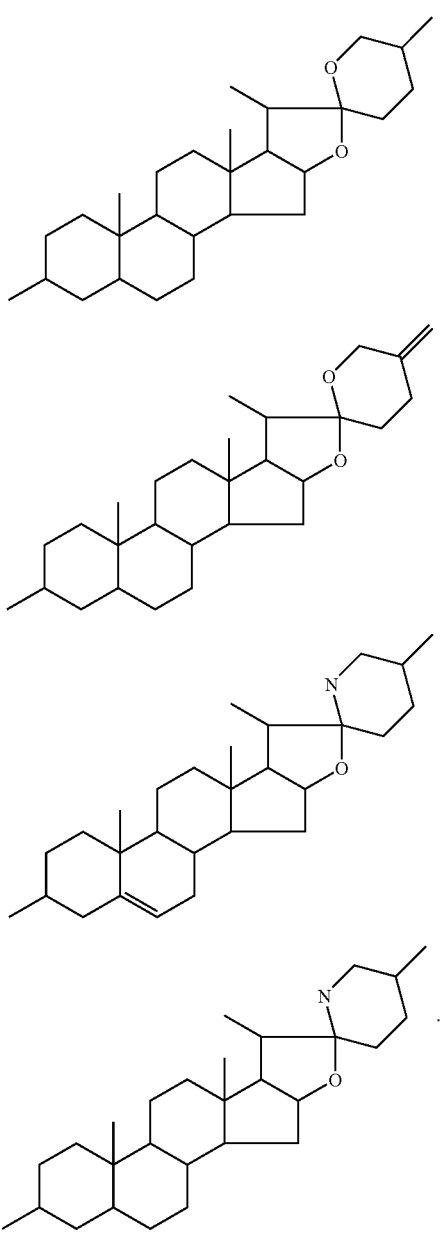

C

D

E

F

38. A method according to claim 35 comprising administering to a patient in need thereof, a single compound selected from the group consisting of:

Trigoneoside IVa which is (3β,25S)-26-(β-D-glucopyranosyloxy)-22-hydroxy furost-5-en-3-yl-O-α-L-rhamnopyranosyl-(1→42)-O-[β-D-glucopyranosyl-(1→4)]-β-D-glucopyranoside, Glycoside F which is (3β)-26-(β-D-glucopyranosyloxy)-22-hydroxyfurost-5-en-3-yl-O-α-L-rhamnopyranosyl-(1→2)-O-[β-D-glucopyranosyl-(1→4)]-β-D-glucopyranoside, Shatavarin I, Compound 3, Pardarinoside C Shatavarin IV which is sarsasapogenin 3-O-α-L-rhamnopyranosyl-(1→2)-O-[β-D-glucopyranosyl-(1→4)]-β-D-glucopyranoside, Compound 12 which is solasodine 3-O-α-L-rhamnopyranosyl-(1→2)-O-[β-D-glucopyranosyl-(1→4)]-β-D-glucopyranoside, Deltonin which is (3β, 25R)-spirost-5-en-3-yl-O-α-L-rhamnopyranosyl-(1→2)-O-[β-D-glucopyranosyl-(1→4)]-β-D-Glucopyranoside, and Balanitin VI is (3β,25S)-spirost-5-en-3-yl-O-α-L-rhamnopyranosyl-(1→2)-O-[β-D-glucopyranosyl-(1→4)]-β-D-Glucopyranoside.

39. A method according to claim 35 comprising administering to a patient in need thereof, a single compound of the formula IV selected from the group consisting of:

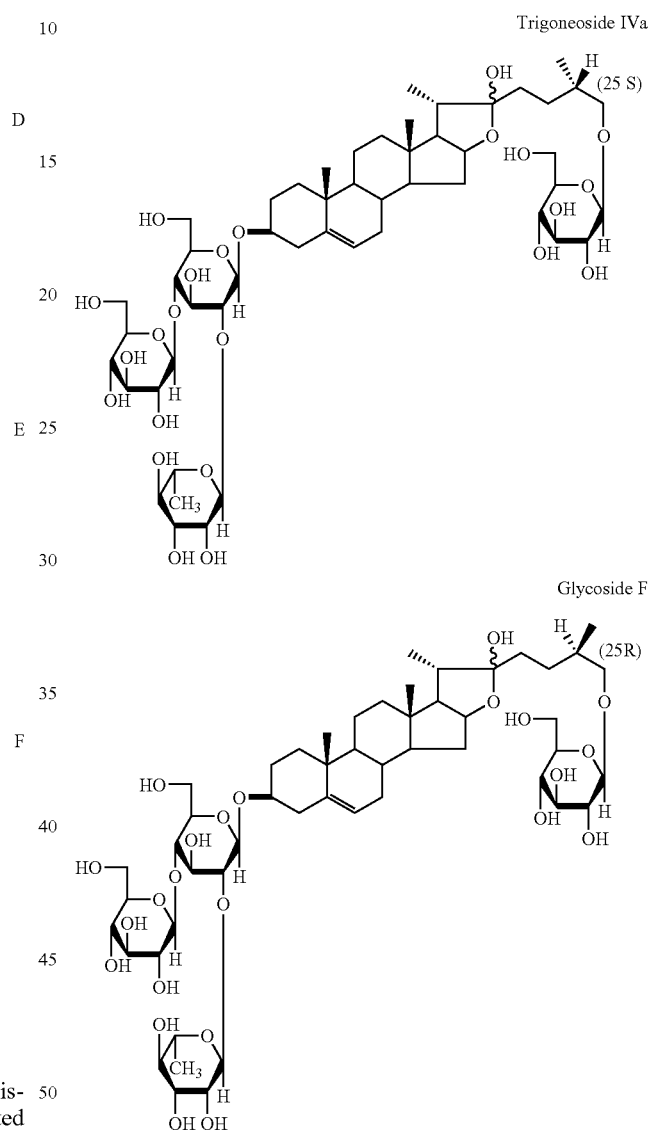

Trigoneoside IVa

Glycoside F

-continued

Compound 3

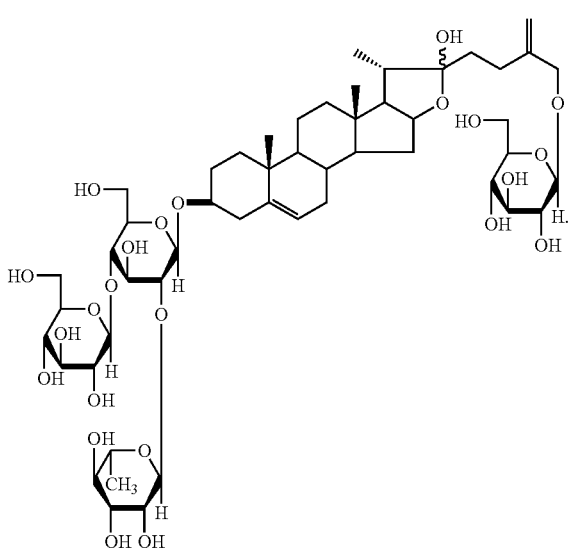

40. A method according to claim 1, 11, 22, 32, 33 or 35 wherein the compound is administered at a dose of 0.01 to 10 mg per kilogram of body weight of the recipient per day.

41. A method according to claim 1, 11, 22, 32, 33 or 35 wherein the compound is administered at a dose of 0.2 to 1 mg per kilogram of body weight of the recipient per day.

42. A method according to claim 1, 11, 22, 32, 33 or 35 comprising administration of a unit dose of between 10 and 1500 mg of the compound to a patient in need thereof.

43. A method according to claim 1, 11, 22, 32, 33 or 35 comprising administration of a unit dose of between 20 and 1000 mg of the compound to a patient in need thereof.

44. A method according to claim 1, 11, 22, 32, 33 or 35 comprising administration of a unit dose of between 50 and 700 mg of the compound to a patient in need thereof.

45. A method according to claim 1, 11, 22, 32, 33 or 35 wherein the compound is administered by the oral route.

46. A method according to claim 1, 11, 22, 32, 33 or 35 wherein the compound is administered by the parenteral route.

47. A method according to claim 1, 11, 22, 32, 33 or 35 wherein the compound is administered by the transdermal route.

48. A method according to claim 1, 11, 22, 32, 33 or 35 wherein the compound is administered by the airway, rectal, vaginal or topical route.

49. A method according to claim 1, 11, 22, 32, 33 or 35 wherein the inflammatory disease is selected from asthma, rheumatoid arthritis, atherosclerosis, and inflammatory bowel disease.

* * * * *

UNITED STATES PATENT AND TRADEMARK OFFICE
CERTIFICATE OF CORRECTION

PATENT NO. : 7,906,493 B2
APPLICATION NO. : 10/584470
DATED : March 15, 2011
INVENTOR(S) : Chibber It is certified that error appears in the above-identified patent and that said Letters Patent is hereby corrected as shown below:

Column 37 line 39, the phrase "cancer," should be deleted.

Signed and Sealed this
Eighth Day of May, 2012

David J. Kappos
*Director of the United States Patent and Trademark Office*